(12) United States Patent
Nishino et al.

(10) Patent No.: US 10,590,380 B2
(45) Date of Patent: Mar. 17, 2020

(54) CULTURE MEDIUM COMPOSITION AND METHOD OF CULTURING CELL OR TISSUE USING THEREOF

(71) Applicants: Nissan Chemical Industries, Ltd., Tokyo (JP); Kyoto University, Kyoto-shi (JP)

(72) Inventors: Taito Nishino, Shiraoka (JP); Tatsuro Kanaki, Shiraoka (JP); Ayako Otani, Shiraoka (JP); Koichiro Saruhashi, Funabashi (JP); Misayo Tomura, Funabashi (JP); Takehisa Iwama, Funabashi (JP); Masato Horikawa, Tokyo (JP); Norio Nakatsuji, Kyoto (JP); Tomomi Otsuji, Kyoto (JP)

(73) Assignees: Nissan Chemical Industries, Ltd., Tokyo (JP); Kyoto University, Kyoto (JP)

( * ) Notice: Subject to any disclaimer, the term of this patent is extended or adjusted under 35 U.S.C. 154(b) by 0 days.

(21) Appl. No.: 15/448,557

(22) Filed: Mar. 2, 2017

(65) Prior Publication Data
US 2017/0175077 A1 Jun. 22, 2017

Related U.S. Application Data

(63) Continuation of application No. 13/949,310, filed on Jul. 24, 2013, now Pat. No. 9,664,671.

(60) Provisional application No. 61/759,172, filed on Jan. 31, 2013, provisional application No. 61/731,824, filed on Nov. 30, 2012, provisional application No. 61/675,133, filed on Jul. 24, 2012.

(51) Int. Cl.
| | |
|---|---|
| *C12N 5/00* | (2006.01) |
| *G01N 33/50* | (2006.01) |
| *C12N 5/071* | (2010.01) |
| *C12N 5/09* | (2010.01) |

(52) U.S. Cl.
CPC ........... *C12N 5/0043* (2013.01); *C12N 5/005* (2013.01); *C12N 5/067* (2013.01); *C12N 5/0693* (2013.01); *G01N 33/5011* (2013.01); *G01N 33/5014* (2013.01); *G01N 33/5044* (2013.01); *G01N 33/5067* (2013.01); *C12N 2500/14* (2013.01); *C12N 2500/34* (2013.01); *C12N 2531/00* (2013.01); *C12N 2533/80* (2013.01)

(58) Field of Classification Search
None
See application file for complete search history.

(56) References Cited

U.S. PATENT DOCUMENTS

| | | | |
|---|---|---|---|
| 5,968,501 A | 10/1999 | Comoglio | |
| 6,242,035 B1 | 6/2001 | Clark et al. | |
| 6,284,451 B1 | 9/2001 | Funatsu et al. | |
| 8,609,377 B2 | 12/2013 | Yang et al. | |
| 2004/0091460 A1 | 5/2004 | Purcell et al. | |
| 2005/0084933 A1 | 4/2005 | Schilling et al. | |
| 2006/0121606 A1 | 6/2006 | Ito et al. | |
| 2006/0286627 A1 | 12/2006 | Bochner et al. | |
| 2007/0074451 A1 | 4/2007 | Pearce et al. | |
| 2007/0292949 A1 | 12/2007 | Duguay et al. | |
| 2008/0070280 A1 | 3/2008 | Schilling et al. | |
| 2008/0107789 A1* | 5/2008 | Akimoto | A23L 29/238 426/573 |
| 2008/0145505 A1 | 6/2008 | Bezanson et al. | |
| 2008/0166751 A1 | 7/2008 | Asahara et al. | |
| 2008/0220526 A1* | 9/2008 | Ellison | C12N 5/0068 435/402 |
| 2009/0104141 A1 | 4/2009 | Ikeda et al. | |
| 2010/0145470 A1 | 6/2010 | Cohen et al. | |
| 2010/0178275 A1 | 7/2010 | Spanholtz | |
| 2011/0066111 A1 | 3/2011 | Teschner et al. | |
| 2011/0117061 A1 | 5/2011 | Zhang et al. | |
| 2011/0269232 A1 | 11/2011 | Takahashi et al. | |
| 2012/0087899 A1 | 4/2012 | Cool et al. | |
| 2012/0141975 A1 | 6/2012 | Sato et al. | |
| 2012/0213745 A1 | 8/2012 | Duguay et al. | |
| 2014/0106348 A1 | 4/2014 | Nishino et al. | |
| 2014/0162318 A1 | 6/2014 | Tomura et al. | |
| 2016/0060601 A1 | 3/2016 | Nishino et al. | |

FOREIGN PATENT DOCUMENTS

| | | |
|---|---|---|
| CN | 101591399 A | 12/2009 |
| CN | 101948815 A | 1/2011 |
| CN | 102471762 A | 5/2012 |

(Continued)

OTHER PUBLICATIONS

Buehring, Gertrude Case. "Culture of mammary epithelial cells from bovine milk." Journal of dairy science 73.4 (1990): 956-963. (Year: 1990).*
Definition of "culture medium", Cambridge University Press. (2008). Cambridge online dictionary, accessible at: https://dictionary.cambridge.org/us/dictionary/english/culture-medium (Year: 2008).*
Baird, J. K., P. A. Sandford, and I. W. Cottrell. "Industrial applications of some new microbial polysaccharides." Bio/Technology 1.9 (1983): 778. (Year: 1983).*

(Continued)

*Primary Examiner* — Robert J Yamasaki
(74) *Attorney, Agent, or Firm* — Leydig, Voit & Mayer, Ltd.

(57) ABSTRACT

The present invention provides a culture method of cells and/or tissues including culturing cells and/or tissues in a suspended state by using a medium composition wherein indeterminate structures are formed in a liquid medium, the structures are uniformly dispersed in the solution and substantially retain the cells and/or tissues without substantially increasing the viscosity of the solution, thus affording an effect of preventing sedimentation thereof, and the like.

12 Claims, 16 Drawing Sheets
(14 of 16 Drawing Sheet(s) Filed in Color)

(56) References Cited

FOREIGN PATENT DOCUMENTS

| | | |
|---|---|---|
| EP | 1576182 A2 | 9/2005 |
| EP | 2138571 A1 | 12/2009 |
| EP | 2420563 A1 | 2/2012 |
| EP | 2878664 A1 | 6/2015 |
| JP | 62-171680 A | 7/1987 |
| JP | 63-209581 A | 8/1988 |
| JP | 07-107970 A | 4/1995 |
| JP | 08-023893 A | 1/1996 |
| JP | 08-140673 A | 6/1996 |
| JP | 11-187867 A | 7/1999 |
| JP | 2001-128660 A | 5/2001 |
| JP | 2004-236553 A | 8/2004 |
| JP | 2005-060570 A | 3/2005 |
| JP | 2006-076896 A | 3/2006 |
| JP | 2006-511224 A | 4/2006 |
| JP | 2006-204292 A | 8/2006 |
| JP | 2008-011797 A | 1/2008 |
| JP | 2008-061609 A | 3/2008 |
| JP | 2009-029967 A | 2/2009 |
| JP | 2009-050194 A | 3/2009 |
| JP | 2009-540826 A | 11/2009 |
| JP | 2010-512750 A | 4/2010 |
| JP | 2010-525836 A | 7/2010 |
| JP | 2011-024423 A | 2/2011 |
| JP | 2012-065555 A | 4/2012 |
| JP | 2012-105609 A | 6/2012 |
| JP | 2012-249547 A | 12/2012 |
| RU | 2267532 C1 | 1/2006 |
| WO | WO 2003/046141 A2 | 6/2003 |
| WO | WO 2004/101774 A1 | 11/2004 |
| WO | WO 2005/028639 A2 | 3/2005 |
| WO | WO 2006/090886 A1 | 8/2006 |
| WO | WO 2008/002329 A2 | 1/2008 |
| WO | WO 2009/066468 A1 | 5/2009 |
| WO | WO 2009/137629 A2 | 11/2009 |
| WO | WO 2010/059775 A1 | 5/2010 |
| WO | WO 2010/079602 A1 | 7/2010 |
| WO | WO 2010/098079 A1 | 9/2010 |
| WO | WO 2011/002959 A1 | 1/2011 |
| WO | WO 2011/034604 A2 | 3/2011 |
| WO | WO 2013/014472 A1 | 1/2013 |
| WO | WO 2013/017905 A1 | 2/2013 |
| WO | WO 2013/144372 A1 | 10/2013 |
| WO | WO 2014/017513 A1 | 1/2014 |
| WO | WO 2015/111685 A1 | 7/2015 |

OTHER PUBLICATIONS

Bissell et al., *J. Clin. Investigation*, 79: 801-812 (Mar. 1987).
Brenner et al., *Genetics*, 77(1): 71-94 (1974).
Brophy et al., *Hepatology*, 49: 578-586 (2009).
Castro et al., *Applied Microbiology and Biotechnology*, 38: 84-90 (1992).
Champagne et al., *Food Research International*, 29(5-6): 555-562 (1996).
Fan et al., *Acta Biomaterialia*, 6: 1178-1185 (2010).
Fonkwe et al., *Food Hydrocolloids*, 17(6): 871-883 (2003).
Freyer et al., *Cytometry*, 10(6): 803-806 (1989).
Fujishige et al., *FEMS Microbiology Ecology*, 56(2): 195-206 (2006).
Furue et al., *Proc. Natl. Acad. Sci.*, 105(36): 13409-13414 (2008).
Huang et al., *International Journal of Food Science & Technology*, 39(10): 1009-1016 (2004).
Ichi et al., *Agric. Biol. Chem.*, 50(9): 2397-2399 (1986).
King et al., *Curr. Opin. Chem. Biol.*, 11(4): 394-398 (2007).
Klimanskaya et al., *Lancet*, 365: 1636-1641 (2005).
Lecluyse et al., *Critical Reviews in Toxicology*, 42(6): 501-548 (2012).
Leung et al., *Tissue Engineering*, 17(2): 165-172 (2011).
Lin et al., *Biotechnology Journal*, 3: 1172-1184 (2008).
Liu et al., *Soft Matter*, 7: 5430-5436 (2011).
Mendes, Paula M., *Chem. Soc. Rev.*, 37: 2512-2529 (2008).
Moon et al., *Chem. Soc. Rev.*, 41: 4860-4883 (2012).
Murua et al., *Journal of Controlled Release*, 132: 76-83 (2008).
Muschiol et al., *Nematology*, 9(2): 271-284 (2007).
Nickerson et al., *Food Hydrocolloids*, 17(5): 577-583 (2003).
Oliveira et al., *Tissue Engineering: Part A*, 16(1): 343-353 (2010).
Otsuji et al., *Stem Cell Reports*, 2(5): 734-745 (2014).
Pek et al., *Nature Nanotechnology*, 3: 671-675 (2008).
Sato et al., *Regenerative Medicine*, 4 (Suppl.): 96, abstract WS-5-5 (Feb. 10, 2005).
Smith et al., *J. Biomater. Appl.*, 22(3): 241-254 (2007).
Stahl et al., *Biochemical and Biophysical Research Communications*, 322: 684-692 (2004).
Takamura et al., *Int. J. Cancer*, 98: 450-455 (2002).
Van Es et al., *Molecular and Cellular Biology*, 14(4): 2419-2428 (1994).
Van Zijl et al., *World J. Hepatol.*, 2(1): 1-7 (2010).
Weathers et al., *Appl. Microbiol. Biotechnol.*, 85: 1339-1351 (2010).
Wong et al., *Journal of Dairy Science*, 61(12): 1700-1703 (1978).
Yang et al., *Proc. Natl. Acad. Sci. USA*, 76(7): 3401-3405 (1979).
Himedia Laboratories Pvt. Ltd., Product Information for Dubelco's Modified Eagle Medium (DMEM), Revision 1 (2011) [available on the internet at http://himedialabs.com/TD/AT149.pdf].
Sigma-Aldrich, Sigma Catalog Product Information for ITS Liquid Media Supplement, EC No. 231-791-2 (2015) [available on the internet at http://www.sigmaaldrich.com/catalog/product/sigma/i3146?lang=en&region=US].
Sigma-Aldrich, Sigma Catalog Product Information for Gelzan™ CM Gelrite™ Agar Substitute Gelling Agent, EC No. 275-117-5 (2015) [available on the Internet at http://www.sigmaaldrich.com/catalog/product/sigma/g1910?lang=en&region=US].
New Energy and Industrial Technology Development Organization (NEDO), "Beyond the Fusion of Academia and Industry in Japan: An Integrated System for High Quality and Large Scale Production of hPSCs and Derivative Cells," Control No. 20140000000397, Project No. P10027 (Mar. 10, 2015) [downloaded from https://app5.infoc.nedo.go.jp/disclosure/SearchResultDetail on Nov. 15, 2016].
KELCOGEL gellan gum Book, $5^{th}$ Ed., available online at URL: [http://www.appliedbioscience.com/docs/Gellan_Book_$5^{th}$_Edition.pdf] (2007).
Wako Pure Chemical Industries, Ltd., "FCeM-series Preparation kit for ES/iPS Cells," printout from online catalog at siyaku.com (downloaded from www.siyaku.com on Nov. 14, 2016).
European Patent Office, Supplementary Partial European Search Report in European Patent Application No. 13831441 (dated Dec. 21, 2015).
European Patent Office, Extended European Search Report in European Patent Application No. 13831441.4 (dated May 13, 2016).
European Patent Office, Extended European Search Report in European Patent Application No. 13823078.4 (dated Feb. 16, 2016).
Japanese Patent Office, International Search Report in International Patent Application No. PCT/JP2013/070001 (dated Oct. 15, 2013).
Japanese Patent Office, International Search Report in International Patent Application No. PCT/JP2013/072500 (dated Oct. 1, 2013).
Rule et al., "Gellan Gum as a Substitute for Agar in Leptospiral Media," *J. Clin. Microbiol.*, 23(3): 500-504 (1986).
Russian Patent Office, Official Action in Russian Patent Application No. 2015106003 (dated Jun. 14, 2017).
Corning Life Sciences, "Corning® Microplate Selection Guide for Assays and Drug Discovery" (2007) [obtained at: http://level.com.tw/html/ezcafiles/vipweb20/img/img/20297/productselectionguide_microplates11_02_cls_mp_014.pdf on Sep. 7, 2017].
Deasy et al., "Rheological evaluation of deacetylated gellan gum (Gelrite) for pharmaceutical use," *International Journal of Pharmaceutics*, 73(2): 117-123 (1991).
Chinese Patent Office, The Fourth Office Action in Chinese Patent Application No. 201380043529.5 (dated Nov. 27, 2017).
Ahearne et al., *Biomedical Materials*, 8(3): 035004 (2013).
Bodine et al., *Proc. Natl. Acad. Sci. USA*, 86(22): 8897-8901 (1989).
Coutinho et al., *Biomaterials*, 31(29): 7494-7502 (2010).
Dias et al., *Stem Cells and Development*, 20(9): 1639-1647 (2011).
Dolznig et al., *Curr. Biol.*, 12: 1076-1085 (2002).
Dreveton et al., *Journal of Fermentation and Bioengineering* 82(3): 272-276 (1996).

(56) References Cited

OTHER PUBLICATIONS

Fujimi et al., *Int. J. Hematol.*, 87: 339-350 (2008).
Giarratana et al., *Blood*, 118(19): 5071-5079 (2011).
Hiroyama et al., *PLoS One*, 3(2): e1544 (2008).
Kishimoto et al., *Journal of Controlled Release*, 133: 185-190 (2009).
Ma et al., *Proc. Natl. Acad. Sci. USA*, 105: 13087-13092 (2008).
Mountford et al., *British Journal of Haematology*, 149: 22-34 (2010).
Otani et al., "Kobunshi Zairyo o Mochiita Xhinki Sanjigen Baiyoho no Kaihatsu," *The 36th Annual Meeting of the Molecular Biology Society of Japan*, Poster 2P-0990 (Nov. 20, 2013), Int'l Search Report in PCT/JP2014/060829 (dated Jul. 1, 2014).
Watanabe et al., "The Biological Behavior of Prostate Cancer Cells in 3D Culture Systems" *Yakugaku Zasshi*, 128(1): 37-44 (2008), English abstract and JPO Office Action in JP 2014-177554 (dated Jun. 20, 2017).
Chinese Patent Office, Second Office Action and Search Report in Chinese Patent Application No. 201380043529.5 (dated Jan. 22, 2017).
European Patent Office, Extended European Search Report in European Patent Application No. 14785390.7 (dated Aug. 5, 2016).
Japanese Patent Office, Office Action in Japanese Patent Application No. 2014-177554 (dated Jun. 20, 2017).
Japanese Patent Office, International Search Report in International Patent Application No. PCT/JP2014/060829 (dated Jul. 1, 2014).
Japanese Patent Office, Written Opinion of the International Searching Authority in International Patent Application No. PCT/JP2014/060829 (dated Jul. 1, 2014).
Martinez-Padilla et al., "Steady and oscillatory shear behavior of fluid gels formed by binary mixtures of xanthan and gellan," *Food Hydrocolloids*, 18(3): 471-481 (2004).

\* cited by examiner with deacylated gellan gum    without deacylated gellan gum A: human iPS cell (253G1)

B: human ES cell (KhES-1)

hiPS cell (253G1)

hES cell (KhES-1)

xanthan gum  κ-carageenan+locust bean gum
(0.15%)  (0.05%)+(0.05%)

HepG2 cell sphere laminin-coated GEM alginic acid bead collagen gel capsule rice callus floating culture Hela cells (photographed on day 8)

negative control      deacylated gellan gum 0.015%

A549 cells, HCT116 cells (photographed on day 5)

negative control      deacylated gellan gum

A549

HCT116 human primary hepatocytes (photographed 4 hr later)

negative control    deacylated gellan gum 0.015%

Macaca fascicularis primary hepatocytes (photographed 4 hr later)

negative control    deacylated gellan gum 0.015%

MCF-7 cells (photographed on day 5)

negative control    deacylated gellan gum
                            0.015%

A375 cell, MNNG/HOS cell (photographed on day 4)

negative control    deacylated gellan gum
                            0.015%

A375 cell

MNNG/HOS cell

MIAPaCa-2 cells (photographed on day 4)

negative control          deacylated gellan gum
                                 0.015%

CULTURE MEDIUM COMPOSITION AND METHOD OF CULTURING CELL OR TISSUE USING THEREOF

CROSS-REFERENCE TO RELATED APPLICATIONS

This patent application is a continuation of U.S. patent application Ser. No. 13/949,310, filed on Jul. 24, 2013, which claims the benefit of U.S. Provisional Patent Application No. 61/675,133 filed on Jul. 24, 2012, U.S. Provisional Patent Application No. 61/731,824 filed on Nov. 30, 2012, and U.S. Provisional Patent Application No. 61/759,172 filed on Jan. 31, 2013, each of which is incorporated by reference in its entirety herein.

TECHNICAL FIELD

The present invention relates to a medium composition containing a structure capable of suspending cells or tissues, and a method of culturing cells or tissues by using the medium composition. The medium composition and cell culture method using same of the present invention can be preferably utilized for cultivating cells and/or tissues of an animal or plant particularly in a suspension state.

BACKGROUND ART

In recent years, techniques for proliferating or maintaining in vitro various organs, tissues and cells that play distinct roles in the body of animals and plants have been developed. Proliferation or maintenance of the organs and tissues in vitro is called organ culture and tissue culture, respectively, and proliferating, differentiating or maintaining in vitro the cells separated from an organ or tissue is called cell culture. Cell culture is a technique for proliferating, differentiating or maintaining separated cells in vitro in a medium, and is indispensable for detailed analyses of the in vivo function and structure of various organs, tissues and cells. In addition, the cells and/or tissues cultured by the technique are utilized in various fields for efficacy and toxicity evaluation of chemical substances, pharmaceutical products and the like, large-scale production of useful substances such as enzymes, cell growth factors, antibodies and the like, regenerative medicine supplementing organ, tissue and cell that were lost by disease and deficiency, improvement of plant brand, production of gene recombinant products, and the like.

Animal-derived cells are broadly divided into non-adherent cells and adherent cells based on the properties thereof. Non-adherent cells are cells that do not require a scaffold for growth and proliferation, and adherent cells are cells that require a scaffold for growth and proliferation. Most of the cells constituting the living body are the latter, adherent cells. As culture methods of adherent cells, single layer culture, dispersion culture, embedded culture, microcarrier culture, sphere culture and the like are known.

Single layer culture is a method of cultivating the object cell as a single layer by using, as a scaffold, a culture container made of glass or a synthetic polymer material that underwent various surface treatments, or supportive cells called feeder cells, and is most generally prevalent. For example, culture methods using culture containers of various shapes or properties such as polystyrene applied with various surface treatments (plasma treatment, corona treatment etc.), coated with cell adhesion factors such as collagen, fibronectin, polylysine and the like, or plated with feeder cells in advance and the like have been developed. However, the single layer culture is problematic in that cells cannot maintain the specific functions they have in vivo for a long term, since the two-dimensional culture environment thereof is completely different from the in vivo environment, the cells cannot reconstruct a tissue similar to that in vivo, it is not suitable for a mass culture of cells since the cell number per a constant area is limited, and the like (patent document 1). In addition, a method of cultivating the object cell on feeder cells sometimes faces a problem in separation of the object cells from the feeder cells (non-patent document 1).

Dispersion culture is a method of cultivating adherent cells in a suspended state, which includes seeding the cells in a medium, and stirring the culture medium in a culture container applied with a surface treatment for inhibiting cell adhesion, to inhibit attachment of the cells to the culture container. However, the adherent cells cultured by the method cannot adhere to a scaffold, and therefore, the method cannot be applied to a cell that essentially requires adhesion to a scaffold for cell proliferation. In addition, being constantly disrupted by a shear force, the cell cannot exhibit its inherent cell function, and therefore, functional cells sometimes cannot be cultivated in a large amount (non-patent document 2).

Embedded culture is a method of cultivating cells by embedding and fixing the cells in a solid or semisolid gel substrate such as agar, methylcellulose, collagen, gelatin, fibrin, agarose, alginates and the like. Since the method enables three-dimensional cultivation of the cells in a state closer to in vivo and the gel substrate itself sometimes promotes proliferation and differentiation of the cells, the cells can be cultivated at high density while maintaining the function of the cell, as compared to single layer culture and dispersion culture (patent documents 2, 3). Furthermore, a method of cultivating cells, including forming a microcapsule with a size of 100-300 μm by embedding the cells in the gel substrate, and cultivating the cells in an aqueous solution medium while dispersing the microcapsule has also been developed (non-patent document 3). However, these methods have problems in that successive observation of cultured cells is not possible unless a visible light permeates the gel substrate, recovery of cells from the medium requires a complicated operation that damages the cells such as an enzyme treatment (e.g., collagenase treatment in the case of collagen gel) and the like, since the medium and microcapsule containing a gel substrate have high viscosity, medium exchange necessary for long-term cultivation is difficult and the like. In recent years, techniques enabling cell recovery from a gel substrate by a treatment with heat, shear force and the like have been developed. However, the heat, shear force and the like may exert an adverse effect on the cell function, and the safety of the gel substrate for the living body has not been clarified yet (patent documents 4, 5, non-patent documents 4, 5, 6, 7). In addition, a sol food for preventing precipitation and floating of a particulate food such as fruit, vegetable and the like cut small to keep the food uniformly dispersed and suspended has been developed in the food field. However, the sol food does not consider recovery of the dispersed particulate food, and whether the cells and tissues can be subjected to suspension culture has not been examined (patent document 6).

Microcarrier culture is a method of cultivating cells in a suspended state by proliferating cells in a single layer on the surface of a fine particle slightly heavier than water (hereinafter to be also referred to as a microcarrier), and stirring the fine particles in a culture container such as a flask and the like. Generally, the microcarrier used for the method is a spherical particle having diameter 100-300 μm, surface area 3000-6000 $cm^2/g$, specific gravity 1.03-1.05, and is composed of a material such as dextran, gelatin, alginic acid, polystyrene and the like. Collagen, gelatin, or a charged group such as dimethylaminoethyl and the like may also be provided to the surface of a microcarrier to facilitate attachment of the cell. This method is applied to a mass culture of a cell since it can markedly increase the culture area (patent documents 7, 8). However, it is difficult to attach the object cell almost uniformly to all microcarriers, and problems occur such as detachment of the cells from the microcarrier due to a shear force during stirring, damage on the cells and the like (non-patent document 8).

Sphere culture is a culture method including forming an aggregate composed of several dozen—several hundred object cells (hereinafter to be also referred to as a sphere), and culturing the aggregates with standing or shaking in a medium. It is known that a sphere has a high cell density, reconstructs cell-cell interactions and cell structure close to those in the in vivo environment, and can be cultured while maintaining the cell function for a longer term as compared to a single layer culture and a dispersion culture method (non-patent documents 9, 10). However, the sphere culture cannot form a large sphere, since supply of nutrition inside the sphere and discharge of wastes are difficult when the size of the sphere is too large. In addition, since the formed sphere needs to be cultivated in a dispersed state on the bottom of a culture container, the number of spheres per a given volume cannot be increased with ease, and it is not suitable for a mass culture. Furthermore, as a method of forming a sphere, hanging drop culture, culture on cell non-adhesive surface, culture inside microwell, rotation culture, culture utilizing cell scaffold, coagulation by centrifugal force, ultrasonication, electric field or magnetic field and the like are known. However, these methods are problematic in that the operation is complicated, recovery of sphere is difficult, size control and large-scale production are difficult, influence on the cell is unknown, special exclusive container and apparatus are necessary and the like (patent document 9).

On the other hand, as for plants, cell, protoplast without a cell wall or organ, tissue, callus of plant such as leaf, stalk, root, growing point, seed, embryo, pollen and the like can also be grown by culture in an aseptic state. Using a culture technique for such plant tissues and cells, brand improvement of plant and production of useful substances have been made possible. As a method for proliferating plant cells and tissues in a large amount in a short time, a method of suspension cultivation of plant cells and tissues in a liquid medium is known (non-patent document 11). To achieve good proliferation thereof, supply of sufficient oxygen, maintenance of a uniform mixing state, prevention of cell damage and the like are important. The oxygen supply to a culture medium and suspending of cells and tissues may be performed by combining aeration and mechanical stirring, or aeration alone. The former may result in defective proliferation due to a damage on the cells and tissues by stirring, and the latter is problematic in that, even though shearing of cells and tissues is less, since a uniform mixing state may be difficult to maintain in high density culture, the cells and tissues form sediment to lower the proliferation efficiency and the like.

Moreover, for the research and development of an anticancer drug or selection of an appropriate anticancer drug in a cancer treatment, the anticancer activity of a medicament for cancer cells is evaluated by cultivating cancer cells in vitro in a culture medium containing a candidate drug or anticancer drug. However, the existing evaluation methods of anticancer activity have problems of a gap between in vitro evaluation results and actual clinical effects and the like. To improve the problems, methods of evaluating the activity under cell culture conditions reproducing the in vivo environment as much as possible have been developed. For example, a method including embedding cancer cells in a support such as soft agar, collagen gel, hydrogel and the like to allow for culture of the cancer cells in an environment inhibiting adhesion to a culture container, and evaluating the anticancer drug has been developed (patent document 10, non-patent documents 12, 13). In addition, a method including inhibiting cell adhesion by coating a surface of a culture container with a material inhibiting cell adhesion, or applying a special processing of the surface, culturing cancer cells in a coagulated state (sphere culture), and evaluating the anticancer activity has been developed (patent documents 11, 12).

However, those cancer cell culture methods have various problems in that the production process of a culture container and an operation for cell culture are complicated, an operation for recovery of the cell from a support such as collagen and the like followed by evaluation of anticancer activity is complicated, supply of support is sometimes limited when the support is an animal-derived component, since it is expensive, cell aggregates (spheres) are associated to have an excessive size, thereby decreasing the cell survival rate and reproducibility, and the like. Moreover, when an anticancer drug is screened for, a culture method of cancer cells, which is convenient, can treat a large amount of uniform samples, and has high reproducibility, is desired.

Additionally, various activities of a pharmaceutical product candidate drug and a pharmaceutical product on hepatocytes have been evaluated by cultivating hepatocytes in vitro in a culture medium containing the pharmaceutical product candidate drug or the pharmaceutical product. However, since the function inherently exhibited by hepatocytes in vivo may be lost by cultivating the hepatocytes in vitro, existing hepatocyte culture methods have problems in that a precise evaluation of a pharmaceutical product candidate drug and a pharmaceutical product is not available, evaluation of many samples is difficult and the like. To overcome such problems, a method of performing activity evaluation under cell culture conditions reproducing the in vivo environment as much as possible has been developed. For example, a method including culturing hepatocytes on an extracellular matrix such as collagen, laminin, Matrigel (registered trade mark) and the like, maintaining the function of hepatocytes has been developed (patent document 13, non-patent documents 14, 15). In addition, a method including forming an aggregate (sphere) of hepatocytes by treatments, for example, inhibiting cell adhesion by coating a surface of a culture container with a material inhibiting cell adhesion or applying a special processing of the surface of a container, vibrating a culture container and the like, thereby to maintain the function of the hepatocytes has been developed (patent documents 14, 15, non-patent documents 16, 17).

However, those hepatocyte culture methods have various problems in that the production process of a culture container and an operation for cell culture are complicated, an operation for recovery of the cell from a support such as collagen and the like and evaluation of the function of hepatocytes is complicated, supply of support is sometimes limited when the support is an animal-derived component, since it is expensive, cell aggregates (spheres) are associated to have an excessive size, thereby decreasing the cell survival rate and reproducibility, and the like. Moreover, when a pharmaceutical product candidate drug or a pharmaceutical product is screened for, a culture method of hepatocytes, which is convenient, can treat a large amount of uniform samples, and has high reproducibility, is desired.

DOCUMENT LIST

Patent Documents

[patent document 1] JP-A-2001-128660
[patent document 2] JP-A-S62-171680
[patent document 3] JP-A-S63-209581
[patent document 4] JP-A-2009-29967
[patent document 5] JP-A-2005-60570
[patent document 6] JP-A-8-23893
[patent document 7] JP-A-2004-236553
[patent document 8] WO2010/059775
[patent document 9] JP-A-2012-65555
[patent document 10] JP-A-2008-11797
[patent document 11] JP-A-2008-61609
[patent document 12] JP-A-2012-249547
[patent document 13] WO2005/028639
[patent document 14] WO2010/079602
[patent document 15] JP-A-2009-50194

Non-Patent Documents

[non-patent document 1] Klimanskaya et al., Lancet 2005, 365:1636-1641
[non-patent document 2] King et al., Curr Opin Chem Biol. 2007, 11:394-398
[non-patent document 3] Murua et al., J. of Controlled Release 2008, 132:76-83
[non-patent document 4] Mendes, Chemical Society Reviews 2008, 37:2512-2529
[non-patent document 5] Moon et al., Chemical Society Reviews 2012, 41:4860-4883
[non-patent document 6] Pek et al., Nature Nanotechnol. 2008, 3:671-675
[non-patent document 7] Liu et al., Soft Matter 2011, 7:5430-5436
[non-patent document 8] Leung et al., Tissue Engineering 2011, 17:165-172
[non-patent document 9] Stahl et al., Biochem. Biophys. Res. Comm. 2004, 322:684-692
[non-patent document 10] Lin et al., Biotechnol J. 2008, 3:1172-1184
[non-patent document 11] Weathers et al., Appl Microbiol Biotechnol 2010, 85:1339-1351
[non-patent document 12] Takamura et al., Int. J. Cancer 2002, 98: 450-455
[non-patent document 13] Yang et al., Proc. Natl. Acad. Sci. USA 1979, 76: 3401-3405
[non-patent document 14] Bissell et al., J. Clin. Invest. 1987, 79: 801-812
[non-patent document 15] LeCluyse et al., Critical Reviews in Toxicology 2012, 42:501-548
[non-patent document 16] Brophy et al., Hepatology 2009, 49:578-586
[non-patent document 17] Franziska et al., World J Hepatol 2010, 2:1-7

SUMMARY OF THE INVENTION

Problems to be Solved by the Invention

An object of the present invention is to solve the above-mentioned problems of the prior art, and provide a medium composition for cultivating cells and/or tissues of an animal or plant particularly in a three-dimensional or suspended state, and a method of culturing cells and/or tissues of an animal or plant by using the medium composition.

Also, an object of the present invention is to solve the above-mentioned problems of the prior art, and provide a medium composition for cultivating a cell aggregate (sphere) of cancer cells in a three-dimensional environment and a test method of cancer cell by using the medium composition.

Alternatively, an object of the present invention is to solve the above-mentioned problems of the prior art, and provide a medium composition for cultivating a cell aggregate (sphere) of hepatocytes in a three-dimensional environment and a test method of cancer cell by using the medium composition.

Furthermore, an object of the present invention is to provide a medium additive that promotes proliferation of cancer cell in culturing the cancer cell and a medium additive that suppresses a decrease in the number of hepatocytes in culturing the hepatocytes.

Means of Solving the Problems

The present inventors have conducted intensive studies of various compounds and the effect of suspending cells and/or tissues in a liquid medium containing them and succeeded in finding a structure capable of uniformly dispersing cells and/or tissues in a suspended state without substantially increasing the viscosity of the liquid medium. They have found that cells and/or tissues can be proliferated, differentiated or maintained while keeping the suspended state, by using a medium composition containing at least said structure. Moreover, they have also found that cultured cells and/or tissues can be easily recovered from the medium composition, which resulted in the completion of the present invention.

The present inventors have also conducted intensive studies of the effect of various compounds and liquid media containing same on cancer cell aggregate (sphere), and succeeded in finding a medium composition that prevents association of the spheres and affords uniform dispersion. They have found that the sphere can be cultivated with a high survival rate and the activity of an anticancer drug against a cancer cell can be evaluated efficiently and with good sensitivity by using the medium composition. Moreover, they have also found that a cultured sphere can be easily recovered from the medium composition and evaluated, which resulted in the completion of the present invention.

Also, the present inventors have conducted intensive studies of the effect of various compounds and liquid media containing same on hepatocyte aggregate (sphere), and succeeded in finding a medium composition that prevents association of the spheres and affords uniform dispersion. They have found that the sphere can be cultivated with a high survival rate while maintaining the function of hepatocytes and the effect of a pharmaceutical product candidate drug or pharmaceutical product on the hepatocytes can be evaluated efficiently and with good sensitivity by using the medium composition. Moreover, they have also found that cultured spheres can be easily recovered from the medium composition and evaluated, which resulted in the completion of the present invention.

Furthermore, the present inventors have found that the proliferation of cancer cell can be markedly promoted by adding a deacylated gellan gum or a salt thereof to a medium containing the cancer cell, which resulted in the completion of the present invention.

In addition, the present inventors have found that a decrease in the number of hepatocytes can be suppressed by adding a deacylated gellan gum or a salt thereof to a medium containing the hepatocytes, which resulted in the completion of the present invention.

Accordingly, the present invention provides the following:

(1) A medium composition comprising a structure capable of culturing cells or tissues by suspending them.
(2) The medium composition of (1), permitting an exchange treatment of the medium composition during culture and recovery of the cells or tissues after completion of the culture.
(3) The medium composition of (1), which does not require any of a temperature change, a chemical treatment, an enzyme treatment and a shear force, during recovery of the cells or tissues from the medium composition.
(4) The medium composition of (1), having a viscosity of not more than 8 mPa·s.
(5) The medium composition of (1), wherein the aforementioned structure has a size that passes a filter having a pore size of 0.2 μm to 200 μm when it is passed through a filter.
(6) The medium composition of (1), wherein the aforementioned structure contains a polymer compound.
(7) The medium composition of (6), wherein the aforementioned polymer compound includes a polymer compound having an anionic functional group.
(8) The medium composition of (6), wherein the aforementioned polymer compound is a polysaccharide.
(9) The medium composition of (7), wherein the aforementioned anionic functional group is at least one kind selected from the group consisting of a carboxy group, a sulfo group and a phosphate group.
(10) The medium composition of (8), wherein the aforementioned polysaccharide is at least one kind selected from the group consisting of hyaluronic acid, gellan gum, deacylated gellan gum, rhamsan gum, diutan gum, xanthan gum, carageenan, fucoidan, pectin, pectic acid, pectinic acid, heparan sulfate, heparin, heparitin sulfate, keratosulfate, chondroitin sulfate, dermatan sulfate, rhamnan sulfate and a salt thereof.
(11) The medium composition of (10), wherein the aforementioned polysaccharide is at least one kind selected from the group consisting of hyaluronic acid, deacylated gellan gum, diutan gum, xanthan gum, carageenan and a salt thereof.
(12) The medium composition of (10) or (11), wherein the aforementioned polysaccharide is deacylated gellan gum or a salt thereof.
(13) The medium composition of (12), wherein a final concentration of the aforementioned deacylated gellan gum or a salt thereof in the medium composition is 0.001-1.0% (weight/volume).
(14) The medium composition of (13), further comprising a polysaccharide other than deacylated gellan gum or a salt thereof.
(15) The medium composition of (14), wherein the aforementioned polysaccharide is at least one kind selected from the group consisting of xanthan gum, alginic acid, carageenan, diutan gum and a salt thereof.
(16) The medium composition of (14), wherein the aforementioned polysaccharide is at least one kind selected from the group consisting of methylcellulose, locust bean gum and a salt thereof.
(17) The medium composition of any one of (1) to (16), further comprising a metal ion.
(18) The medium composition of (17), wherein the aforementioned metal ion is a divalent metal ion.
(19) The medium composition of (18), wherein the aforementioned metal ion is at least one kind selected from the group consisting of a calcium ion, a magnesium ion, a zinc ion, a ferrous ion and a copper ion.
(20) The medium composition of (19), wherein the aforementioned metal ion is a calcium ion.
(21) The medium composition of (20), further comprising a metal ion other than a calcium ion.
(22) The medium composition of (21), wherein the aforementioned metal ion is at least one kind selected from the group consisting of a magnesium ion, a sodium ion and a potassium ion.
(23) The medium composition of any one of (1) to (22), further comprising an extracellular matrix and/or a cell adhesion molecule.
(24) The medium composition of (23), wherein the aforementioned extracellular matrix is at least one kind selected from the group consisting of collagen, hyaluronic acid and proteoglycan.
(25) The medium composition of (23), wherein the aforementioned cell adhesion molecule is at least one kind selected from the group consisting of cadherin, laminin, fibronectin and vitronectin.
(26) The medium composition of any one of (1) to (25), which is for cell culture.
(27) The medium composition of (26), wherein the aforementioned cell is an adherent cell or a non-adherent cell.
(28) The medium composition of (27), wherein the aforementioned adherent cell is attached to a microcarrier.
(29) The medium composition of (27), wherein the aforementioned adherent cell is embedded in a carrier.
(30) The medium composition of (27), wherein the aforementioned adherent cell is a sphere.
(31) The medium composition of (27), wherein the aforementioned adherent cell is selected from the group consisting of a pluripotent stem cell, a cancer cell and a hepatocyte.
(32) A cell or tissue culture comprising the medium composition of any one of (1) to (31) and cells or tissues.
(33) A method of culturing a cell or tissue, comprising cultivating the cell or tissue in the medium composition of any one of (1) to (31).
(34) The culture method of (33), wherein the aforementioned cell is selected from the group consisting of a pluripotent stem cell, a cancer cell and a hepatocyte.
(35) A method of recovering a cell or tissue, comprising separating the cell or tissue from the culture of (32).
(36) The recovery method of (35), wherein the aforementioned separation is performed by filtration, centrifugation or magnetic separation.
(37) A method of producing a sphere, comprising cultivating an adherent cell in the medium composition of any one of (1) to (31).
(38) A method of screening for an anticancer drug, comprising
(a) a step of cultivating a cancer cell in the presence of a test substance and in the absence thereof in the medium composition of any one of claims 1 to 31, and
(b) a step of analyzing changes in the proliferation of the cancer cell.
(39) The method of (38), further comprising a step of selecting, as a candidate substance, a substance that suppresses the proliferation of the cancer cell than in the absence of the test substance.

(40) A method of screening for a pharmaceutical product candidate substance that acts on hepatocytes, comprising
(a) a step of cultivating hepatocytes in the presence of a test substance and in the absence thereof in the medium composition of any one of claims 1 to 31, and
(b) a step of analyzing changes in the physiological function of the hepatocytes.
(41) The method of (40), further comprising a step of selecting, as a candidate substance, a substance that suppresses or increases the physiological function of the hepatocytes than in the absence of the test substance.
(42) A method of evaluating the efficacy or toxicity of a pharmaceutical product candidate substance that acts on hepatocytes, comprising
(a) a step of cultivating hepatocytes in the presence of a test substance and in the absence thereof in the medium composition of any one of claims 1 to 31, and
(b) a step of analyzing changes in the physiological function of the hepatocytes.
(43) A medium additive for preparing a medium composition capable of culturing cells or tissues by suspending them, comprising a polymer compound dissolved or dispersed in a solvent.
(44) The medium additive of (43), which is in a sterilized state.
(45) The medium additive of (43) or (44), wherein the aforementioned polymer compound is a polymer compound having an anionic functional group.
(46) The medium additive of (43) or (44), wherein the aforementioned polymer compound is a deacylated gellan gum or a salt thereof.
(47) A method of producing a medium composition capable of culturing cells or tissues by suspending them, comprising mixing a polymer compound and a medium.
(48) The method of (47), comprising mixing the medium additive of any one of (43) to (46) and a medium.
(49) The method of (48), wherein the aforementioned medium is dissolved or dispersed in a solvent.
(50) The method of (47), wherein the aforementioned polymer compound is a polymer compound having an anionic functional group.
(51) The method of (50), wherein the aforementioned polymer compound is deacylated gellan gum or a salt thereof.
(52) The method of (47), wherein the aforementioned polymer compound and the medium are mixed with water.
(53) The method of (52), comprising heating at 80-130° C. after mixing with water.
(54) The method of (53), comprising heating at 100-125° C.
(55) The method of (47), comprising filtration sterilization.
(56) The method of (55), wherein the aforementioned filtration sterilization includes passage through a 0.1-0.5 µm filter.
(57) An additive for a medium for cancer cells, comprising deacylated gellan gum or a salt thereof, or diutan gum or a salt thereof.
(58) The additive of (57) that promotes proliferation of a cancer cell in culturing the cancer cell.
(59) The additive of (57), which is used for evaluating the anticancer activity of an anticancer drug.
(60) A medium composition for cancer cells, comprising the additive of any one of (57) to (59).
(61) A method of culturing a cancer cell, comprising cultivating the cancer cell in the presence of the additive of any one of (57) to (59), or in the medium composition of (60).
(62) A method of evaluating the activity of an anticancer drug to a cancer cell, comprising cultivating the cancer cell in the presence of the additive of any one of (57) to (59), or in the medium composition of (60).
(63) The method of (61) or (62), wherein the cancer cells form a cell aggregate in the medium composition for the cancer cell.
(64) The method of (61) or (62), wherein a culture container for cultivating the cancer cell suppresses attachment of the cancer cell.
(65) An additive for a medium for hepatocytes, comprising deacylated gellan gum or a salt thereof, or diutan gum or a salt thereof.
(66) The additive of (65), which suppresses a decrease in the number of hepatocytes in culturing the hepatocytes.
(67) The additive of (65), which is used for evaluating the effect of a pharmaceutical product and a pharmaceutical product candidate drug on hepatocytes.
(68) A medium composition for hepatocytes, comprising the additive of any one of (65) to (67).
(69) A method of evaluating the activity of a pharmaceutical product and a pharmaceutical product candidate drug to hepatocytes, comprising cultivating the hepatocytes in the presence of the additive of any one of (65) to (67), or in the medium composition of (68).
(70) The method of (69), wherein the hepatocytes form a cell aggregate in the medium composition for hepatocytes.
(71) The method of (69), wherein a culture container for cultivating hepatocytes suppresses attachment of the hepatocyte.

Effects of the Invention

The present invention provides a medium composition containing a structure of a particular compound (hereinafter to be also referred to as a particular compound), particularly a polymer compound having an anionic functional group. Using the medium composition, cells and/or tissues can be cultivated in a suspended state without an operation such as shaking, rotation and the like having a risk of causing injury and loss of functions of cells and tissues. Furthermore, using the medium composition, the medium can be exchanged easily during culture, and the cultured cells and/or tissues can also be recovered easily. The present invention applies the culture method to the cells and/or tissues collected from an animal body or a plant body, and can prepare the object cells and/or tissues in a large amount without impairing the functions thereof. The cells and/or tissues obtained by the culture method can be utilized when performing efficacy and toxicity evaluation of chemical substances, pharmaceutical products and the like, large-scale production of useful substances such as enzymes, cell growth factors, antibodies and the like, regenerative medicine for supplementing organ, tissue and cell that were lost by disease and deficiency, and the like. Particularly, a medium composition prepared by using deacylated gellan gum is superior, and has the following characteristics. Since the concentration for expressing the property is extremely low (one order or so lower), an influence on the medium component can be suppressed to the minimum. Since lump is not easily formed when dissolved in water, large-scale production does not easily cause trouble. Furthermore, since the viscosity in the concentration range where the property is expressed is low, the operability such as recovery of cells and/or tissues and the like is extremely good.

In addition, using the medium composition of the present invention, association of the cancer cell aggregates (spheres) can be suppressed, and the sphere can be cultivated in a dispersed state, and therefore, the proliferation of cancer cell can be promoted. Moreover, when an anticancer drug is evaluated using the medium composition, the anticancer drug can be easily added to a medium, and a detection reagent for evaluating cell proliferation can be easily added. In addition, since the cultured cancer cells can be recovered, a function evaluation of the recovered cells can also be easily performed. The present invention can be preferably utilized when performing efficacy evaluation of and screening for a chemical substance, an anticancer drug and the like with cancer cells obtained by the culture method.

When cultivated in the medium composition of the present invention, since an influence from the non-in vivo environment in two-dimensional culture is small and only an adhesion between cells occurs, the sensitivity of HB-EGF (heparin binding epidermal growth factor-like growth factor) that promotes canceration becomes high in cancer cells, and the sensitivity to an EGF receptor inhibitor at the downstream thereof can be enhanced. Furthermore, the sensitivity to inhibitors of MEK and Akt, which are important signal transduction pathways for cancer cell scaffold-independent proliferation, can also be enhanced.

Alternatively, using the medium composition of the present invention, association of hepatocyte aggregates (spheres) can be suppressed, and the spheres can be cultivated in a dispersed state. Therefore, the survival and cell function of hepatocytes can be maintained in vitro. Furthermore, when evaluation of a pharmaceutical product candidate drug or a pharmaceutical product is performed using the medium composition, the pharmaceutical product candidate drug or pharmaceutical product can be easily added to the medium, and a detection reagent for evaluation of cell function can be added easily. Since cultured hepatocytes can be recovered, a functional evaluation of the recovered cells can be performed easily. The present invention can be preferably utilized when performing efficacy and toxicity evaluation and screening for a chemical substance, an anticancer drug and the like with hepatocytes obtained by the culture method.

Moreover, the medium additive of the present invention containing deacylated gellan gum or a salt thereof can markedly promote the proliferation of cancer cells when culturing the cancer cells.

Also, the medium additive of the present invention containing deacylated gellan gum or a salt thereof can suppress a decrease in the number of hepatocytes when culturing the hepatocytes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Figure 1:
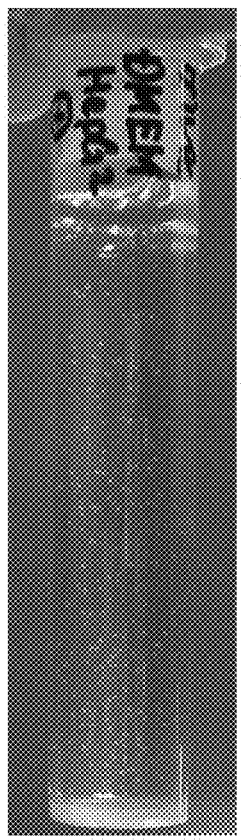
FIG. 1 is a Figure showing that, when spheres of HepG2 cells were cultured in the medium composition of the present invention, the spheres were uniformly dispersed and could be cultured in a suspended state.

The present invention is explained in more detail in the following.

The terms used in the present specification are defined as follows.

The cell in the present invention is a most basic unit constituting animals and plants, which has, as its elements, cytoplasm and various organelles inside the cellular membrane. In this case, the nucleus encapsulating the DNA may or may not be contained intracellularly. For example, the animal-derived cells in the present invention include reproductive cells such as spermatozoon, oocyte and the like, somatic cells constituting the living body, stem cells (pluripotent stem cells etc.), progenitor cells, cancer cells separated from the living body, cells separated from the living body, which acquired immortalizing ability and is maintained stably in vitro (cell line), cells separated from the living body and applied with artificial genetic modification, cells separated from the living body wherein the nucleus is artificially exchanged, and the like. Examples of the somatic cells constituting the living body include, but are not limited to, fibroblast, bone marrow cells, B lymphocytes, T lymphocytes, neutrophils, red blood cells, platelets, macrophages, monocytes, osteocytes, bone marrow cells, pericytes, dendritic cells, keratinocytes, adipocytes, mesenchymal cells, epithelial cells, epidermal cells, endothelial cells, vascular endothelial cells, hepatocytes, chondrocytes, cumulus cells, nerve system cells, glial cells, neurons, oligodendrocytes, microglial, astrocytes, heart cells, esophagus cells, myocytes (e.g., smooth muscle cells or skeletal muscle cells), pancreas beta cells, melanin cells, hematopoietic progenitor cells (e.g., cord blood derived CD34 positive cells), mononuclear cells and the like. The somatic cells include cells collected from any tissue, for example, skin, kidney, spleen, adrenal gland, liver, lung, ovary, pancreas, uterus, stomach, colon, small intestine, large intestine, bladder, prostate, testis, thymus, muscle, bond tissue, bone, joints, blood vessel tissue, blood (including cord blood), bone marrow, heart, eye, brain, nerve tissue and the like. Stem cells are cells concurrently having an ability to replicate itself, and an ability to differentiate into other plural lineages. Examples thereof include, but are not limited to, embryonic stem cells (ES cell), embryonic tumor cells, embryonic reproductive stem cells, artificial pluripotent stem cells (iPS cell), neural stem cells, hematopoietic stem cells, mesenchymal stem cells, liver stem cells, pancreas stem cells, muscle stem cells, reproductive stem cells, intestinal stem cells, cancer stem cells, hair follicle stem cells and the like. Examples of the pluripotent stem cells include ES cells, embryonic reproductive stem cells and iPS cells, from among the aforementioned stem cells. Progenitor cells are cells on the way to differentiate from the afore-mentioned stem cell into a particular somatic cell or reproductive cell. Cancer cells are cells that are derived from a somatic cell and have acquired infinite proliferative capacity. Cell lines are cells that have acquired infinite proliferative capacity by an artificial operation in vitro.

Examples of the cancer tissue include, but are not limited to, tissues from gastric cancer, esophagus cancer, large intestine cancer, colon cancer, rectal cancer, pancreatic cancer, breast cancer, ovarian cancer, prostate cancer, flat epithelial cell cancer, basal cell carcinoma, adenocarcinoma, bone marrow cancer, kidney cell cancer, urinary duct cancer, liver cancer, cholangiocarcinoma, cervical cancer, endometrial cancer, testis cancer, small cell lung cancer, non-small cell lung cancer, bladder cancer, epithelial cancer, craniopharyngioma, laryngeal cancer, tongue cancer, fiber sarcoma, mucosa sarcoma, liposarcoma, chondrosarcoma, osteogenic sarcoma, chordoma, blood vessel sarcoma, lymphangiosarcoma, lymphangioendothelial sarcoma, synovial sarcoma, mesothelioma, Ewing's tumor, leiomyosarcoma, rhabdomyosarcoma, seminoma, Wilms' tumor, glioma, astrocytoma, bone marrow sarcoma, meningioma, melanoma, neuroblastoma, medulloblastoma, retina blastoma, malignant lymphoma, and blood derived from cancer patients and the like. Examples of the cancer cell line include, but are not limited to, HBC-4, BSY-1, BSY-2, MCF-7, MCF-7/ADR RES, HS578T, MDA-MB-231, MDA-MB-435, MDA-N, BT-549, T47D as human breast cancer cell lines, HeLa as human cervical carcinoama cell line, A549, EKVX, HOP-62, HOP-92, NCI-H23, NCI-H226, NCI-H322M, NCI-H460, NCI-H522, DMS273, DMS114 as human lung cancer cell line, Caco-2, COLO-205, HCC-2998, HCT-15, HCT-116, HT-29, KM-12, SW-620, WiDr as human large intestine cancer cell line, DU-145, PC-3, LNCaP as human prostate cancer cell line, U251, SF-295, SF-539, SF-268, SNB-75, SNB-78, SNB-19 as human central nervous system cancer cell line, OVCAR-3, OVCAR-4, OVCAR-5, OVCAR-8, SK-OV-3, IGROV-1 as human ovarian cancer cell line, RXF-631L, ACHN, U0-31, SN-12C, A498, CAKI-1, RXF-393L, 786-0, TK-10 as human kidney cancer cell line, MKN45, MKN28, St-4, MKN-1, MKN-7, MKN-74 as human gastric cancer cell line, LOX-IMVI, LOX, MALME-3M, SK-MEL-2, SK-MEL-5, SK-MEL-28, UACC-62, UACC-257, M14 as skin cancer cell line, CCRF-CRM, K562, MOLT-4, HL-60 TB, RPMI8226, SR, UT7/TPO, Jurkat as leukemia cell line, A431 as human epithelial like cancer cell line, A375 as human melanoma cell line, MNNG/HOS as human osteosarcoma cell line, MIAPaCa-2 as human pancreatic cancer cell line, and the like. Examples of the cell line include, but are not limited to, HEK293 (human embryonic kidney cell), MDCK, MDBK, BHK, C-33A, AE-1, 3D9, Ns0/1, NIH3T3, PC12, S2, Sf9, Sf21, High Five (registered trade mark), Vero and the like.

Examples of the hepatocytes in the present invention include primary hepatocytes collected from liver tissue, hepatocyte strain established by passage culture under conditions optimized for in vitro culture, and hepatocytes differentiated and induced in vitro from cells derived from a tissue other than the liver, pluripotent stem cells such as iPS cells, ES cells and the like, mesenchymal stem cells, stem cells derived from peripheral blood, myeloid stem cells, adipose stem cells, liver stem cells, liver progenitor cells, and the like. The liver tissue is a liver collected from human, rat, mouse, guinea pig, hamster, rabbit, swine, bovine, horse, dog, cat, monkey etc., which may be a normal liver or a cancerated liver. While the primary hepatocytes can be separated and recovered from such liver by a perfusion method using collagenase, it may be purchased from reagent companies such as Primarycell, Japan Becton Dickinson and Company, Takara Bio Inc., Hokkaido System Science Co., Ltd., Lonza Japan, Veritas Ltd., Life Technologies Japan Corporation and the like. The purchased hepatocytes may be in a frozen state or attached to a carrier such as collagen and the like. Examples of the hepatocyte cell lines include, but are not limited to, HepG2, Hep3B, HepaRG (registered trade mark), JHH7, HLF, HLE, PLC/PRF/5, WRL68, HB611, SK-HEP-1, HuH-4, HuH-7 and the like.

While the function of the hepatocytes in the present invention is not particularly limited, it includes expression of the activity of cytochrome P450 (also referred to as CYP) such as CYP1A1, CYP1A2, CYP2A6, CYP2B6, CYP2C8, CYP2C9, CYP2C19, CYP2D6, CYP2E1, CYP3A4, CYP3A5 and the like and metabolism of pharmaceutical products and the like by these enzymes, conjugation of pharmaceutical products and the like by glucuronic acid, glutathione, sulfuric acid, glycine and the like, production of useful proteins such as albumin, apolipoproteins, thrombopoietin and the like, secretion of bilirubin, synthesis of urea, synthesis of bile acid and fatty acid, transport of pharmaceutical products and the like by transporters, and the like. In the embodiment of the present invention, the hepatocytes preferably maintains, from the above-mentioned functions, activity of cytochrome P450, production of albumin and/or transport of pharmaceutical products and the like by transporters (for example, uptake of Carboxydichlorofluorescein diacetate, Tetraethylammonium Bromide, Taurocholate, Rosvastatin and excretion of Carboxydichlorofluorescein).

The pharmaceutical products in the present invention include any substance applied to medical use. The pharmaceutical product candidate drug is a substance which has been the subject of search or development and research as a candidate for a pharmaceutical product, and includes synthesis compound, protein, nucleic acid, saccharides, naturally occurring substance and the like.

The anticancer drug in the present invention includes medicaments that directly act on the cancer cells and suppress proliferation and function of the cancer cell, as well as medicaments that do not directly act on the cancer cell but suppress proliferation or function of the cancer cell, or kill the cancer cell by a collaborative action with immunocyte in vivo or other medicaments. Examples of the anticancer drug include, but are not limited to, alkylating agent, platinum derivative, metabolic antagonist represented by 5-FU's anticancer drug, topoisomerase inhibitor, microtubule inhibitor, anticancer antibiotic represented by epirubicin, molecular target drug represented by gefitinib, trastuzumab, cetuximab, erlotinib, panitumumab, lapatinib, temsirolimus, everolimus, ipilimumab, vandetanib, crizotinib, ruxolitinib, trametinib, and the like. Examples of the target molecule of the molecular target drug include, but are not limited to, various kinases, Her2, EGFR (epidermal growth factor receptor), PI3K (phosphatidyl inositol 3-kinase), mTOR (mammals rapamycin target protein), Akt, CDK (cyclin dependent kinase), VEGFR (vascular endothelial cell proliferation factor receptor), PDGFR (platelet-derived growth factor receptor), FGFR (fibroblast growth factor receptor), c-Met, Raf, p38 MAPK, CTLA-4, ALK, JAK, MEK (MAPK/ERK kinase), Hsp90, histone deacetylase and the like. Furthermore, synthetic compounds, proteins, nucleic acids, saccharides, natural products to be the candidates for medicaments having such effects are also included in the anticancer drug in the present invention.

The plant-derived cell in the present invention also includes cells separated from each tissue of a plant body, as well as a protoplast obtained by artificially removing the cell wall from the cell.

The tissue in the present invention is a unit of a structure which is an assembly in a certain manner of cells having some kinds of different properties and functions, and examples of the animal tissue include epithelial tissue, bond tissue, muscular tissue, nerve tissue and the like. Examples of the plant tissue include meristem, epidermis tissue, assimilation tissue, mesophyll tissue, conductive tissue, mechanical tissue, parenchyma tissue, dedifferentiated cell cluster (callus) and the like.

When cells and/or tissues are cultivated by the method of the present invention, the cells and/or tissues to be cultivated can be selected freely from the cells and/or tissues described above and cultivated. The cells and/or tissues can be directly recovered from an animal or plant body. The cells and/or tissues may be induced, grown or transformed from an animal or plant body by applying a particular treatment and then collected. In this case, the treatment may be in vivo or in vitro. Examples of the animal include insect, fish, amphibian, reptiles, birds, pancrustacea, hexapoda, mammals and the like. Examples of the mammal include, but are not limited to, rat, mouse, rabbit, guinea pig, squirrel, hamster, vole, platypus, dolphin, whale, dog, cat, goat, bovine, horse, sheep, swine, elephant, common marmoset, squirrel monkey, Macaca mulatta, chimpanzee and human. The plant is not particularly limited as long as the collected cells and/or tissues can be applied to liquid culture. Examples thereof include, but are not limited to, plants (e.g., ginseng, periwinkle, henbane, coptis, belladonna etc.) producing crude drugs (e.g., saponin, alkaloids, berberine, scopolin, phytosterol etc.), plants (e.g., blueberry, safflower, madder, saffron etc.) producing dye or polysaccharide (e.g., anthocyanin, safflower dye, madder dye, saffron dye, flavones etc.) to be a starting material for cosmetic or food, or plants producing a pharmaceutical drug substance, plants (rice, corn, wheat or barley etc.) to be feed or food and the like.

Suspending of cells and/or tissues in the present invention refers to a state where cells and/or tissues do not adhere to a culture container (non-adhesive). Furthermore, in the present invention, when the cells and/or tissues are proliferated, differentiated or maintained, the state where the cells and/or tissues are uniformly dispersed and suspended in the liquid medium composition in the absence of a pressure on or vibration of the liquid medium composition from the outside or shaking, rotating operation and the like in the composition is referred to as "suspension standing", and cultivation of the cells and/or tissues in such condition is referred to as "suspension standing culture". In the "suspension standing", the period of suspending includes at least 5-60 min, 1 hr-24 hr, 1 day-21 days, though the period is not limited thereto as long as the suspended state is maintained.

The medium composition of the present invention is a composition containing a structure capable of culturing cells or tissues with suspending (preferably capable of suspension standing culture) and a medium.

The medium composition of the present invention is preferably a composition permitting an exchange treatment of the medium composition during culture, and recovery of the cells or tissues from the medium composition after completion of the culture. More preferably, it is a composition that does not require any of a temperature change, a chemical treatment, an enzyme treatment and a shear force during recovery of the cells or tissues from the medium composition.

The structure in the present invention is formed from a particular compound and shows an effect of uniformly suspending cells and/or tissues. More particularly, it includes an assembly of polymer compounds via an ion, a three-dimensional network formed by polymer compounds and the like. It is known that polysaccharides form a microgel via a metal ion (e.g., JP-A-2004-129596), and the structure of the present invention also includes such microgel as one embodiment.

Figure 13:
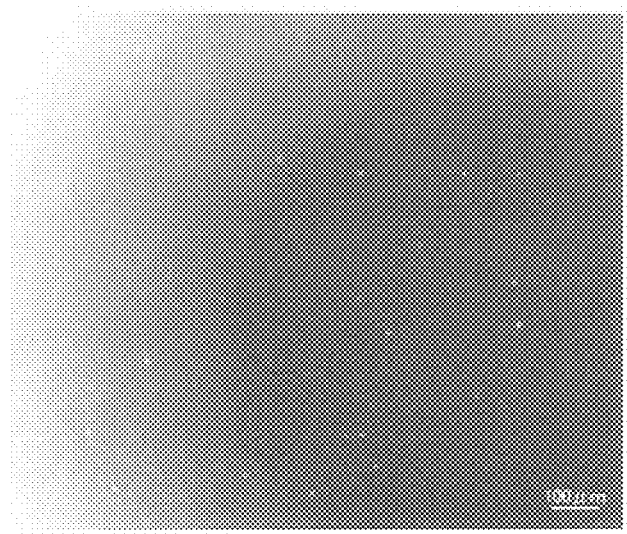
FIG. 13 is a Figure showing a film, which is one embodiment of the structure of the present invention, wherein the concentration of the deacylated gellan gum in the medium composition was 0.02% (weight/volume).

One embodiment of the assembly of polymer compounds via an ion is a film structure. Such film is shown in FIG. 13 as an example.

The size of the structure in the present invention is preferably a size that passes a filter having a pore size of 0.2 μm to 200 μm when it is passed through a filter. The lower limit of the pore size is more preferably more than 1 μm and, in consideration of stable suspension of cells or tissues, it more preferably exceeds 5 μm. The upper limit of the pore size is more preferably less than 100 μm and, in consideration of the size of the cells or tissues, it is more preferably less than 70 μm.

The particular compound in the present invention refers to a compound that forms, upon mixing with a liquid medium, an indeterminate structure which is uniformly dispersed in the liquid, substantially retains the cells and/or tissues without substantially increasing the viscosity of the liquid, and shows an effect of preventing sediment thereof. The "without substantially increasing the viscosity of the liquid" means that the viscosity of the liquid does not exceed 8 mPa·s. In this case, the viscosity of the liquid (that is, the viscosity of the medium composition of the present invention) is not more than 8 mPa·s, preferably not more than 4 mPa·s, more preferably not more than 2 mPa·s. Furthermore, the chemical structure, molecular weight, property etc. of the particular compound are not limited as long as it forms the structure in a liquid medium, and shows an effect of uniformly suspending (preferably suspension standing) the cells and/or tissues without substantially increasing the viscosity of the liquid.

The viscosity of the liquid containing the structure can be measured, for example, by the method described in the below-mentioned Examples. Specifically, it can be measured under 37° C. conditions and using an E-type viscosity meter (manufactured by Toki Sangyo Co., Ltd., TV-22 type viscosity meter, model: TVE-22L, corn roter: standard roter 1°34'×R24, rotation number 100 rpm).

Examples of the particular compound to be used in the present invention include, but are not limited to, polymer compounds, preferably a polymer compound having an anionic functional group.

As the anionic functional group, carboxy group, sulfo group, phosphate group and a salt thereof can be mentioned, with preference given to carboxy group or a salt thereof.

As a polymer compound to be used in the present invention, one having one or more kinds selected from the aforementioned anionic functional groups can be used.

Preferable specific examples of the polymer compound to be used in the present invention include, but are not limited to, polysaccharides wherein not less than 10 single saccharides (e.g., triose, tetrose, pentose, hexsauce, heptose etc.) are polymerized, more preferably, acidic polysaccharides having an anionic functional group. The acidic polysaccharides here is not particularly limited as long as it has an anionic functional group in the structure thereof, and includes, for example, polysaccharides having a uronic acid (e.g., glucuronic acid, iduronic acid, galacturonic acid, mannuronic acid), polysaccharides having a sulfuric acid group or phosphate group in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include polymer compounds composed of one or more kinds selected from the group consisting of hyaluronic acid, gellan gum, deacylated gellan gum (hereinafter sometimes to be referred to as DAG), rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate and a salt thereof. Polysaccharides are preferably hyaluronic acid, DAG, diutan gum, xanthan gum, carageenan or a salt thereof, most preferably DAG since use thereof at a low concentration can suspend cells or tissues and in consideration of easy recovery of the cells or tissues.

The salt here includes, for example, alkali metal salts such as lithium, sodium, potassium, salts with alkaline earth metals such as calcium, barium, magnesium and salts with aluminum, zinc, copper, iron, ammonium, organic base and amino acid and the like salt.

The weight average molecular weight of these polymer compounds (polysaccharides etc.) is preferably 10,000 to 50,000,000, more preferably 100,000 to 20,000,000, still more preferably 1,000,000 to 10,000,000. For example, the molecular weight can be measured based on pullulan by gel penetration chromatography (GPC).

As described in the below-mentioned Examples, phosphorylated DAG can also be used. The phosphorylation can be performed by a known method.

In the present invention, plural kinds (preferably two kinds) of the above-mentioned polysaccharides can be used in combination. The kind of the combination of the polysaccharides is not particularly limited as long as the aforementioned structure is formed in a liquid medium, and the cells and/or tissues can be uniformly suspended (preferably suspension stood) without substantially increasing the viscosity of the liquid. Preferably, the combination includes at least DAG or a salt thereof. That is, a preferable combination of polysaccharides contains DAG or a salt thereof, and polysaccharides other than DAG and a salt thereof (e.g., xanthan gum, alginic acid, carageenan, diutan gum, methylcellulose, locust bean gum or a salt thereof). Examples of specific combination of polysaccharides include, but are not limited to, DAG and rhamsan gum, DAG and diutan gum, DAG and xanthan gum, DAG and carageenan, DAG and xanthan gum, DAG and locust bean gum, DAG and κ-carageenan, DAG and sodium alginate, DAG and methylcellulose and the like.

More preferable specific examples of the particular compound to be used in the present invention include hyaluronic acid, deacylated gellan gum, diutan gum, carageenan and xanthan gum and a salt thereof. Most preferable examples include deacylated gellan gum and a salt thereof, since the viscosity of the medium composition can be made low and the cells or tissues can be easily recovered.

The deacylated gellan gum in the present invention is a linear polymer polysaccharide containing 4 molecules of sugars of 1-3 bonded glucose, 1-4 bonded glucuronic acid, 1-4 bonded glucose and 1-4 bonded rhamnose as the constituent unit, which is a polysaccharide of the following formula (I) wherein R1, R2 are each a hydrogen atom, and n is an integer of two or more. R1 may contain a glyceryl group, R2 may contain an acetyl group, and the content of the acetyl group and glyceryl group is preferably not more than 10%, more preferably not more than 1%.

The structure in the present invention takes various forms depending on the particular compound. In the case of deacylated gellan gum, it uptakes a metal ion (e.g., calcium ion) in a liquid medium when mixed with the liquid medium, forms an indeterminate structure via the metal ion, and suspends the cells and/or tissues. The viscosity of the medium composition of the present invention prepared from deacylated gellan gum is not more than 8 mPa·s, preferably not more than 4 mPa·s, and more preferably not more than 2 mPa·s for easy recovery of the cells or tissues.

ture in a liquid medium, and can uniformly suspend (preferably suspension stand) the cells and/or tissues without substantially increasing the viscosity of the liquid. It is generally 0.0005% to 1.0% (weight/volume), preferably 0.001% to 0.4% (weight/volume), more preferably 0.005% to 0.1% (weight/volume), still more preferably 0.005% to 0.05% (weight/volume). For example, in the case of deacylated gellan gum, it is added to a medium at 0.001% to 1.0% (weight/volume), preferably 0.003% to 0.5% (weight/volume), more preferably 0.005% to 0.1% (weight/volume), more preferably 0.01% to 0.05% (weight/volume), most

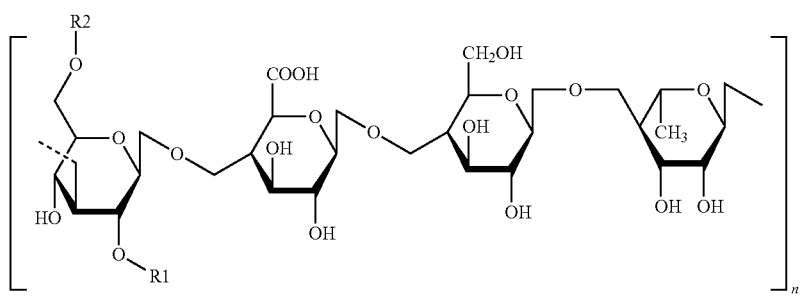

(I)

The particular compound in the present invention can be obtained by a chemical synthesis method. When the compound is a naturally-occurring substance, it is preferably obtained from various plants, various animals, various microorganisms containing the compound by extraction, separation and purification by conventional techniques. For extraction, the compound can be extracted efficiently by using water and supercritical gas. For example, as a production method of gellan gum, a producing microorganism is cultured in a fermentation medium, a mucosal substance produced outside fungus is recovered by a general purification method and, after the steps of drying, pulverizing and the like, powderized. When it is deacylated gellan gum, an alkali treatment is applied when a mucous substance is recovered, the glyceryl group and the acetyl group bonded to 1-3 bonded glucose residue are deacylated and recovered. Examples of the purification method include liquid-liquid extraction, fractional precipitation, crystallization, various kinds of ion exchange chromatography, gel filtration chromatography using Sephadex LH-20 and the like, adsorption chromatography using activated carbon, silica gel and the like, adsorption and desorption treatment of active substance by thin layer chromatography, high performance liquid chromatography using reversed-phase column and the like, and impurity can be removed and the compound can be purified by using them singly or in combination in any order, or repeatedly. Examples of the gellan gum-producing microorganism include, but are not limited to, *Sphingomonas elodea* and microorganism obtained by altering the gene of *Sphingomonas elodea*.

When it is deacylated gellan gum, commercially available products, for example, "KELCOGEL (registered trade mark of CP Kelco) CG-LA" manufactured by SANSHO Co., Ltd., "KELCOGEL (registered trade mark of CP Kelco)" manufactured by San-Ei Gen F.F.I., Inc. and the like can be used. As native-type gellan gum, "KELCOGEL (registered trade mark of CP Kelco) HT" manufactured by San-Ei Gen F.F.I., Inc. and the like can be used.

The concentration of the particular compound in a medium depends on the kind of the particular compound, and can be appropriately determined within the range where the particular compound can form the aforementioned strucpreferably, 0.01% to 0.03% (weight/volume). In the case of xanthan gum, it is added to a medium at 0.001% to 5.0% (weight/volume), preferably 0.01% to 1.0% (weight/volume), more preferably 0.05% to 0.5% (weight/volume), most preferably 0.1% to 0.2% (weight/volume). In the case of a κ-carageenan and locust bean gum mixture, it is added to a medium at 0.001% to 5.0% (weight/volume), preferably 0.005% to 1.0% (weight/volume), more preferably 0.01% to 0.1% (weight/volume), most preferably 0.03% to 0.05% (weight/volume). In the case of native-type gellan gum, it is added to a medium at 0.05% to 1.0% (weight/volume), preferably 0.05% to 0.1% (weight/volume).

When plural kinds (preferably two kinds) of the above-mentioned polysaccharides are used in combination, the concentration of the polysaccharides can form the aforementioned structure in a liquid medium, and can uniformly suspend (preferably suspension stand) the cells and/or tissues without substantially increasing the viscosity of the liquid. For example, when a combination of DAG or a salt thereof and polysaccharide other than DAG and a salt thereof is used, the concentration of DAG or a salt thereof is, for example, 0.005-0.02% (weight/volume), preferably 0.01-0.02% (weight/volume), and the concentration of polysaccharide other than DAG and a salt thereof is, for example, 0.005-0.4% (weight/volume), preferably 0.1-0.4% (weight/volume). Specific examples of the combination of the concentration range include the following. DAG or a salt thereof: 0.005-0.02% (preferably 0.01-0.02%) (weight/volume)

polysaccharide other than DAG xanthan gum: 0.1-0.4% (weight/volume)

sodium alginate: 0.1-0.4% (weight/volume)

locust bean gum: 0.1-0.4% (weight/volume)

methylcellulose: 0.1-0.4% (weight/volume) (preferably 0.2-0.4% (weight/volume))

carageenan: 0.05-0.1% (weight/volume)

diutan gum: 0.05-0.1% (weight/volume)

The concentration can be calculated by the following formula.

Concentration (%)=weight (g) of particular compound/volume (ml) of medium composition×100

The aforementioned compound can also be further converted to a different derivative by a chemical synthesis method, and the thus-obtained derivative can also be used effectively in the present invention. Specifically, in the case of deacylated gellan gum, a derivative of a compound represented by the formula (I) wherein a hydroxyl group for R1 and/or R2 is substituted by C1-3 alkoxy group, C1-3 alkylsulfonyl group, a monosaccharide residue such as glucose, fructose and the like, oligosaccharide residue such as sucrose, lactose and the like, or amino acid residue such as glycine, arginine and the like can also be used in the present invention. In addition, the compound can also be crosslinked using a crosslinking agent such as 1-ethyl-3-(3-di-methyl-aminopropyl)carbodiimide (EDC) and the like.

The particular compound or a salt thereof to be used in the present invention can be present in any crystal form depending on the production conditions, and can be present as any hydrate. Such crystal form, hydrate and mixtures thereof are also encompassed in the scope of the present invention. In addition, they may be present as a solvate containing an organic solvent such as acetone, ethanol, tetrahydrofuran and the like. Such forms are all encompassed in the scope of the present invention.

The particular compound to be used in the present invention may be present in the form of tautomer formed by isomerization in the ring or outside the ring, geometric isomer or tautomer, or a mixture of geometric isomers, or mixtures thereof. When the compound of the present invention has an asymmetric center, irrespective of whether the compound is formed by isomerization, it may be present in the form of a resolved optical isomer or a mixture containing same at any ratio.

The medium composition of the present invention may contain a metal ion, for example, a divalent metal ion (calcium ion, magnesium ion, zinc ion, ferrous ion, copper ion etc.), and preferably contains calcium ion. Two or more kinds of metal ions can be used in combination, for example, calcium ion and magnesium ion, calcium ion and zinc ion, calcium ion and ferrous ion, and calcium ion and copper ion. Those of ordinary skill in the art can appropriately determine the combination. In one embodiment, since the medium composition contains a metal ion, polymer compounds gather via a metal ion and form a three-dimensional network (e.g., polysaccharides form a microgel via a metal ion), whereby the structure of the present invention can be formed. The concentration of the metal ion can be appropriately determined within the range where the particular compound can form the aforementioned structure in a liquid medium, and can uniformly suspend (preferably suspension stand) the cells and/or tissues without substantially increasing the viscosity of the liquid medium. The salt concentration is, but is not limited to, 0.1 mM-300 mM, preferably 0.5 mM-100 mM. The metal ion may be mixed with a medium, or a salt solution is separately prepared and added to the medium. The medium composition of the present invention may contain the below-mentioned extracellular matrix, adhesion molecule and the like.

The present invention also includes a culture method for proliferating cells or tissues by using the medium composition, a method of recovering the obtained cells or tissues by, for example, filtration, centrifugation or magnetic separation, and a production method of a sphere by using the medium composition.

When cells and/or tissues are cultured in vitro, a structure composed of the particular compound to be used in the present invention shows an effect of suspending (preferably effect of suspension standing) the cells and/or tissues in a liquid containing the structure of the particular compound. By the suspending effect, a more increased amount of the cells and/or tissues per a given volume can be cultivated as compared to a single layer culture. When a conventional floating culture method accompanies rotation or shaking operation, the proliferation rate and recovery rate of the cells and/or tissues may become low, or the function of the cell may be impaired since a shear force acts on the cells and/or tissues. Using the medium composition of the present invention, which contains a structure of the particular compound, can uniformly disperse the cells and/or tissues without an operation such as shaking and the like, and can obtain the object cells and/or tissues easily in a large amount without loss of the cell function. In addition, when cells and/or tissues are suspension cultured in a conventional medium containing a gel substrate, observation and recovery of the cells and/or tissues are sometimes difficult, and the function thereof is sometimes impaired during recovery. However, using the medium composition containing the structure of the particular compound of the present invention, the cells and/or tissues can be subjected to suspension culture, observed without impairment of the function thereof, and can be recovered. In addition, a conventional medium containing a gel substrate sometimes shows high viscosity that makes it difficult to exchange the medium. However, since the medium composition containing the structure of the particular compound of the present invention has low viscosity, it can be exchanged easily with a pipette, pump and the like.

The human-derived cells and/or tissues cultured by the method of the present invention can be transplanted for a treatment object to patients having a disease or disorder. In this case, treatment target disease, the kind of disorder, a pre-treatment method and a cell transplantation method are appropriately selected by those of ordinary skill in the art. The engraftment of the transplanted cells in the recipient, recovery from the disease or disorder, the presence or absence of side effects associated with transplantation, and treatment effect are appropriately examined and judged by general methods for transplantation therapy.

Moreover, since the cells and/or tissues are efficiently proliferated by the method of the present invention, a medium composition containing the particular compound and a structure thereof of the present invention can be used as a reagent for cell research. For example, when a factor controlling the differentiation and proliferation of cells and tissues is to be elucidated, cells and the object factor are cocultured, and the number and kind of the cell, and changes in the cell surface differentiation marker and expressed gene are analyzed. In this case, using the medium composition of the present invention, the number of the analysis target cells can be efficiently amplified, and efficiently recovered as well. When the object factor is elucidated, the culture conditions, culture apparatus, the kind of medium, the kind of the compound of the present invention, the content of the particular compound, the kind of the additive, the content of the additive, culture period, culture temperature and the like are appropriately selected by those of ordinary skill in the art from the range described in the present specification. The cell that was proliferated or emerged by culture can be observed using a standard microscope in the pertinent field. In this case, cultured cells may be stained with a specific antibody. The expressed gene that has changed due to the object factor can be found by extracting the DNA (deoxyribonucleic acid) or RNA (ribonucleic acid) from the cultured cells and detecting by Southern Blotting, Northern Blotting, RT-PCR and the like. In addition, a cell surface differentiation marker is detected by ELISA and flow cytometry using a specific antibody, and the effect of the object factor on the differentiation and proliferation can be observed.

When cells and/or tissues are cultivated by the culture method of the present invention, culture tools generally used for cell culture such as schale, flask, plastic bag, Teflon (registered trade mark) bag, dish, schale, dish for tissue culture, multidish, microplate, microwell plate, multiplate, multiwall plate, chamber slide, cell culture flask, spinner flask, tube, tray, culture bag, roller bottle and the like can be used for cultivation. While the materials of these culture tools are not particularly limited, for example, glass, plastics such as polyvinyl chloride, cellulosic polymers such as ethylcellulose, acetylcellulose and the like, polystyrene, polymethylmethacrylate, polycarbonate, polysulfone, polyurethane, polyester, polyamide, polystyrene, polypropylene, polyethylene, polybutadiene, poly(ethylene-vinylacetate) copolymer, poly(butadiene-styrene) copolymer, poly(butadiene-acrylonitrile) copolymer, poly(ethylene-ethylacrylate) copolymer, poly(ethylene-methacrylate) copolymer, polychloroprene, styrol resin, chlorosulfonated polyethylene, ethylenevinyl acetate, acrylic block copolymer, and the like can be mentioned. These plastics are not only superior in gas permeability with oxygen, carbon dioxide and the like, but also superior in industrial molding processability, can stand various sterilization treatments, and are preferably transparent materials permitting observation of the inside of culture tools. Here, the method for sterilization treatment is not particularly limited and, for example, radiation sterilization, ethylene oxide gas sterilization, autoclave sterilization and the like can be mentioned. Moreover, these plastics may be applied with various surface treatments (e.g., plasma treatment, corona treatment etc.). Furthermore, these culture tools may be coated in advance with an extracellular matrix, a cell adhesion molecule and the like. Examples of the coating material include collagen I to XIX, gelatin, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin, hyaluronic acid, superfamily, Matrigel, poly-D-lysine, poly-L-lysine, chitin, chitosan, sepharose, alginic acid gel, hydrogel, cleavage fragments thereof and the like. These coating materials having an amino acid sequence artificially altered by gene recombination techniques can also be used. A coating material for inhibiting adhesion of the cells and/or tissues to culture tools can also be used. Examples of the coating material include, but are not limited to, silicon, poly(2-hydroxymethylmethacrylate), poly(2-methoxymethylacrylate), poly(2-methacryloyloxyethylphosphoryl choline), poly-N-isopropylacrylamide, mebiol gel (registered trade mark) and the like.

The cells and/or tissues can also be cultured by automatically conducting cell seeding, medium exchange, cell image obtainment, and recovery of cultured cells, under a mechanical control and under a closed environment while controlling pH, temperature, oxygen concentration and the like and using a bioreactor and an automatic incubator capable of high density culture. As a method for supplying a new medium and feeding the required substances to the cells and/or tissues during the culture using such apparatuses, fed-batch culture, continuous culture and perfusion culture are available, and all these methods can be used for the culture method of the present invention. Culture containers used for bioreactors and automatic incubators include open culture containers with easy opening-closing and a large contact area with the outside world (for example, culture containers having a lid), and closed culture containers with difficult ending-closing and a small contact area with the outside world (for example, cartridge type culture containers). Both culture containers can be used for the culture method of the present invention.

When cells and/or tissues are cultivated using the particular compound in the present invention, a medium composition can be prepared by mixing a medium used for cultivating the cells and/or tissues and the particular compound.

According to the classification by such composition of the medium, natural medium, semisynthetic medium and synthetic medium can be mentioned. According to the classification by the shape, semi-solid medium, liquid medium, powder medium (hereinafter sometimes to be referred to as powder medium) and the like can be mentioned. When the cells and/or tissues are derived from an animal, any medium used for culturing animal cells can be used. Examples of the medium include Dulbecco's Modified Eagle's Medium (DMEM), hamF12 medium (Ham's Nutrient Mixture F12), DMEM/F12 medium, McCoy's 5A medium, Eagle MEM medium (Eagle's Minimum Essential Medium; EMEM), αMEM medium (alpha Modified Eagle's Minimum Essential Medium; αMEM), MEM medium (Minimum Essential Medium), RPMI1640 medium, Iscove's Modified Dulbecco's Medium (IMDM), MCDB131 medium, William medium E, IPL41 medium, Fischer's medium, StemPro34 (manufactured by Invitrogen), X-VIVO 10 (manufactured by Cambrex Corporation), X-VIVO 15 (manufactured by Cambrex Corporation), HPGM (manufactured by Cambrex Corporation), StemSpan H3000 (manufactured by STEMCELL Technologies), StemSpanSFEM (manufactured by STEMCELL Technologies), StemlineII (manufactured by Sigma Aldrich), QBSF-60 (manufactured by Qualitybiological), StemPro hESC SFM (manufactured by Invitrogen), Essential8 (registered trade mark) medium (manufactured by Gibco), mTeSR1 or 2 medium (manufactured by STEMCELL Technologies), ReproFF or ReproFF2 (manufactured by ReproCELL), PSGro hESC/iPSC medium (manufactured by System Biosciences), NutriStem (registered trade mark) medium (manufactured by Biological Industries), CSTI-7 medium (manufactured by Cell Science & Technology Institute, Inc.), MesenPRO RS medium (manufactured by Gibco), MF-Medium (registered trade mark) mesenchymal stem cell proliferation medium (manufactured by TOYOBO CO., LTD.), Sf-900II (manufactured by Invitrogen), OptiPro (manufactured by Invitrogen), and the like.

The medium to be used for culture of cancer cells can be the above-mentioned medium added with a cell adhesion factor, and examples thereof include Matrigel, collagen gel, gelatin, poly-L-lysine, poly-D-lysine, laminin and fibronectin. It is possible to add two or more kinds of these cell adhesion factors in combination. Furthermore, a medium to be used for culture of cancer cell sphere can be further mixed with a thickener such as guargum, tamarind gum, alginic acid propyleneglycol, locust bean gum, gum arabic, tara gum, tamarind gum, methylcellulose and the like.

Examples of the medium to be used for culture of hepatocytes include, in addition to the above-mentioned media, HepatoZYME-SFM (manufactured by Life Technologies), HCM (registered trade mark)-hepatocyte culture medium Bullet Kit (registered trade mark, manufactured by Lonza), HBM (registered trade mark)-hepatocyte basic medium (manufactured by Lonza), HMM (registered trade mark)-hepatocyte maintenance medium (manufactured by Lonza), modified Lanford's medium (manufactured by NISSUI PHARMACEUTICAL CO., LTD.), ISOM's medium, liver cell proliferation medium (manufactured by Takara Bio Inc.), hepatocyte maintenance medium (manufactured by Takara Bio Inc.), hepatocyte basic medium (manufactured by Takara Bio Inc.), activity maintenance super medium (manufactured by In Vitro ADMET Laboratories) and the like. These media can contain a cell adhesion factor, and examples thereof include Matrigel, collagen gel, gelatin, poly-L-lysine, poly-D-lysine, laminin and fibronectin. It is also possible to add two or more kinds of these cell adhesion factors in combination. Furthermore, a medium to be used for culture of cancer cell sphere or hepatocyte sphere can be further mixed with a thickener such as guargum, tamarind gum, alginic acid propyleneglycol, locust bean gum, gum arabic, tara gum, tamarind gum, methylcellulose and the like.

When the cells and/or tissues are derived from a plant, a medium obtained by adding auxins and, where necessary, a plant growth control substance (plant hormone) such as cytokines and the like at a suitable concentration to a basic medium such as Murashige Skoog (MS) medium, Linsmaier Skoog (LS) medium, White medium, Gamborg's B5 medium, niche medium, hela medium, Morel medium and the like generally used for culture of plant tissues, or a modified medium wherein these medium components are modified to an optimal concentration (e.g., ammonia nitrogen at a half concentration etc.) can be mentioned as the medium. These media can be further supplemented, where necessary, with casein degrading enzyme, corn steep liquor, vitamins and the like. Examples of the auxins include, but are not limited to, 3-indoleacetic acid (IAA), 3-indolebutyric acid (IBA), 1-naphthaleneacetic acid (NAA), 2,4-dichlorophenoxyacetic acid (2,4-D) and the like. For example, auxins can be added to a medium at a concentration of about 0.1-about 10 ppm. Examples of the cytokines include, but are not limited to, kinetin, benzyladenine (BA), zeatin and the like. For example, cytokines can be added to a medium at a concentration of about 0.1-about 10 ppm.

Those of ordinary skill in the art can freely add, according to the object, sodium, potassium, calcium, magnesium, phosphorus, chlorine, various amino acids, various vitamins, antibiotic, serum, fatty acid, sugar and the like to the above-mentioned medium. For culture of animal-derived cells and/or tissues, those of ordinary skill in the art can also add, according to the object, one or more kinds of other chemical components and biogenic substances in combination.

Examples of the components to be added to a medium for animal-derived cells and/or tissues include fetal bovine serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various hormones, various proliferation factors, various extracellular matrices, various cell adhesion molecules and the like. Examples of the cytokine to be added to a medium include, but are not limited to, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating agent (M-CSF), granulocyte-macrophage colony stimulating agent (GM-CSF), stem cell factor (SCF), flk2/flt3 ligand (FL), leukemia cell inhibitory factor (LIF), oncostatin M (OM), erythropoietin (EPO), thrombopoietin (TPO) and the like.

Examples of the hormone to be added to a medium include, but are not limited to, melatonin, serotonin, thyroxine, triiodothyronine, epinephrine, norepinephrine, dopamine, anti-Mullerian hormone, adiponectin, adrenocorticotropic hormone, angiotensinogen and angiotensin, antidiuretic hormone, atrial natriuretic peptide, calcitonin, cholecystokinin, corticotropin release hormone, erythropoietin, follicle stimulating hormone, gastrin, ghrelin, glucagon, gonadotropin release hormone, growth hormone release hormone, human chorionic gonadotropin, human placental lactogen, growth hormone, inhibin, insulin, insulin-like growth factor, leptin, luteinizing hormone, melanocyte stimulating hormone, oxytocin, parathyroid hormone, prolactin, gastrin-releasing peptide, somatostatin, thrombopoietin, thyroid gland stimulation hormone, thyrotropin releasing hormone, cortisol, androstenedione, testosterone, dehydroepiandrosterone, androstenedione, dihydrotestosterone, estradiol, estrone, estriol, progesterone, calcitriol, calcidiol, prostaglandin, leukotriene, prostacyclin, thromboxane, prolactin releasing hormone, lipotropin, brain natriuretic peptide, neuropeptide Y, histamine, endothelin, pancreas polypeptide, rennin and enkephalin.

Examples of the growth factor to be added to a medium include, but are not limited to, transforming growth factor-α (TGF-α), transforming growth factor-β (TGF-β), macrophage inflammatory protein-1α (MIP-1a), epithelial cell growth factor (EGF), fibroblast growth factor-1, 2, 3, 4, 5, 6, 7, 8 or 9 (FGF-1, 2, 3, 4, 5, 6, 7, 8, 9), nerve cell growth factor (NGF) hepatocyte growth factor (HGF), leukemia inhibitory factor (LIF), protease nexin I, protease nexin II, platelet-derived growth factor (PDGF), choline vasoactive differentiation factor (CDF), chemokine, Notch ligand (Delta1 and the like), Wnt protein, angiopoietin-like protein 2, 3, 5 or 7 (Angpt2, 3, 5, 7), insulin like growth factor (IGF), insulin-like growth factor binding protein-1 (IGFBP), Pleiotrophin and the like.

In addition, these cytokines and growth factors having amino acid sequences artificially altered by gene recombinant techniques can also be added. Examples thereof include IL-6/soluble IL-6 receptor complex, Hyper IL-6 (fusion protein of IL-6 and soluble IL-6 receptor) and the like.

Examples of the various extracellular matrices and various cell adhesion molecules include collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunity globulin superfamily, Matrigel, poly-D-lysine, poly-L-lysine, chitin, chitosan, sepharose, hyaluronic acid, alginate gel, various hydrogels, cleavage fragments thereof and the like.

Examples of the antibiotic to be added to a medium include Sulfonamides and preparations, penicillin, phenethicillin, methicillin, oxacillin, cloxacillin, dicloxacillin, flucloxacillin, nafcillin, ampicillin, penicillin, amoxicillin, ciclacillin, carbenicillin, ticarcillin, piperacillin, azlocillin, mezlocillin, mecillinam, andinocillin, cephalosporin and a derivative thereof, oxolinic acid, amifloxacin, temafloxacin, nalidixic acid, Piromidic acid, ciprofloxacin, cinoxacin, norfloxacin, perfloxacin, Rosaxacin, ofloxacin, enoxacin, pipemidic acid, sulbactam, clavulanic acid, β-bromopenisillanic acid, β-chloropenisillanic acid, 6-acetylmethylene-penisillanic acid, cephoxazole, sultampicillin, adinoshirin and sulbactam formaldehyde hudrate ester, tazobactam, aztreonam, sulfazethin, isosulfazethin, norcardicin, m-carboxyphenyl, phenylacetamidophosphonic acid methyl, Chlortetracycline, oxytetracycline, tetracycline, demeclocycline, doxycycline, methacycline, and minocycline.

When the particular compound in the present invention is added to the above-mentioned medium, the particular compound is dissolved or dispersed in an appropriate solvent when in use (this is used as a medium additive). Thereafter, the medium additives can be added to a medium such that the concentration of the particular compound in the medium is, as detailedly described above, a concentration at which the cells and/or tissues can be uniformly suspended (preferably suspension stood) without substantially increasing the viscosity of the liquid medium, for example, 0.0005% to 1.0% (weight/volume), preferably 0.001% to 0.4% (weight/volume), more preferably 0.005% to 0.1% (weight/volume), further preferably 0.005% to 0.05% (weight/volume). For example, in the case of deacylated gellan gum, it is added to a medium at 0.001% to 1.0% (weight/volume), preferably 0.003% to 0.5% (weight/volume), more preferably 0.005% to 0.1% (weight/volume), most preferably 0.01% to 0.03% (weight/volume). In another aspect, in the case of deacylated gellan gum, it is added to a medium at 0.0005% to 1.0% (weight/volume), preferably 0.001% to 0.5% (weight/volume), more preferably 0.003% to 0.1% (weight/volume), most preferably 0.005% to 0.03% (weight/volume). In the case of xanthan gum, it is added to a medium at 0.001% to 5.0% (weight/volume), preferably 0.01% to 1.0% (weight/volume), more preferably 0.05% to 0.5% (weight/volume), most preferably 0.1% to 0.2% (weight/volume). In the case of a κ-carageenan and locust bean gum mixture, it is added to a medium at 0.001% to 5.0% (weight/volume), preferably 0.005% to 1.0% (weight/volume), more preferably 0.01% to 0.1%, most preferably 0.03% to 0.05% (weight/volume). In the case of a deacylated gellan gum and diutan gum mixture, it is added to a medium at 0.001% to 1.0% (weight/volume), most preferably 0.005% to 0.01% (weight/volume). In the case of a deacylated gellan gum and methylcellulose mixture, it is added to a medium at 0.001% to 1.0% (weight/volume), most preferably 0.005% to 0.2% (weight/volume). In the case of a deacylated gellan gum and locust bean gum mixture, it is added to a medium at 0.001% to 1.0% (weight/volume), most preferably 0.01% to 0.1% (weight/volume). In the case of a deacylated gellan gum and sodium alginate mixture, it is added to a medium at 0.001% to 1.0% (weight/volume), most preferably 0.01% to 0.1% (weight/volume). In the case of a deacylated gellan gum and xanthan gum mixture, it is added to a medium at 0.001% to 1.0% (weight/volume), most preferably 0.01% to 0.1% (weight/volume). deacylated gellan gum and κ-carageenan mixture, it is added to a medium at 0.001% to 1.0% (weight/volume), most preferably 0.01% to 0.1% (weight/volume). The concentration can be calculated by the following formula.

$$\text{Concentration (\%)} = \text{weight (g) of particular compound/volume (ml) of medium composition} \times 100$$

Here, examples of appropriate solvent used for the medium additive include, but are not limited to, aqueous solvents such as water, dimethyl sulfoxide (DMSO), various alcohols (e.g., methanol, ethanol, butanol, propanol, glycerol, propylene glycol, butyleneglycol and the like), and the like. In this case, the concentration of the particular compound is 0.001% to 5.0% (weight/volume), preferably 0.01% to 1.0% (weight/volume), more preferably 0.1% to 0.6% (weight/volume). It is also possible to further add an additive to enhance the effect of the particular compound, or lower the concentration when in use. As an example of such additive, one or more kinds of guargum, tamarind gum, alginic acid propyleneglycol ester, locust bean gum, gum arabic, tara gum, tamarind gum, methylcellulose, carboxymethylcellulose, agarose, tamarind seed gum, polysaccharides such as pullulan and the like can be mixed. It is also possible to immobilize the particular compound on the surface of a carrier or carry the particular compound inside a carrier during culture. The particular compound can have any shape during provision or preservation. The particular compound may be in the form of a formulated solid such as tablet, pill, capsule, granule, or a liquid such as a solution obtained by dissolving in an appropriate solvent using a solubilizer or a suspension, or may be bonded to a substrate or a single substance. Examples of the additive used for formulating include preservatives such as p-oxybenzoic acid esters and the like; excipients such as lactose, glucose, sucrose, mannit and the like; lubricants such as magnesium stearate, talc and the like; binders such as polyvinyl alcohol, hydroxypropylcellulose, gelatin and the like; surfactants such as fatty acid ester and the like; plasticizers such as glycerol and the like; and the like. These additives are not limited to those mentioned above, and can be selected freely as long as they are utilizable for those of ordinary skill in the art. The particular compound of the present invention may be sterilized as necessary. The sterilization method is not particularly limited, and, for example, radiation sterilization, ethylene oxide gas sterilization, autoclave sterilization, filter sterilization and the like can be mentioned. When filter sterilization (hereinafter sometimes to be referred to as filtration sterilization) is to be performed, the material of the filter part is not particularly limited and, for example, glass fiber, nylon, PES (polyethersulfone), hydrophilic PVDF (polyvinylidene fluoride), cellulose mixed ester, celluloseacetate, polytetrafluoroethylene and the like can be mentioned. While the size of the pore in the filter is not particularly limited, it is preferably 0.1 μm to 10 more preferably 0.1 μm to 1 μm, most preferably 0.1 μm to 0.5 μm. The sterilization treatment may be applied when the particular compound is in a solid state or a solution state.

The medium composition of the present invention can be obtained by forming the above-mentioned structure in a liquid medium by adding a solution or dispersion of the particular compound prepared above to the liquid medium. Since a medium generally contains a sufficient concentration of metal ions to assemble polymer compounds through ions or form a three-dimensional network of polymer compounds, the medium composition of the present invention can be obtained by simply adding a solution or dispersion of the particular compound of the present invention to a liquid medium. Alternatively, a medium may be added to a medium additive (a solution or dispersion of the particular compound). Furthermore, the medium composition of the present invention can also be prepared by mixing the particular compound and a medium component in an aqueous solvent (for example, water including ion exchange water, ultrapure water and the like). Examples of the embodiment of mixing include, but are not limited to, (1) mixing a liquid medium and a medium additive (solution), (2) mixing a liquid medium and the above-mentioned polymer compound (solid such as powder etc.), (3) mixing a medium additive (solution) and a powder medium, (4) mixing a powder medium and the above-mentioned polymer compound (solid such as powder etc.) with an aqueous solvent, and the like. To prevent the particular compound in the medium composition of the present invention from being non-uniformly distributed, the embodiment of (1) or (4), or (1) or (3) is preferable.

When the particular compound is dissolved in a solvent (e.g., aqueous solvent such as water, liquid medium) or the particular compound and a powder medium are dissolved in a solvent, the mixture is preferably heated to promote dissolution. The heating temperature is, for example, 80° C.-130° C., preferably 100° C.-125° C. (e.g., 121° C.) at which heating sterilization is performed.

After heating, the obtained solution of the particular compound is cooled to room temperature. The above-mentioned structure composed of the particular compound can be formed by adding the aforementioned metal ion to the solution (e.g., by adding the solution to a liquid medium). Alternatively, the above-mentioned structure composed of the particular compound can also be formed by heating (for example, 80° C.-130° C., preferably 100° C.-125° C. (e.g., 121° C.)) the particular compound when dissolved in a solvent (e.g., an aqueous solvent such as water and liquid medium) containing the aforementioned metal ion, and cooling the obtained solution to room temperature.

Examples of the preparation method of the medium composition of the present invention are shown below, which are not to be construed as limitative. The particular compound is added to ion exchange water or ultrapure water. Then, the mixture is stirred with heating at a temperature at which the particular compound can be dissolved (e.g., not less than 60° C., not less than 80° C., not less than 90° C.) to allow for dissolution to a transparent state.

After dissolving, the mixture is allowed to cool with stirring, and sterilized (e.g., autoclave sterilization at 121° C. for 20 min). After cooling to room temperature, the aforementioned sterilized aqueous solution is added with stirring (e.g., homomixer etc.) to a given medium to be used for static culture to uniformly mix the solution with the medium. The mixing method of the aqueous solution and the medium is not particularly limited, and may be manual mixing such as pipetting etc., or mixing with an instrument such as magnetic stirrer, mechanical stirrer, homomixer and homogenizer. Furthermore, the medium composition of the present invention can be filtrated through a filter after mixing. The size of the pore of the filter to be used for the filtration treatment is 5 μm to 100 μm, preferably 5 μm to 70 μm, more preferably 10 μm to 70 μm.

Alternatively, a powder medium and the above-mentioned polymer compound (solid such as powder etc.) is mixed with an aqueous solvent, and the mixture is heated at the above-mentioned temperature to prepare the medium composition of the present invention.

For example, when deacylated gellan gum is prepared, deacylated gellan gum is added to ion exchange water or ultrapure water to 0.1% to 1% (weight/volume), preferably 0.2% to 0.5% (weight/volume), more preferably 0.3% to 0.4% (weight/volume). Furthermore, in another aspect, when deacylated gellan gum is prepared, deacylated gellan gum is add to ion exchange water or ultrapure water to 0.1% to 1% (weight/volume), preferably 0.2% to 0.8% (weight/volume), more preferably 0.3% to 0.6% (weight/volume).

Then, the aforementioned deacylated gellan gum is dissolved to a transparent state by stirring with heating at any temperature as long as dissolution is possible, which may be not less than 60° C., preferably not less than 80° C., more preferably not less than 90° C. (e.g., 80-130° C.). After dissolution, the mixture is allowed to cool with stirring, and sterilized with autoclave at, for example, 121° C. for 20 min. After cooling to room temperature, the aqueous solution is added to, for example, DMEM/F-12 medium with stirring by a homomixer and the like to a desired final concentration (for example, when the final concentration is 0.015%, the ratio of 0.3% aqueous solution:medium is 1:19), and the mixture is uniformly mixed.

The mixing method of the aqueous solution and the medium is not particularly limited, and may be manual mixing such as pipetting etc., or mixing with an instrument such as magnetic stirrer, mechanical stirrer, homomixer and homogenizer.

Furthermore, the medium composition of the present invention can be filtrated through a filter after mixing. The size of the pore of the filter to be used for the filtration treatment is 5 μm to 100 μm, preferably 5 μm to 70 μm, more preferably 10 μm to 70 μm.

Furthermore, after preparation of the medium composition of the present invention, the structure can be sedimented by a centrifugation treatment.

Those of ordinary skill in the art can freely select the form and state of the cells and/or tissues to be cultured by the method of the present invention. Preferable specific examples thereof include, but are not particularly limited to, a state in which the cells and/or tissues are singly dispersed in the medium composition, a state in which the cells and/or tissues are attached to the surface of a carrier, a state in which the cells and/or tissues are embedded inside a carrier, a state in which plural cells assemble and form cell aggregations (spheres), or a state in which two or more kinds of cells assemble and form cell aggregations (spheres), and the like. More preferred are a state in which the cells and/or tissues are attached to the surface of a carrier, a state in which the cells and/or tissues are embedded inside a carrier, a state in which plural cells assemble and form cell aggregations (spheres), and a state in which two or more kinds of cells assemble and form cell aggregations (spheres). Further preferred are a state in which the cells and/or tissues are attached to the surface of a carrier, a state in which plural cells assemble and form cell aggregations (spheres), and a state in which two or more kinds of cells assemble and form cell aggregations (spheres). Among these states, the state with forming cell aggregations (spheres) can be mentioned as the most preferable state to be cultured by the culture method of the present invention, since cell-cell interactions and cell structures close to those in the in vivo environment are reconstructed, long-term culture can be performed while maintaining the cell function, and also cell recovery is relatively easy.

As a carrier to support the cells and/or tissues on the surface, microcarrier and glass bead composed of various polymers, ceramic bead, polystyrene bead, dextran bead and the like can be mentioned. As examples of the polymers, vinyl resin, urethane resin, epoxy resin, polystyrene, polymethylmethacrylate polyester, polyamide, polyimide, silicon resin, phenol resin, melamine resin, urea resin, aniline resin, ionomer resin, polycarbonate, collagen, dextran, gelatin, cellulose, alginates, mixtures thereof, and the like can be used. The carrier may be coated with a compound that enhances cell adhesion or release of substance from the cells. As examples of such coating materials, poly(monostearoylglycerides succinic acid), poly-D,L-lactid-co-glycolide, sodium hyaluronate, n-isopropylacrylamide, collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, sepharose, alginic acid gel, various hydrogels, further, cleavage fragments thereof, and the like can be mentioned. Here, two or more kinds of the coating materials may be combined. Furthermore, one or more kinds of polysaccharides such as guargum, tamarind gum, locust bean gum, gum arabic, tara gum, tamarind gum, methylcellulose, carboxymethylcellulose, agarose, tamarind seed gum, pullulan and the like can also be mixed with a medium to be used for culture of a carrier supporting the cells and/or tissues on the surface. The carrier may also contain a magnetic material, for example, ferrite. The diameter of the carrier is several tens of micrometers to several hundreds of micrometers, more preferably 100 μm to 200 μm, and its specific gravity is preferably close to 1, more preferably 0.9-1.2, particularly preferably about 1.0. Examples of the carrier include, but are not limited to, Cytodex 1 (registered trade mark), Cytodex 3 (registered trade mark), Cytoline 1 (registered trade mark), Cytoline 2 (registered trade mark), Cytopore 1 (registered trade mark), Cytopore 2 (registered trade mark), (above, GE Healthcare Life Sciences), Biosilon (registered trade mark) (NUNC), Cultispher-G (registered trade mark), Cultispher-S (registered trade mark) (above, Thermo SCIENTIFIC), HILLEXCT (registered trade mark), ProNectinF-COATED (registered trade mark), and HILLEXII (registered trade mark) (Solo Hill Engineering), GEM (registered trade mark) (Global Eukaryotic Microcarrier) and the like. The carrier may be sterilized as necessary. The sterilization method is not particularly limited and, for example, radiation sterilization, ethylene oxide gas sterilization, autoclave sterilization, dry heat sterilization, and the like can be mentioned. The method for culturing animal cells using the carrier is not particularly limited, and a culture method using a general flow layer-type culture vessel or filling layer-type culture vessel, and the like can be used. Here, a carrier supporting cells and/or tissues on the surface and using a medium composition comprising the structure of the particular compound of the present invention allows for uniform dispersion even without an operation of shaking and the like. As a result, the object cells and/or tissues can be cultured without losing cell function.

The cells and/or tissues cultured by this method can be collected by performing centrifugation and filtration treatment while the cells and/or tissues are supported by the carrier after the culture. In this case, centrifugation and filtration treatment may be performed after adding the liquid medium used. For example, unlimitatively, the gravitational acceleration (G) of centrifugation is 50G to 1000G, more preferably 100G to 500G, and the size of the pore of the filter used for the filtration treatment is 10 μm to 100 Furthermore, cultured carriers can be recovered with a magnetic force by encapsulating a material having magnetism, such as ferrite, in the carrier. The cells and/or tissues cultured by this method can be collected by releasing the carrier by using various chelating agents, a heat treatment, or an enzyme.

When cells and/or tissues are embedded inside a carrier, materials composed of various polymers can be selected as the carrier. As examples of such polymers, collagen, gelatin, alginates, chitosan, agarose, poly glycolic acid, polylactic acid, fibrin adhesive, polylactic acid-polyglycolic acid copolymer, proteoglycan, glycosaminoglycan, sponge such as polyurethane foam, DseA-3D (registered trade mark), poly N-substituted acrylamide derivative, poly N-substituted methacrylamide derivative, and copolymers thereof, polyvinyl methylether, polypropylene oxide, polyethylene oxide, temperature sensitive polymers such as partially acetified polyvinyl alcohol, polyacrylamide, polyvinyl alcohol, methylcellulose, nitrocellulose, cellulose butyrate, polyethylene oxide, and hydrogels such as poly(2-hydroxyethylmethacrylate)/polycaprolactone and the like can be mentioned. In addition, it is possible to prepare a carrier for embedding cells by using two or more kinds of these polymers. Furthermore, the carrier may have a physiologically active substance besides these polymers. As examples of the physiologically active substance, cell growth factors, differentiation inducing factors, cell adhesion factors, antibodies, enzymes, cytokines, hormones, lectins, extracellular matrices and the like can be mentioned, and a plurality of these can also be contained. Examples of the cell adhesion factor include poly(monostearoylglycerides succinic acid), poly-D,L-lactid-co-glycolide, sodium hyaluronate, n-isopropylacrylamide, collagen I to XIX, gelatin, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, sepharose, alginic acid gel, various hydrogels, further, cleavage fragments thereof, and the like. In this case, two or more kinds of cell adhesion factors may be combined. Furthermore, one or more kinds of thickeners such as guargum, tamarind gum, alginic acid propyleneglycol, locust bean gum, gum arabic, tara gum, tamarind gum, methylcellulose, carboxymethylcellulose, agarose, tamarind seed gum, pullulan, and the like can also be mixed with a medium used for culture of a carrier embedding cells and/or tissues.

The method for embedding the cells and/or tissues in these carriers is not particularly limited and, for example, a method including aspirating a mixture of the cells and the aforementioned polymers with a syringe and dropwise adding them to a medium from around 25G-19G injection needle, or dropwise adding to a medium using a micropipette, and the like can be used.

The size of the bead-like carrier formed here is determined by the shape of the tip of a tool used for the dropwise addition of a mixture of the cell and the aforementioned polymers, which is preferably several tens of micrometers to several thousands of micrometers, more preferably 100 μm to 2000 μm. The number of cells that can be cultured on a bead-like carrier is not particularly limited, and can be freely selected according to the bead size. For example, 5 million cells can be embedded in a bead-like carrier with a diameter of about 2000 μm. The cells may be singly dispersed within the carrier or plural cells may assemble to form a cell aggregate. Here, a carrier having the cells and/or tissues embedded therein and using a medium composition comprising the structure of the particular compound of the present invention allows for uniform dispersion even without an operation of stirring and the like. As a result, the object cells and/or tissues can be cultured without losing cell function. The cells and/or tissues cultured by this method can be collected by performing centrifugation and filtration treatment while the cells and/or tissues are embedded in the carrier after the culture. In this case, centrifugation and filtration treatment may be performed after adding the liquid medium used. For example, unlimitatively, the gravitational acceleration (G) of centrifugation is 50G to 1000G, more preferably 100G to 500G, and the size of the pore of the filter used for the filtration treatment is 10 μm to 100 μm. The cells and/or tissues cultured by this method can be collected by dispersing them by decomposing the carrier by a treatment using various chelating agents, heat, an enzyme and the like.

A method for forming a cell aggregate (sphere) is not particularly limited, and can be appropriately selected by those of ordinary skill in the art. Examples thereof include a method using a container having a cell non-adhesive surface, hanging drop method, gyratory culture method, three-dimensional scaffold method, centrifugation method, a method using coagulation by an electric field or magnetic field and the like. For example, using a method using a container having a cell non-adhesive surface, the object cells are cultured in a culture container such as schale and the like applied with a surface treatment to inhibit cell adhesion, whereby a sphere can be formed. Such cell non-adhesive culture container is used, the object cells are first collected, a cell suspension thereof is prepared and plated in the culture container to perform culture. When culture is continued for about 1 week, the cells spontaneously form a sphere. As a cell non-adhesive surface used here, a surface of a culture container generally used such as schale and the like, which is coated with a substance inhibiting cell adhesion and the like can be used. Examples of such substance include agarose, agar, copolymer of poly-HEMA(poly-(2-hydroxyl-ethylmethacrylate)2-methacryloyloxyethylphosphoryl choline and other monomer (for example, butylmethacrylate etc.), poly(2-methoxymethylacrylate), poly-N-isopropylacrylamide, mebiol gel (registered trade mark) and the like. When cytotoxicity is absent, the substance is not limited thereto.

As a method for forming a cell aggregate (sphere), the methods described in NATURE BIOTECHNOLOGY, VOL. 28, NO. 4, APRIL 2010, 361-366, NATURE PROTOCOLS, VOL. 6, NO. 5, 2011, 689-700, NATURE PROTOCOLS, VOL. 6, NO. 5, 2011, 572-579, Stem Cell Research, 7, 2011, 97-111, Stem Cell Rev and Rep, 6, 2010, 248-259 and the like can also be used.

In addition, a medium used for culture for forming a sphere can also contain a component that promotes formation of a sphere or promotes maintenance thereof. Examples of the component having such effect include dimethyl sulfoxide, superoxide dismutase, caeruloplasmin, catalase, peroxidase, L-ascorbic acid, L-ascorbic acid phosphate ester, tocopherol, flavonoid, uric acid, bilirubin, selenium-containing compound, transferrin, unsaturated fatty acid, albumin, theophylline, forskolin, glucagon, dibutyryl cAMP and the like. As the selenium-containing compound, ROCK inhibitors such as sodium selenite, sodium selenate, dimethyl selenide, hydrogen selenide, Selenomethionine, Se-Methylselenocysteine, Selenocystathionine, Selenohomocysteine, adenosine-5'-triphosphoric acid, Se-Adenosylselenomethionine, Y27632, Fasudil (HA1077), H-1152, Wf-536 and the like can be mentioned. To obtain the object cell aggregate having a uniform size, plural concaves having the same diameter as the object cell aggregate can also be introduced onto a cell non-adhesive culture container to be used. When these concaves are in contact with each other or within the range of the diameter of the object cell aggregate, and cells are plated, the plated cells do not form a cell aggregate between concaves but certainly form a cell aggregate with a size corresponding to the volume thereof in the concave, thus affording a cell aggregate population having a uniform size. As the shape of the concave in this case is preferably a hemisphere or cone.

Alternatively, a sphere can also be formed based on a support showing cell adhesiveness. Examples of such support include collagen, polyrotaxane, polylactic acid (PLA), polylactic acid glycolic acid (PLGA) copolymer, hydrogel and the like.

In addition, a sphere can also be formed by co-cultivating with a feeder cell. As a feeder cell to promote sphere formation, any adhesive cell can be used. Preferably, a feeder cell for each kind of cell is desirable. Although not limited, for example, when a sphere of cells derived from the liver or cartilage is formed, examples of the feeder cell include COS-1 cell and vascular endothelial cell as preferable cell types.

Furthermore, a sphere can also be formed using the culture composition containing the structure of the particular compound of the present invention. In this case, the particular compound can be added to a medium used for sphere formation, such that the concentration of the particular compound is, as detailedly described above, a concentration at which the cells and/or tissues can be uniformly suspended (preferably suspension stood) without substantially increasing the viscosity of the liquid medium, for example, 0.0005% to 1.0% (weight/volume), preferably 0.001% to 0.3% (weight/volume), more preferably 0.005% to 0.1% (weight/volume), further preferably 0.01% to 0.05% (weight/volume). In another aspect, the particular compound can be added to a medium used for sphere formation, such that the concentration of the particular compound is, as detailedly described above, a concentration at which the cells and/or tissues can be uniformly suspended (preferably suspension stood) without substantially increasing the viscosity of the liquid medium, for example, 0.0005% to 1.0% (weight/volume), preferably 0.001% to 0.3% (weight/volume), more preferably 0.003% to 0.1% (weight/volume), further preferably 0.005% to 0.05% (weight/volume).

The sphere is prepared by uniformly dispersing the object cells in a medium containing the structure of the particular compound, and allowing them to cultivate by standing still for 3 days to 10 days. The prepared sphere can be recovered by centrifugation and filtration treatment. For example, unlimitatively, the gravitational acceleration (G) of centrifugation is 50G to 1000G, more preferably 100G to 500G, and the size of the pore of the filter used for the filtration treatment is 10 μm to 100 μm. In addition, using magnetic fine particles coated, on the surface, with an antibody that specifically binds to the object cell, cultured sphere can be recovered by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like.

The size of the sphere varies depending on the cell type and culture period and is not particularly limited. When it has a spherical shape or ellipse spherical shape, the diameter thereof is 20 μm to 1000 μm, preferably 40 μm to 500 μm, more preferably 50 μm to 300 μm, most preferably 80 μm to 200 μm.

Such sphere can maintain proliferative capacity for not less than 10 days, preferably not less than 13 days, more preferably not less than 30 days, by continuing the standing culture. By regularly further performing, during the standing culture, mechanical division, or a single cell-forming treatment and coagulation, the proliferative capacity can be maintained substantially infinitely.

The culture container to be used for culturing sphere is not particularly limited as long as it generally permits animal cell culture. For example, flask, dish, schale, tissue culture dish, multidish, microplate, microwell plate, multiplate, multiwall plate, chamber slide, cell culture flask, spinner flask, schale, tube, tray, culture bag, roller bottle, EZ SPHERE (manufactured by ASAHI GLASS CO., LTD.), Sumilon cell tight plate (manufactured by SUMITOMO BAKELITE) and the like can be mentioned.

Of these culture containers, microplate, microwell plate, multiplate and multiwall plate are preferably used when evaluation of many anticancer drugs, pharmaceutical product candidate compounds or pharmaceutical products is performed. While the well bottom shape of these plates is not particularly limited, flat bottom, U-shaped bottom and V-shaped bottom can be used, and U-shaped bottom is preferably used. While the materials of these culture tools are not particularly limited, for example, glass, plastics such as polyvinyl chloride, cellulosic polymers, polystyrene, polymethylmethacrylate, polycarbonate, polysulfone, polyurethane, polyester, polyamide, polystyrene, polypropylene and the like, and the like can be mentioned.

The medium to be used for standing culture of sphere can contain a cell adhesion factor, examples thereof include Matrigel, collagen gel, gelatin, poly-L-lysine, poly-D-lysine, laminin and fibronectin. Two or more kinds of these cell adhesion factors can also be added in combination. Furthermore, the medium to be used for culturing sphere can be mixed with a thickener such as guargum, tamarind gum, alginic acid propyleneglycol, locust bean gum, gum arabic, tara gum, tamarind gum, methylcellulose, carboxymethylcellulose, agarose, tamarind seed gum, pullulan and the like.

Using a medium composition comprising the structure of the particular compound of the present invention, uniform dispersion in a medium can be afforded even without an operation of shaking and the like. As a result, the object cells and/or tissues can be cultured as a sphere without losing cell function.

The sphere standing cultured by this method can be collected by performing centrifugation and filtration treatment after the culture. In this case, centrifugation and filtration treatment may be performed after adding the liquid medium used. For example, unlimitatively, the gravitational acceleration (G) of centrifugation is 50G to 1000G, more preferably 100G to 500G, and the size of the pore of the filter used for the filtration treatment is 10 μm to 100 μm. In addition, using magnetic fine particles coated, on the surface, with an antibody that specifically binds to the object cell, cultured sphere can be recovered by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like. The recovered sphere can be dispersed as a single cell by further decomposing by a treatment with various chelating agents, heat, filter, enzyme and the like. Cell recovery and exchange of the medium composition can also be achieved by performing centrifugation, a filtration treatment or a recovery treatment by magnetism by using a bioreactor and an automatic incubator capable of conducting under a mechanical control and under a closed environment.

As a method for standing culture of plant-derived cells and/or tissues, callus, which is an undifferentiated plant cell aggregate, can be cultivated. Callus can be induced by a method known for each plant species to be used. For example, a surface of a part of a tissue of a differentiated plant body (e.g., root, stalk, leaf section, seed, growing point, embryo, pollen etc.) is sterilized, where necessary, with 70% alcohol, 1% sodium hypochlorite solution and the like, a tissue section with a suitable size (e.g., about 1-about 5 mm square root section) is cut out with a knife and the like as necessary, the tissue section is plated on a callus induction medium sterilized in advance by an aseptic operation using a clean bench and the like, and aseptically cultivated under suitable conditions. The callus induced here may be subjected to liquid culture for mass proliferation, or may also be maintained as a seed strain by passaging in a passage medium. The passage culture may be performed using any of liquid medium and solid medium.

The amount of the plant cell aggregate inoculated when starting the standing culture using the medium composition of the present invention varies depending on the proliferation rate of the object cell, culture manner (batch culture, fed-batch culture, continuous culture etc.), culture period and the like. For example, when a plant cell aggregate such as callus and the like is to be cultivated, it is inoculated to the medium composition of the present invention such that the wet weight of the cell aggregate relative to the medium composition of the present invention is 4-8 (weight/volume (w/v))%, preferably 5-7 (w/v) %. The particle size of the plant cell aggregate during culture is 1 mm to 40 mm, preferably 3 mm to 20 mm, more preferably 5 mm to 15 mm. As used herein, the "particle size" means a diameter when, for example, the plant cell aggregate has a spherical shape, a long diameter when it has an ellipse spherical shape, and the maximum length possible when it has other shape.

The temperature when cells and/or tissues are cultivated is generally 25 to 39° C., preferably 33 to 39° C., for animal cells. The $CO_2$ concentration is generally 4 to 10% by volume in the culture atmosphere, and 4 to 6% volume is preferable. The culture period is generally 3 to 35 days, which may be freely set according to the object of the culture. The culture temperature for plant cells is generally 20 to 30° C. and, when light is necessary, they can be cultured under illuminance conditions of illuminance 2000-8000 lux.

While the culture period is generally 3 to 70 days, which may be freely set according to the object of the culture.

When cells and/or tissues are cultivated by the method of the present invention, cells and/or tissues prepared separately are added to the culture composition of the present invention and mixed to give a uniform dispersion. In this case, the mixing method is not particularly limited and, for example, manual mixing using pipetting and the like, mixing using instrument such as stirrer, vortex mixer, microplate mixer, shaking machine and the like can be mentioned. After mixing, the culture medium may be stood still, or the culture medium may be rotated, shaken or stirred as necessary. The rotation number and frequency can be appropriately set according to the object of those of ordinary skill in the art. When the medium composition needs to be exchanged during the standing culture period, the cells and/or tissues and the medium composition are separated by centrifugation or filtration treatment, and a new medium composition can be added of the cells and/or tissues. Alternatively, the cells and/or tissues are appropriately concentrated by centrifugation or filtration treatment, and a new medium composition can be added to the concentrated liquid.

For example, unlimitatively, the gravitational acceleration (G) of centrifugation is 50G to 1000G, more preferably 100G to 500G, and the size of the pore of the filter used for the filtration treatment is 10 μm to 100 μm. In addition, using magnetic fine particles coated, on the surface, with an antibody that specifically binds to the object cell, the cultured cells and/or tissues can be separated by magnetic force. Examples of such magnetic fine particles include Dynabeads (manufactured by Veritas Ltd.), MACS microbead (manufactured by Miltenyi Biotec), BioMag (manufactured by Techno Chemicals Corporation), magnetic microsphere (manufactured by Polysciences Inc.) and the like. Exchange of the medium composition can also be performed by using a bioreactor and an automatic incubator capable of conducting under a mechanical control and under a closed environment.

Since cancer cell can be efficiently proliferated by the method of the present invention, a medium composition containing the particular compound of the present invention can be used for the evaluation of an anticancer drug for the cancer cell. For example, when an anticancer drug that inhibits proliferation of cancer cell is to be elucidated, cancer cell and an anticancer drug are cocultured, and the number and kind of the cell, and changes in the cell surface differentiation marker and expressed gene are analyzed. In this case, using the medium composition of the present invention, the number of the target cells to be analyzed can be efficiently amplified, and efficiently recovered as well. In the present invention, particularly, a medium additive for cancer cell that contains deacylated gellan gum or a salt thereof and a medium composition for cancer cell containing the additive can be used for the evaluation of cancer cell proliferation or anticancer activity and the like. In this case, the concentration of deacylated gellan gum or a salt thereof is as mentioned above.

While cancer cell is also proliferated even by using diutan gum, deacylated gellan gum is more preferable, since a proliferation effect on the cancer cell is particularly superior, and it can be used at a low concentration (the aforementioned preferable concentration), which in turn prevents easy development of bubbles in the culture medium and facilitates recovery of the cancer cells.

More specific screening method for an anticancer drug includes, for example, a method comprising (a) a step of cultivating cancer cell in the medium composition of the present invention in the presence of a test substance and in the absence thereof, and (b) a step of analyzing changes in cancer cell proliferation. The method can further comprise a step of selecting a substance that suppresses proliferation of cancer cell as compared to that in the absence of the test substance and/or a step of recovering the cancer cell. The changes mean an increase or decrease in the proliferation of cancer cell. For the analysis, the above-mentioned method can be performed, but the method is not limited thereto.

When the activity of an anticancer drug is evaluated, the culture conditions, culture tools, culture apparatus, the kind of medium, the kind of the particular compound, the content of the particular compound, the kind of the additive, the content of the additive, culture period, culture temperature, the kind of the anticancer drug, the content of the anticancer drug and the like can be appropriately determined by those of ordinary skill in the art from the range described in the present specification. The cell that was proliferated or emerged by culture can be observed using a standard microscope in the pertinent field. When the cell number is measured, colony formation method, crystal violet method, thymidine uptake method, Trypan Blue staining method, ATP (adenosine 3 phosphoric acid) measurement method, 3-(4,5-dimethylthial-2-yl)-2,5-diphenyltetrazalium bromide (MTT) staining method, WST-1 (registered trade mark) staining method, WST-8 (registered trade mark) staining method, flow cytometry, a method using a cell number automatic measuring apparatus and the like can be used. Among these, WST-8 (registered trade mark) staining method can be most preferably utilized. When the cytotoxicity is evaluated, lactic acid dehydrogenase (LDH) activity measurement method, CytoTox-ONE (registered trade mark) method and the like can be used. Alternatively, cultured cell is stained with a specific antibody, cell surface differentiation marker is detected by ELISA or flow cytometry, and the effect of the anticancer drug on the proliferation and apoptosis can be observed. Furthermore, the gene that showed different expression due to the cancer fighting can be found by extracting the DNA (deoxyribonucleic acid) or RNA (ribonucleic acid) from the cultured cells and detecting by Southern Blotting, Northern Blotting, RT-PCR and the like.

Since the method of the present invention maintains survival and function of hepatocytes, a medium composition containing the particular compound of the present invention can be used for the evaluation of various effects of a pharmaceutical product or a medicament candidate substance on the hepatocytes. For example, when the toxicity effect of a medicament candidate substance is to be elucidated, hepatocytes and an evaluation target test substance are cocultured, and the number and kind of the cell, and changes in the cell surface differentiation marker and expressed gene are analyzed. In this case, using the medium composition of the present invention, the survival and function of the analysis target hepatocytes can be maintained, and the hepatocytes can be efficiently recovered as well.

As a method of screening for a pharmaceutical product candidate substance that acts on hepatocytes, a method comprising (a) a step of cultivating hepatocytes in the presence of a test substance and in the absence thereof in the medium composition of the present invention, and (b) a step of analyzing changes in the physiological function of the hepatocytes can be mentioned.

As a method of evaluating the efficacy or toxicity of a pharmaceutical product candidate substance that acts on hepatocytes, a method comprising (a) a step of cultivating hepatocytes in the presence of a test substance and in the absence thereof in the medium composition of the present invention, and (b) a step of analyzing changes in the physiological function of the hepatocytes can be mentioned. These methods can further comprise a step of selecting a substance that suppresses or increases the physiological function of the hepatocytes than in the absence of the test substance, and/or a step of recovering the hepatocytes. The changes refer to an increase or decrease in the physiological function of the hepatocytes (e.g., liver cell proliferation, enzyme activity of cytochrome P450 and the like). An increase in the physiological function of the hepatocytes can be evaluated to show low efficacy or toxicity, and a decrease in the physiological function of the hepatocytes can be evaluated to show high efficacy or toxicity, and the like.

When the activity of a medicament candidate substance is evaluated, the culture conditions, culture tools, culture apparatus, the kind of medium, the kind of the particular compound, the content of the particular compound, the kind of the additive, the content of the additive, culture period, culture temperature, the kind and the content of the pharmaceutical product or medicament candidate substance and the like can be appropriately selected by those of ordinary skill in the art from the range described in the present specification. The cell that was maintained or emerged by culture can be observed using a standard microscope in the pertinent field. When the cell number is measured, colony formation method, crystal violet method, thymidine uptake method, Trypan Blue staining method, ATP (adenosine 3 phosphoric acid) measurement method, 3-(4,5-dimethylthial-2-yl)-2,5-diphenyltetrazalium bromide (MTT) staining method, WST-1 (registered trade mark) staining method, WST-8 (registered trade mark) staining method, flow cytometry, a method using a cell number automatic measuring apparatus and the like can be used. Among these, WST-8 (registered trade mark) staining method can be most preferably utilized. When the cytotoxicity is evaluated, lactic acid dehydrogenase (LDH) activity measurement method, CytoTox-ONE (registered trade mark) method and the like can be used. Alternatively, cultured cell is stained with a specific antibody, cell surface differentiation marker is detected by ELISA (Enzyme-linked immunosorbent assay) or flow cytometry, and the effect of the pharmaceutical product or medicament candidate substance on the proliferation and apoptosis can be observed. Furthermore, the gene that showed different expression due to the pharmaceutical product or medicament candidate substance can be found by extracting the DNA (deoxyribonucleic acid) or RNA (ribonucleic acid) from the cultured cells and detecting by Southern Blotting, Northern Blotting, RT-PCR and the like. Moreover, the protein that showed different expression due to the pharmaceutical product or medicament candidate substance can be detected by ELISA, Western Blotting, flow cytometry and the like. Furthermore, the enzyme activity of cytochrome P450 can be detected by measuring the activity of the enzyme to convert the substrate structure by radioactive isotope method, high performance liquid chromatography method, luminescence method, color development method and the like.

EXAMPLES

The present invention is explained in more detail in the following by concretely describing the Analysis Examples and Experimental Examples of the medium composition of the present invention as Examples; however, the present invention is not limited thereto.

Analysis Example 1: Viscosity Measurement and Cell Suspension Test of Medium Containing Deacylated Gellan Gum Preparation and Viscosity Measurement of Deacylated Gellan Gum-Containing Medium Deacylated gellan gum (KELCOGEL CG-LA, manufactured by SANSHO Co., Ltd.) was suspended in pure water to 0.4% (w/v), and dissolved by stirring with heating at 90° C. This aqueous solution was allowed to cool to room temperature with stirring, and sterilized at 121° C. for 20 min in an autoclave. A 2-fold concentration of DMEM/F-12 medium (manufactured by Aldrich, 50 mL) and sterilization water (47.5 mL) were placed in a 300 mL tall beaker with stirring by a homomixer (3000 rpm) at room temperature, aqueous deacylated gellan gum solution (2.5 mL) was added, and the mixture was continuously stirred for 1 min to prepare a deacylated gellan gum medium composition with a final concentration of 0.01%. Medium compositions added with aqueous deacylated gellan gum solution with final concentrations of 0.02, 0.03 and 0.05% (w/v) were similarly prepared. The viscosity of the medium compositions was measured using an E type viscometer (manufactured by Toki Sangyo Co., Ltd., Viscometer TVE-22L, standard roter 1°34'×R24) under 37° C. condition at 100 rpm for 5 min.

Cell Suspension Test of Deacylated Gellan Gum-Containing Medium

Human cervical cancer cell line HeLa (manufactured by DS PHARMA BIOMEDICAL CO., LTD.) was suspended in EMEM medium containing 10% (v/v) fetal bovine serum (manufactured by WAKO) at 250000 cells/mL, the suspension (10 mL) was plated on EZ SPHERE (manufactured by ASAHI GLASS CO., LTD.), and cultured in a $CO_2$ incubator (5% $CO_2$) for 3 days. The obtained suspension (10 mL) of spheres (diameter 100-200 μm) was centrifuged (200G, 5 min) to allow for sphere sedimentation, and the supernatant was removed to give a sphere suspension (1.0 mL). Successively, the deacylated gellan gum-containing medium prepared above was placed in a 1.5 mL Eppendorf tube by 1.0 mL, and a HeLa cell sphere suspension (10 μL) was further added. The cell aggregate was dispersed by tapping, incubated at 37° C., and the dispersion state of the cells 1 hr later was visually observed.

(Comparative Example) Preparation of Methylcellulose and Collagen-Containing Medium Preparation of Methylcellulose-Containing Medium DMEM/F-12 medium (manufactured by Aldrich, 100 mL) was placed in a 200 mL pear-shaped flask, and methylcellulose (M0387, manufactured by Aldrich, 0.1 g) was added. The mixture was stirred while cooling in an ice bath to dissolve methylcellulose. Using this solution, medium compositions added with the aqueous methylcellulose solution at a final concentration of 0.1, 0.3, 0.6 or 1.0% (w/v) were prepared.

Preparation of Collagen-Containing Medium

A 10-fold concentration of DMEM/F-12 medium (manufactured by Aldrich, 1 mL), a buffer for reconstitution (manufactured by Nitta Gelatin Inc., 1 mL) and pure water (1.5 mL) were added to 0.3% cell matrix type I-A (manufactured by Nitta Gelatin Inc., 6.5 mL), and the mixture was stirred in an ice to give a 0.2% collagen-containing medium. Similarly, medium compositions added with collagen at a final concentration of 0.01, 0.05, 0.1 or 0.2% (w/v) were prepared.

The medium compositions prepared above were subjected to a suspension test of HeLa cell spheres and a viscosity measurement, in the same manner as with the deacylated gellan gum-containing medium. The viscosity of 1.0% (w/v) methylcellulose was measured at 50 rpm due to the measurement range of the apparatus.

TABLE 1

| deacylated gellan gum concentration % (w/v) | state | viscosity (mPa·s) | HeLa cell suspension/ sedimentation |
|---|---|---|---|
| 0.01 | liquid | 1.31 | suspension |
| 0.02 | liquid | 1.92 | suspension |
| 0.03 | liquid | 2.38 | suspension |
| 0.05 | liquid | 3.34 | suspension |

TABLE 2

| methylcellulose concentration % (w/v) | state | viscosity (mPa·s) | HeLa cell suspension/ sedimentation |
|---|---|---|---|
| 0.1 | liquid | 2.31 | sedimentation |
| 0.3 | liquid | 8.15 | sedimentation |
| 0.6 | liquid | 13.0 | sedimentation |
| 1.0 | liquid | 48.2 | sedimentation |

TABLE 3

| collagen concentration % (w/v) | state | viscosity (mPa · s) | HeLa cell suspension/ sedimentation |
|---|---|---|---|
| 0.01 | liquid | 1.18 | sedimentation |
| 0.05 | liquid/solid (gel) | unmeasurable | suspension |
| 0.1 | solid (gel) | unmeasurable | suspension |
| 0.2 | solid (gel) | unmeasurable | suspension |

EXPERIMENTAL EXAMPLES

While the usefulness of the medium composition of the present invention in cell culture is concretely explained in the following Experimental Examples, the present invention is not limited thereto alone. The $CO_2$ concentration (%) in a $CO_2$ incubator was shown by % volume of $CO_2$ in the atmosphere. PBS means phosphate buffered saline (manufactured by Sigma Aldrich Japan), and FBS means fetal bovine serum (manufactured by Biological Industries). In addition, (w/v) shows weight per volume.

Experimental Example 1: Cell Proliferation Test by Dispersing Single Cell

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to IMDM medium (manufactured by Gibco) containing 10% (v/v) fetal bovine serum and 10 ng/mL thrombopoietin (manufactured by WAKO). Successively, human leukemia cell line UT7/TPO was plated on a medium composition added with the above-mentioned deacylated gellan gum to 20000 cells/mL, and dispensed to a 6-well flat bottom microplate (manufactured by Corning Incorporated) at 5 mL/well. Similarly, human cervical cancer cell line HeLa (manufactured by DS PHARMA BIOMEDICAL CO., LTD.) was plated at 20000 cell/mL on a medium composition obtained by adding 0.015% (w/v) deacylated gellan gum (KELCOGEL CG-LA, manufactured by SANSHO Co., Ltd.) to EMEM medium containing 10% (v/v) fetal bovine serum (manufactured by WAKO), and the composition was dispensed to a 6-well flat bottom microplate (manufactured by Corning Incorporated) at 5 mL/well. The cell suspensions were cultured while being stood still in a $CO_2$ incubator (5% $CO_2$) for 3 days. Thereafter, a part of the culture medium was recovered, the same amount of Trypan Blue staining solution (manufactured by Invitrogen Corporation) was added, and the number of viable cells was measured by blood cell meter (manufactured by ERMA INC.)

As a result, it was confirmed that, using the medium composition of the present invention, UT7/TPO cells and HeLa cells can be uniformly cultivated in a suspended state, and efficiently proliferate in the medium composition. The cell numbers of UT7/TPO cells and HeLa cells after static suspension culture for 3 days are shown in Table 4.

TABLE 4

| | UT7/TPO cells | HeLa cells |
|---|---|---|
| cell number (×10000/mL) | 38 | 40 |

Experimental Example 2: Cell Proliferation Test by Culturing Cell Line-Derived Sphere Human liver cancer cell line HepG2 (manufactured by DS PHARMA BIOMEDICAL CO., LTD.) was suspended in DMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 7 days in a $CO_2$ incubator (5% $CO_2$). Similarly, human cervical cancer cell line HeLa (manufactured by DS PHARMA BIOMEDICAL CO., LTD.) was suspended in EMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 7 days in a $CO_2$ incubator (5% $CO_2$). The suspension (2.5 mL) of the sphere (diameter 100-200 μm) of each cell line obtained here was centrifuged (200G, 5 min) to allow for sphere sedimentation, and the supernatant was removed. Successively, the above-mentioned medium (10 mL) was added to the spheres (about 800 spheres) to suspend them and the suspension was transferred to a flat bottom tube (manufactured by BM Equipment Co., Ltd.). Similarly, using a medium composition obtained by adding 0.015% (w/v) deacylated gellan gum (KELCOGEL CG-LA, manufactured by SANSHO Co., Ltd.) to the above-mentioned medium, a sphere suspension was produced and transferred to a flat bottom tube (manufactured by BM Equipment Co., Ltd.). The medium composition added with 0.015% (w/v) deacylated gellan gum was prepared by first suspending deacylated gellan gum (KELCOGEL CG-LA, manufactured by SANSHO Co., Ltd.) in ultrapure water (Milli-Q water) to 0.3% (w/v), dissolving same by stirring with heating at 90° C., sterilizing this aqueous solution at 121° C. for 20 min in an autoclave, and adding the solution at 1/20 dilution to DMEM medium containing 10% (v/v) fetal bovine serum.

After static culture of the above-mentioned sphere suspension in a $CO_2$ incubator (5% $CO_2$) at 37° C. for 3 days, a two-fold volume of the medium was added. The mixture was centrifuged (200G, 5 min) to allow for sphere sedimentation, and the supernatant was removed. At this point, a part of the sphere was taken, and the shape thereof was observed with an optical microscope (manufactured by OLMPUS, CK30-F100). Successively, the recovered sphere was washed once with PBS (10 mL), 1 mL of trypsin-EDTA (ethylenediaminetetraacetic acid) solution (manufactured by WAKO) was added, and the mixture was incubated at 37° C. for 5 min. The above-mentioned medium (9 mL) was added, and the cells were collected by centrifugation (200G, 5 min). To a part of the obtained cell suspension (2 mL) was added the same amount of a Trypan Blue staining solution (manufactured by Invitrogen Corporation), and the numbers of the viable cells and dead cells were measured by a hemocytometer (manufactured by ERMA INC.).

As a result, it was confirmed that, using the medium composition of the present invention, the spheres of HepG2 cells and HeLa cells could be cultivated in a suspended state, and the cells efficiently proliferate in the medium composition. Furthermore, the medium composition of the present invention was confirmed to show a small rate of the dead cells as compared to the existing media when the cells were proliferated, and have a superior cell proliferation promoting effect. The sphere cultured in an existing medium sedimented on the bottom of the culture container. Furthermore, the shape of the cultured sphere was observed by an optical microscope. As a result, the medium composition of the present invention did not show association of the spheres, whereas association of the spheres was observed in the existing media.

Figure 2:
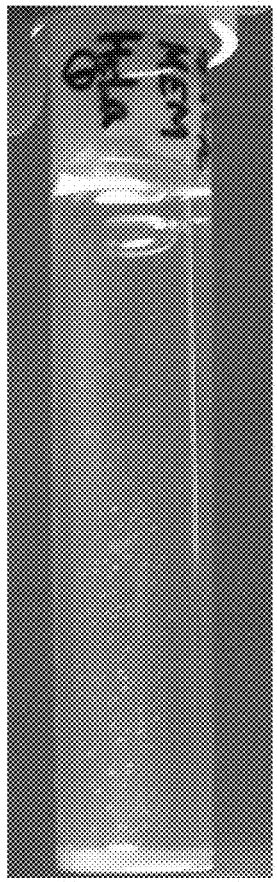
FIG. 2 is a Figure showing that, when spheres of HeLa cells were cultured in the medium composition of the present invention, the spheres were uniformly dispersed and could be cultured in a suspended state.
Figure 3:
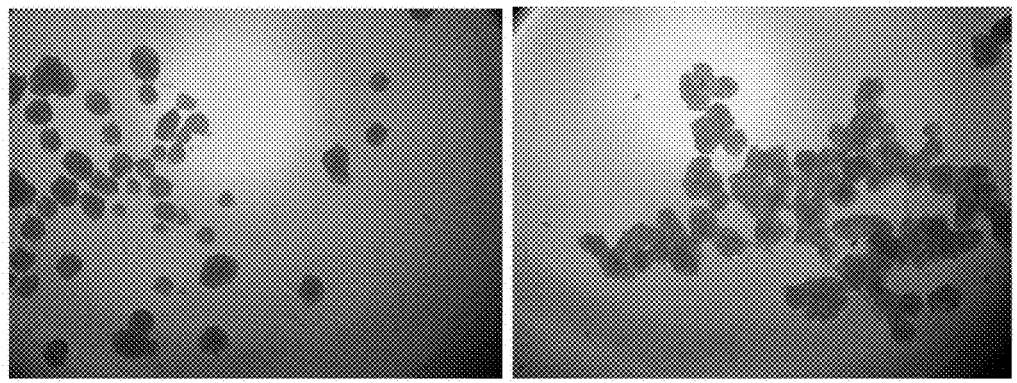
FIG. 3 is a Figure showing that, when spheres of HeLa cells were cultured in the medium composition of the present invention and observed with a microscope, association of the spheres could be suppressed compared to existing media.

The relative number of the HepG2 cells and HeLa cells is shown in Table 5, wherein the number of the cells cultured in a medium free of deacylated gellan gum is 1. In addition, the relative rate of the dead cells is shown in Table 6, wherein the rate of the dead cells cultured in a medium free of deacylated gellan gum (dead cell number/viable cell number) is 1. The suspended state of the spheres of HepG2 cells and HeLa cells cultured in the medium composition of the present invention is shown in FIG. 1 and FIG. 2, respectively. Furthermore, the shape of the sphere of the cultured HeLa cells is shown in FIG. 3.

TABLE 5

| deacylated gellan gum | | HepG2 cells | HeLa cells |
|---|---|---|---|
| absent | relative cell number | 1.0 | 1.0 |
| present | relative cell number | 1.7 | 1.5 |

TABLE 6

| deacylated gellan gum | | HepG2 cells | HeLa cells |
|---|---|---|---|
| absent | relative mortality rate | 1.0 | 1.0 |
| present | relative mortality rate | 0.5 | 0.5 |

Figure 4:
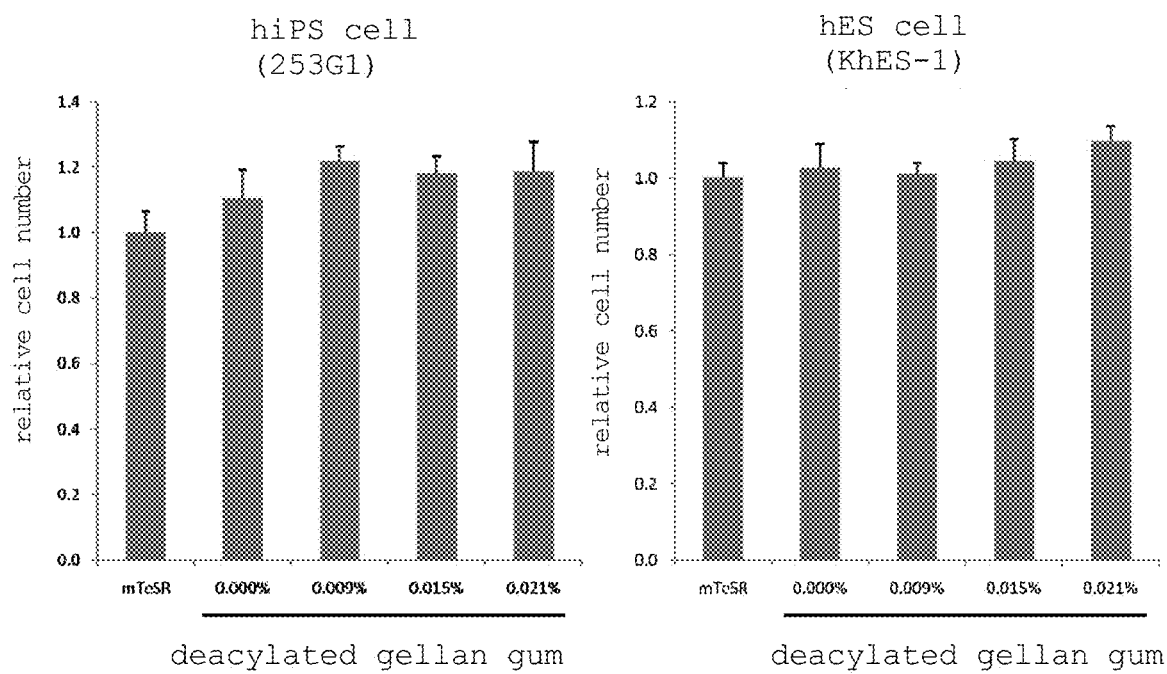
FIG. 4 is a Figure showing that, when pluripotent stem cells were cultured in the medium composition of the present invention, toxicity to the cells was not found.

Experimental Example 3: Cell Proliferation Test of Human Pluripotent Stem Cells in Adhesion Culture Human pluripotent stem cells (hPSCs) are generally proliferated and maintained on a feeder or a culture dish coated with Matrigel under flat plane culture conditions permitting adhesion. To evaluate toxicity of deacylated gellan gum to hPSCs, deacylated gellan gum was added at a concentration of 0.000% to 0.020% (w/v) to mTeSR medium (manufactured by STEM CELL Technologies) under flat plane culture conditions using Matrigel (manufactured by Becton, Dickinson and Company), and the influence on the proliferation of hPSCs was examined. In this case, Kyoto University 253G1 strain was cultured as human iPS cells and Kyoto University KhES-1 strain was cultured as human ES cell line. The medium composition added with the above-mentioned concentration of deacylated gellan gum was prepared by first suspending deacylated gellan gum (KELCOGEL CG-LA, manufactured by SANSHO Co., Ltd.) in ultrapure water (Milli-Q water) to 0.3% (w/v), dissolving same by stirring with heating at 90° C., sterilizing the aqueous solution at 121° C. for 20 min in an autoclave, and adding the solution to mTeSR medium at a given concentration. As a result, a cell number of the same level as that of general mTeSR media could be obtained for both human iPS cells and human ES cells by using a medium added with deacylated gellan gum, and toxicity by deacylated gellan gum was not found. The results are shown in FIG. 4. The cell number after culture as shown in FIG. 4 is a relative value of the cell number, which was obtained by plating hPSCs in Matrigel-coated culture dish and culturing the cells in mTeSR medium containing deacylated gellan gum for 5 days, to the cell number in mTeSR medium free of deacylated gellan gum as 1.

Figure 5:
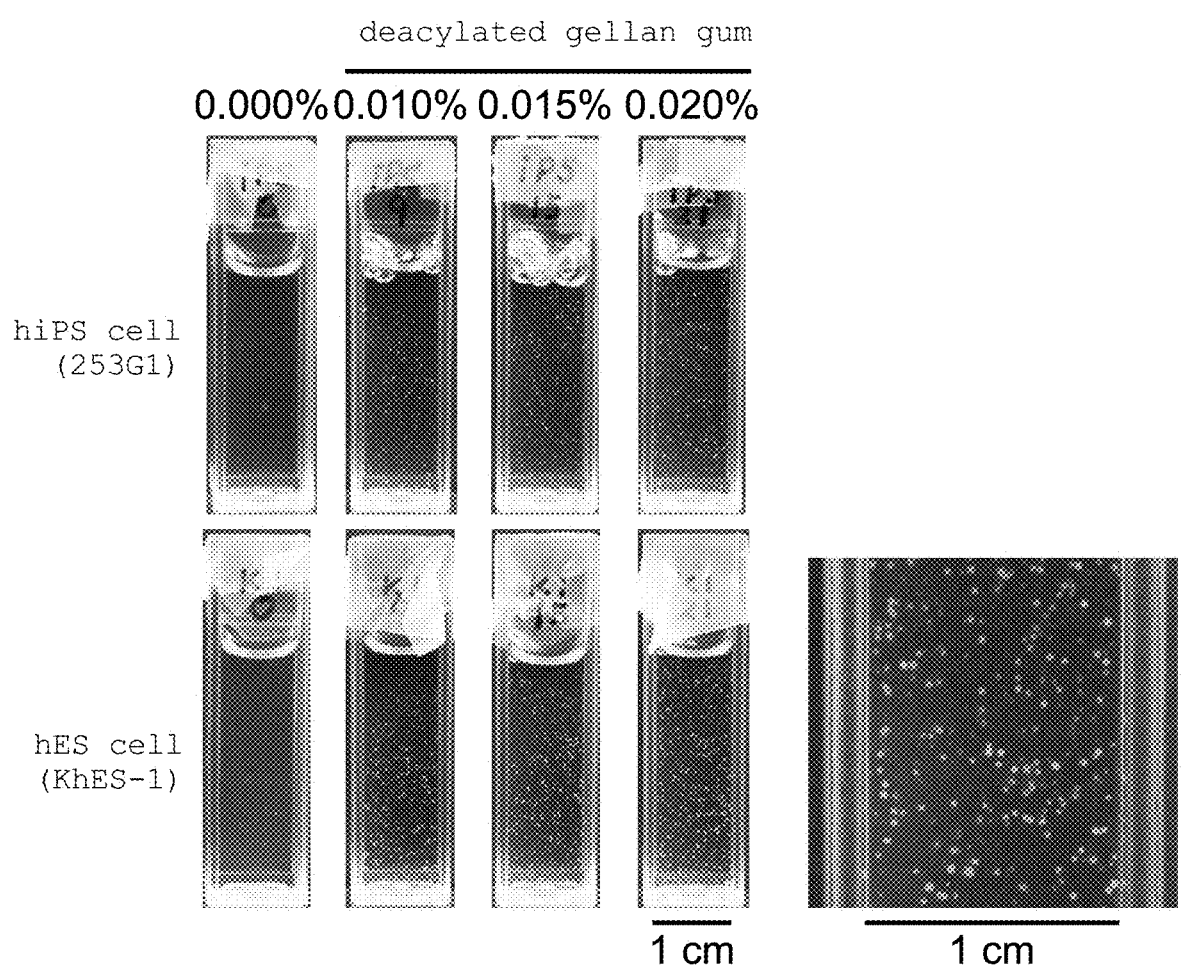
FIG. 5 is a Figure showing that, when spheres of pluripotent stem cells were cultured in the medium composition of the present invention, the spheres were uniformly dispersed and were in a suspended state.

Experimental Example 4: Sedimentation Suppression Test of Deacylated Gellan Gum in Culture of Human Pluripotent Stem Cell Sphere hPSCs form a sphere on a low adhesive culture dish such as a petri culture dish and the like. For example, the sphere can be formed by any of the methods described in NATURE BIOTECHNOLOGY, VOL. 28, NO. 4, APRIL 2010, 361-366, NATURE PROTOCOLS, VOL. 6, NO. 5, 2011, 689-700, NATURE PROTOCOLS, VOL. 6, NO. 5, 2011, 572-579, Stem Cell Research, 7, 2011, 97-111, Stem Cell Rev and Rep, 6, 2010, 248-259. hPSCs (Kyoto University 253G1 strain or Kyoto University KhES-1 strain) maintained on feeder cells (mouse fetus fibroblast) was recovered, the feeder cells were removed by natural sedimentation, and hPSCs were resuspended in mTeSR medium added with a Rho kinase inhibitor Y-27632 (10 μM). Successively, hPSCs colony having a given size was inoculated to a petri culture dish (manufactured by BD Falcon), and cultivated in a $CO_2$ incubator (5% $CO_2$) at 37° C. to form a sphere. The medium was exchanged with Y-27632-free mTeSR medium on day 1 and day 3 after passage, and the cells were passaged in Y-27632-containing mTeSR medium every 5 days. The thus-prepared hPSCs sphere (day 4 of culture) was suspended in a medium composition obtained by adding deacylated gellan gum to mTeSR medium (prepared in the same manner as in Experimental Example 3) to 0.000% to 0.020% (w/v), and transferred to a cuvette. The cuvette was left standing in a $CO_2$ incubator (5% $CO_2$) at 37° C. overnight, and the sphere sedimentation suppressive effect of deacylated gellan gum was examined. The results are shown in FIG. 5. As shown in FIG. 5, the spheres could be three-dimensionally maintained in a suspended state in the medium in all concentration ranges by the addition of deacylated gellan gum. On the other hand, it was found that, in the existing medium free of deacylated gellan gum, the spheres sedimented on the bottom surface of the culture container and could not be kept in a suspended state. In addition, the effects of deacylated gellan gum were common in the human iPS cells and human ES cells. The above results show that deacylated gellan gum can maintain the hPSCs spheres in a suspended state.

Figure 6:
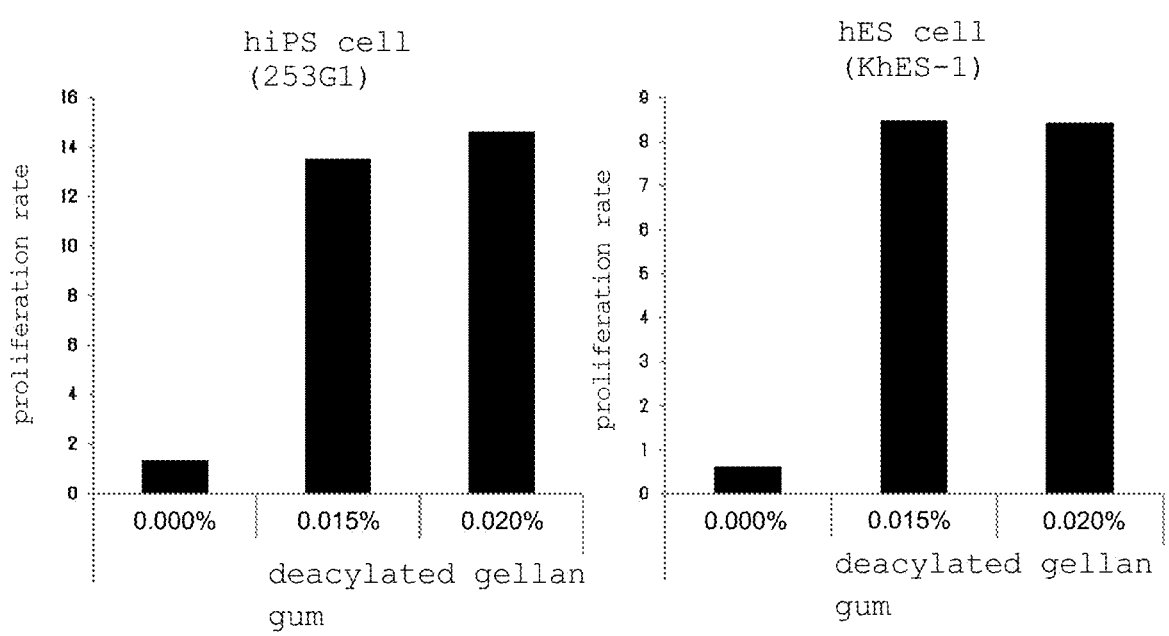
FIG. 6 is a Figure showing that, when spheres of pluripotent stem cells were cultured in the medium composition of the present invention, the pluripotent stem cells were efficiently proliferated.

Experimental Example 5: Cell Proliferation Test in Culture of Human Pluripotent Stem Cell Sphere Whether hPSCs can be cultured in a tube in a three-dimensionally suspended state was examined. hPSCs spheres (600 to 800/3 mL) prepared and passaged in the same manner as in Experimental Example 4 were plated on mTeSR medium containing deacylated gellan gum at 0.000%, 0.015% or 0.020% (w/v) in 5 mL polystyrene tubes (manufactured by BD Falcon) such that each tube has the same sphere number, and cultured in a $CO_2$ incubator (5% $CO_2$) at 37° C. for 5 days. The medium was exchanged on day 1 and day 3 after passage by adding 3-fold volume of DMEM/F-12 medium (manufactured by Sigma Ltd.) to the culture medium, sedimenting the spheres by centrifugation (100G, 3 min), and adding a new medium to the spheres. On day 5, an equal amount of DMEM/F-12 medium (manufactured by Sigma Ltd.) was added, all spheres were recovered by centrifugation (100G, 3 min) and dissociated into single cells with trypsin-EDTA solution (manufactured by Invitrogen), and the cell number was measured by NucleoCounter (manufactured by chemometec). As a result, in a medium free of deacylated gellan gum, the spheres sedimented on the bottom of the tube to form a large cell aggregate, and did not show proliferation. However, in a medium containing deacylated gellan gum at 0.015% or 0.020% (w/v), the size of the sphere grew in a three-dimensionally suspended state, and cell proliferation was found as evidenced by an about 10-fold cell number obtained on day 5 relative to the plated cell number as 1. The results are shown in FIG. 6. FIG. 6 relatively shows the cell number on day 5 to the plated cell number as 1. With human ES cells, 3,000,000 cells could be actually obtained per 3 mL on day 5 of culture in the polystyrene tube (corresponding to about 1,000,000,000 cells in 1000 mL of medium).

Figure 7:
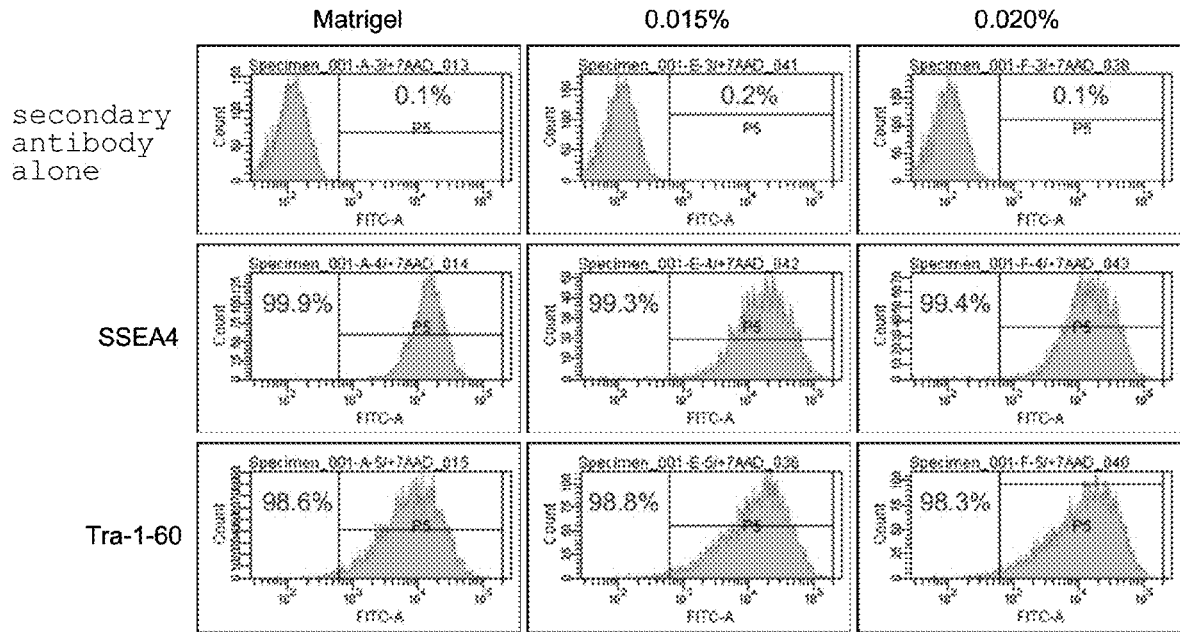
FIG. 7 is a Figure showing that pluripotent stem cells cultured in the medium composition of the present invention remained undifferentiated.
Figure 7:
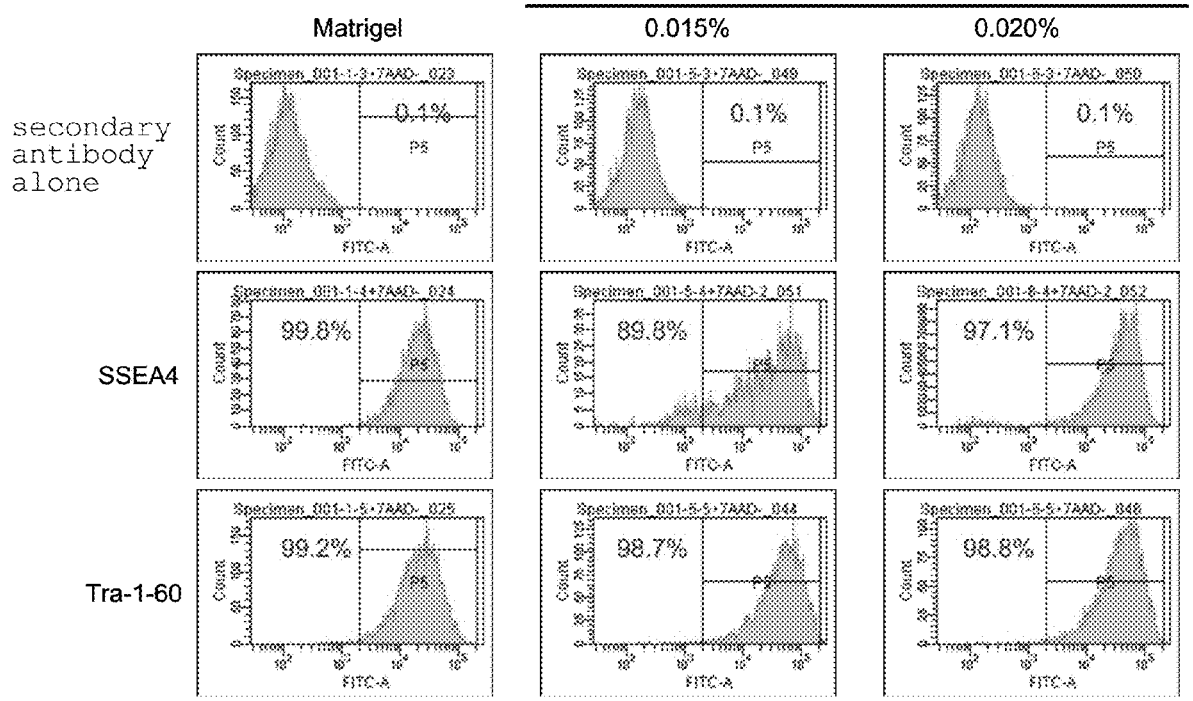

Experimental Example 6: Undifferentiation Maintenance Confirmation Test in Culture of Human Pluripotent Stem Cell Sphere hPSCs sphere cells subjected to suspension static culture in mTeSR medium containing deacylated gellan gum at 0.015% or 0.020% (w/v), the maintenance of the undifferentiation property thereof was examined by flow cytometry analysis. In a polystyrene tube in a sphere state, human ES cells (KhES-1) were passaged 3 times, human iPS cells (253G1) were passaged 4 times. The cells were recovered, stained with SSEA4 antibody (# MAB4304, manufactured by Millipore) and TRA-1-60 (# MAB4360, manufactured by Millipore) antibody, which are surface markers showing undifferentiation property of hPSCs, and the positive rate of cell staining with the antibody was evaluated using FACSCantoII (manufactured by Becton, Dickinson and Company). The results are shown in FIG. 7. As shown in FIG. 7, in both A: human iPS cells (253G1) and B: human ES cells (KhES-1), not less than 90% of the cells subjected to suspension static culture in an addition medium containing deacylated gellan gum expressed pluripotent stem cell marker, like the cells maintained on Matrigel. As a negative control, staining only with a secondary antibody was performed. From the above, it was clarified that both in human iPS cells and human ES cells, the hPSCs spheres subjected to suspension static culture in an addition medium containing deacylated gellan gum maintain the undifferentiation property.

Experimental Example 7: Property Analysis of Sphere Cultured Human Pluripotent Stem Cells—1

Using mTeSR medium (manufactured by STEM Cell Technologies) containing 0.020% (w/v) of deacylated gellan gum (KELCOGEL CG-LA, manufactured by SANSHO Co., Ltd.) prepared by a method similar to Experimental Example 3, spheres of human iPS cells (253G1) or human ES cells (KhES-1) were passage cultured 9 times in total by a method similar to Experimental Example 4, the spheres on day 1 of passage of each cell after culture were plated on mouse fetus fibroblasts. The next day, they were treated with 300 µg/mL of thymidine (manufactured by Sigma Aldrich) overnight. Successively, they were treated with 100 ng/mL of colcemid (manufactured by Nacalai Tesque), dissociated into single cells with trypsin-EDTA solution, and subjected to a hypotonic treatment with 0.075 M KCl. Thereafter, the cells were fixed with Carnoy's fixative (methanol:acetic acid=3:1).

Figure 8:
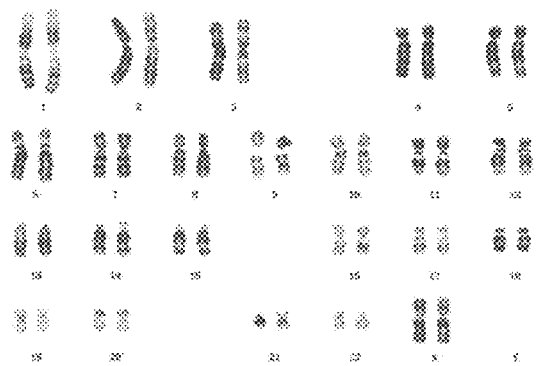
FIG. 8 is a Figure showing that pluripotent stem cells after suspension static culture in the medium composition of the present invention maintained a normal karyotype.
Figure 8:
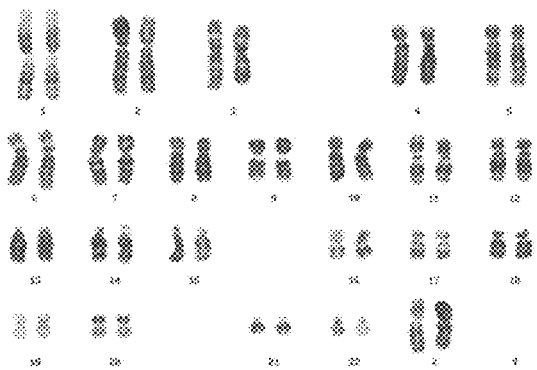

The karyotype of the fixed cells was analyzed by Q-banding method (experiments committed to Chromosome Science Labo. Ltd.). As a result, it was clarified that both human iPS cells and human ES cells subjected to suspension static culture in the medium composition of the present invention retained a normal karyotype. The results are shown in FIG. 8.

Experimental Example 8: Property Analysis of Sphere Cultured Human Pluripotent Stem Cells—2

Figure 9:
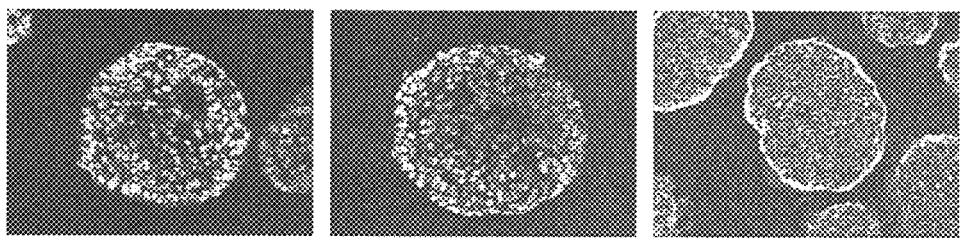
FIG. 9 is a Figure showing that pluripotent stem cells cultured in the medium composition of the present invention remained undifferentiated.

Using mTeSR medium (manufactured by STEM Cell Technologies) containing 0.020% (w/v) of deacylated gellan gum (KELCOGEL CG-LA, manufactured by SANSHO Co., Ltd.) prepared by a method similar to Experimental Example 3, spheres of human iPS cells (253G1) were passage cultured 21-22 times in total, every 5 days, by a method similar to Experimental Example 4, and the spheres after culture were fixed with 4% (w/v) para-formaldehyde (manufactured by Nacalai Tesque). They were immersed in PBS containing 20% sucrose (w/v), and embedded in an embedding agent for freezing (O.C.T compound, manufactured by Japanese cherry Finetek Japan Co., Ltd.). 12 µm-Thick sections were prepared in a cryostat (manufactured by Thermo Scientific), and stained with antibodies of NANOG (#4903, manufactured by Cell Signaling) and OCT3/4 (# sc-5279, manufactured by Santa Cruz) and SSEA4 (# MAB4304, manufactured by Millipore), showing undifferentiation of hPSCs. As a result, it was clarified that the cells subjected to suspension static culture in a medium composition containing deacylated gellan gum expressed an undifferentiation marker of pluripotent stem cells. As mentioned above, it was clarified that human iPS cell spheres subjected to suspension static culture for not less than 100 days in a medium composition containing deacylated gellan gum maintained undifferentiation property. The results are shown in FIG. 9.

Experimental Example 9: Cell Proliferation Test by Culturing Cell Line Attached onto Microcarrier Microcarrier Cytodex (registered trade mark) 1 (manufactured by GE Healthcare Life Sciences) was suspended in PBS at 0.02 g/mL, and the suspension was stood overnight. The supernatant was discarded, and the microcarrier was washed twice with fresh PBS. Thereafter, it was suspended again in PBS at 0.02 g/mL, and sterilized at 121° C. for 20 min in an autoclave. Successively, this microcarrier was washed twice with 70% ethanol and three times with PBS, and suspended in DMEM medium containing 10% (v/v) fetal bovine serum (manufactured by WAKO) at 0.02 g/mL. Using this microcarrier suspension, DMEM medium (containing 10% (v/v) fetal bovine serum, 20 mL) containing 120 mg of Cytodex (registered trade mark) 1 and 4000000 HepG2 cells was prepared, and the cell suspension was cultured in a beaker treated in advance with a silicon coating agent (manufactured by AGC TECHNO GLASS Co., Ltd.), with stirring (100 rpm) with a stirrer at 37° C. for 6 hr. At this point, adhesion of HepG2 cells to the microcarrier was confirmed with a microscope. Successively, the microcarrier with the cells adhered thereto was washed twice with DMEM medium containing 10% (v/v) fetal bovine serum, and suspended in the same medium (3 mL).

Figure 10:
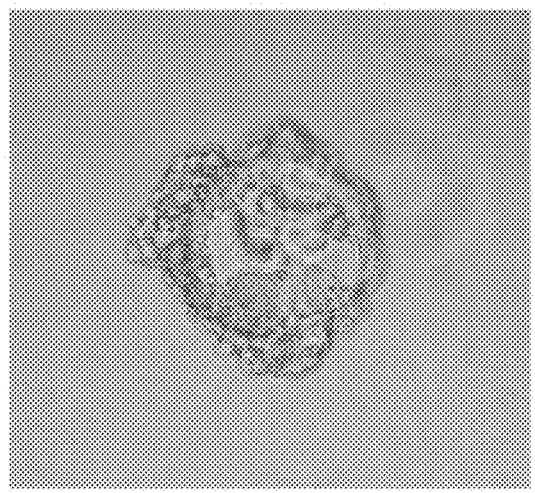
FIG. 10 is a Figure showing that, when microcarriers attached with HepG2 cells was cultured in the medium composition of the present invention, the HepG2 cells could be proliferated on the microcarrier.

The above-mentioned microcarrier suspension (300 μL) was added to each of DMEM medium (20 mL) containing 10% (v/v) fetal bovine serum and a medium composition obtained by adding, to this medium, 0.015% (w/v) deacylated gellan gum (KELCOGEL CG-LA, manufactured by SANSHO Co., Ltd.), and the mixtures were cultured at 37° C. for 3 days. In the case of the culture medium free of deacylated gellan gum, the mixtures were cultured while stirring (100 rpm) with a stirrer. After culture, the attachment state of the cells on the microcarrier was confirmed with a microscope, and the microcarrier was sedimented by centrifugation (200G, 5 min). This microcarrier was washed with PBS (10 mL), 1 mL trypsin-EDTA (ethylenediaminetetraacetic acid) solution (manufactured by WAKO) was added, and the mixture was incubated at 37° C. for 5 min. Furthermore, DMEM medium (9 mL) containing 10% (v/v) fetal bovine serum was added, and the microcarrier was removed by Cell Strainer (manufactured by BD Falcon, mesh size 70 μm). The cells were recovered from the obtained filtrate by centrifugation (200G, 5 min). The cells were suspended in a medium (500 μL), to a part thereof was added the same amount of Trypan Blue staining solution (manufactured by Invitrogen Corporation), and the number of viable cells was measured by a hemocytometer (manufactured by ERMA INC.). As a result, the culture medium free of deacylated gellan gum contained 123,000 cells, but the culture medium containing deacylated gellan gum contained 1,320,000 cells. As mentioned above, it was confirmed that the medium composition containing the structure of the particular compound of the present invention is superior in the cell proliferation promoting effect as compared to the existing media, even when the cells were cultured using a microcarrier. The attachment state of HepG2 cells after 3 days of microcarrier culture using the medium composition containing the structure of the particular compound of the present invention is shown in FIG. 10.

Experimental Example 10: Cell Suspension Test Using Cell Line-Derived Sphere

Xanthan gum (KELTROL CG, manufactured by SANSHO Co., Ltd.) was suspended in ultrapure water (Milli-Q water) to a concentration of 1% (w/v), and dissolved by stirring with heating at 90° C. Using this aqueous solution, DMEM/F-12 medium compositions having a final xanthan gum concentration of 0.1, 0.15 or 0.2% (w/v) were prepared. In addition, an aqueous solution containing 0.2% (w/v) κ-carageenan (GENUGEL WR-80-J, manufactured by SANSHO Co., Ltd.) and 0.2% (w/v) locust bean gum (GENUGUM RL-200-J, manufactured by SANSHO Co., Ltd.) was prepared by heating at 90° C. Using the aqueous solution, DMEM/F-12 medium (manufactured by Sigma Ltd.) compositions containing 0.03, 0.04 or 0.05% (w/v) κ-carageenan and locust bean gum were prepared.

Figure 11:
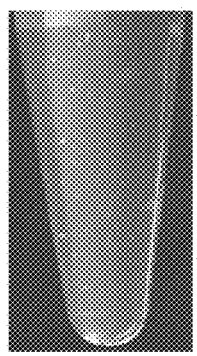
FIG. 11 is a Figure showing that, when spheres of HeLa cells were added to the medium composition of the present invention, the spheres were uniformly dispersed and were in a suspended state.
Figure 11:
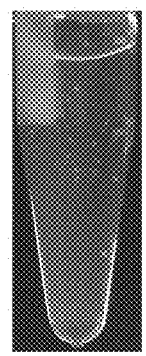

In the same manner as in Experimental Example 2, spheres of HeLa cells were formed, and several tens of the spheres were added to each medium (1 mL) prepared above, the mixture was stood still at 37° C. for 1 hr, and the suspended state of the sphere cells was visually observed. As a result, it was confirmed that the spheres of HeLa cells maintained the suspended state in any of the above-mentioned medium compositions. Furthermore, it was confirmed that addition of an equal amount of the medium to the cell suspension and centrifugation (300 to 400G, 5 min) thereof result in sedimentation and recovery of the spheres of HeLa cells. The suspended state of the spheres of HeLa cells cultured in the medium composition of the present invention is each shown in FIG. 11. In addition, the viscosity measured in the same manner as in Analysis Example 1 is shown in Tables 7 and 8.

TABLE 7

| xanthan gum concentration % (w/v) | state | viscosity (mPa · s) | HeLa cell suspension/sedimentation |
|---|---|---|---|
| 0.1 | liquid | 3.69 | Suspension |
| 0.15 | liquid | 5.46 | Suspension |
| 0.2 | liquid | 7.26 | Suspension |

TABLE 8

| κ-carageenan, locust bean gum concentration % (w/v) | state | viscosity (mPa · s) | HeLa cell suspension/sedimentation |
|---|---|---|---|
| 0.03 | liquid | 1.34 | Suspension |
| 0.04 | liquid | 1.55 | Suspension |
| 0.05 | liquid | 1.95 | Suspension |

Experimental Example 11: Cell Suspension Test Using Medium Composition Filtered with Filter A DMEM/F-12 medium composition containing 0.015% deacylated gellan gum (KELCOGEL CG-LA, manufactured by SANSHO Co., Ltd.) was prepared in the same manner as in Experimental Example 2. Successively, this medium composition (1 mL) was filtered through 70 μm filter and 40 μm filter (manufactured by BD Falcon), 30 μm filter and 20 μm filter (manufactured by AS ONE Corporation), 10 μm filter (manufactured by Partec), and 5 filter, 1.2 μm filter, 0.45 μm filter and 0.2 μm filter (manufactured by Sartorius Stedim Japan). Spheres of HepG2 cells prepared in the same manner as in Experimental Example 2 were added by about several tens spheres to the above-mentioned filtrates and stood at 37° C. for 1 hr, and the suspended state of the sphere cells was visually observed. As a result, it was confirmed that the spheres of HepG2 cells are maintained in a suspended state in the medium composition passed through a filter of not less than 10 μm, but sedimented in the medium composition passed through a filter of less than 5 μm. Furthermore, it was confirmed that centrifugation at room temperature, 300G, 5 min, or addition of an equal amount of the medium and centrifugation at room temperature, 200G, 5 min, of HepG2 cell spheres in a suspended state result in sedimentation and recovery of the spheres.

Experimental Example 12: Sphere Formation Test

Figure 12:
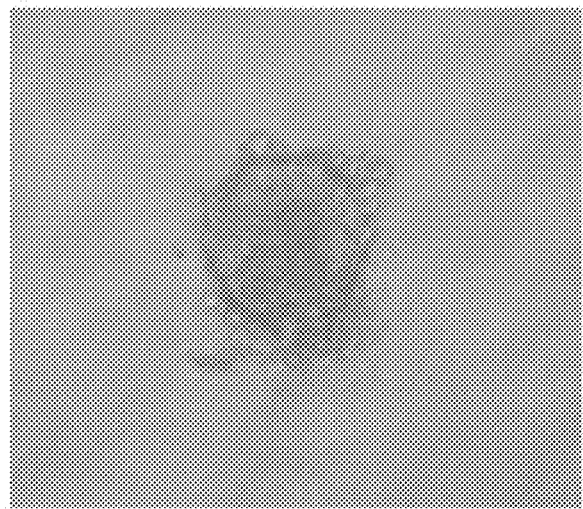
FIG. 12 is a Figure showing that spheres of HeLa cells could be formed in the medium composition of the present invention.

In the same manner as in Experimental Example 2, a composition of EMEM medium (manufactured by WAKO) containing 0.01% deacylated gellan gum (KELCOGEL CG-LA, manufactured by SANSHO Co., Ltd.) and 10% (v/v) fetal bovine serum was prepared. Successively, HeLa cells were added to a concentration of 1000 cells/mL, and dispensed to a 24-well plate (manufactured by Corning Incorporated). This plate was suspension-cultured by being stood still at 37° C. for 9 days, and formation of sphere was confirmed with a microscope. Furthermore, the sphere cell forms sediment by a centrifugation treatment (300G, 5 min), and washed once with PBS (5 mL). A 100 μL trypsin-EDTA (ethylenediaminetetraacetic acid) solution (manufactured by WAKO) was added, and the mixture was incubated at 37° C. for 5 min. Here, to the obtained cell suspension (100 μL) was added EMEM medium (100 μL) containing 10% (v/v) fetal bovine serum, to a subset of the cell suspension was added Trypan Blue staining solution (manufactured by Invitrogen Corporation) at same amount, and the number of viable cells was measured by a hemocytometer (manufactured by ERMA INC.). As a result, it was confirmed that HeLa cell increases to 170000 cells/mL. The sphere of HeLa cell formed in the medium composition of the present invention is shown in FIG. 12.

Experimental Example 13: Optical Microscope Observation of Structure

Deacylated gellan gum (KELCOGEL CG-LA, manufactured by SANSHO Co., Ltd.) was suspended in pure water to 0.4% (w/v), and dissolved by stirring with heating at 90° C. DMEM/F-12 medium (manufactured by Aldrich, 95 mL) at a 2-fold concentration was placed in a 300 mL tall beaker, an aqueous deacylated gellan gum solution (5 mL) was added with stirring with a magnetic stirrer at room temperature, and the mixture was stirred as it was for 5 min to give a medium composition containing deacylated gellan gum at a final concentration of 0.02%. Furthermore, the medium composition was stirred by a homomixer (3000 rpm) for 5 min. The prepared medium composition was observed with an optical microscope (KEYENCE Corporation, BIOREVO BZ-9000). The observed structure is shown in FIG. 13.

Experimental Example 14: Preparation by Mixing Heating Powder Medium and DAG Deacylated gellan gum (KELCOGEL CG-LA, manufactured by SANSHO Co., Ltd., 20 mg) and DMEM/F-12 medium (manufactured by Life Technologies, 1.58 g) were placed in a 200 mL Erlenmeyer flask, and pure water (100 mL) was poured therein. The mixture was sterilized at 121° C. for 20 min in an autoclave to prepare a DMEM/F-12 medium composition with a deacylated gellan gum concentration of 0.02%. To the prepared medium were added dextran beads Cytodex 1 (Size 200 μm, manufactured by GE Healthcare Life Sciences), and the dispersion state of the beads was confirmed by visual observation. For evaluation, a suspended state is ○, partial sedimentation/dispersed state is Δ, and sedimented state is x. The results are shown in Table 9.

TABLE 9

| deacylated gellan gum concentration % (w/v) | state | Cytodex1 dispersion |
|---|---|---|
| 0.05 | liquid | ○ |
| 0.02 | liquid | ○ |
| 0.01 | liquid | ○ |

Experimental Example 15: Preparation of Medium Composition Containing Polysaccharides Xanthan gum (KELTROL CG, manufactured by SANSHO Co., Ltd.) was suspended in pure water to a concentration of 0.5% (w/v), and dissolved by stirring with heating at 90° C. Similarly, 0.5% (w/v) aqueous solutions of sodium alginate (Duck alginic acid NSPM, manufactured by FOOD CHEMIFA Co., Ltd.), locust bean gum (GENUGUM RL-200-J, manufactured by SANSHO Co., Ltd.), κ-carageenan (GENUGEL WR-80-J, manufactured by SANSHO Co., Ltd.) and diutan gum (KELCO CRETE DG-F, manufactured by SANSHO Co., Ltd.) were prepared.

This aqueous solution and 0.2 or 0.1% (w/v) deacylated gellan gum solution and DMEM/F-12 medium at a 10-fold concentration were mixed, and the mixture was heated at 80° C. for 30 min, allowed to cool to room temperature, and 7.5% aqueous sodium hydrogen carbonate solution was added to prepare DMEM/F-12 medium compositions containing deacylated gellan gum at a final concentration of 0.01, 0.02% (w/v) and other polysaccharide at a final concentration of 0.1, 0.2, 0.3, 0.4% (w/v). In addition, a medium containing deacylated gellan gum was prepared as mentioned above, and a powder of methylcellulose (cP400, manufactured by WAKO) was added. The mixture was stirred in an ice bath to dissolve methylcellulose to prepare DMEM/F-12 medium compositions containing deacylated gellan gum at a final concentration of 0.01, 0.02% (w/v) and other methylcellulose at a final concentration of 0.1, 0.2, 0.3, 0.4% (w/v).

Polystyrene beads (Size 500-600 μm, manufactured by Polysciences Inc.) were added to the medium prepared above, and the dispersion state of the beads was confirmed by visual observation. For evaluation, a suspended state is ○, partial sedimentation/dispersed state is Δ, and sedimented state is x. The results are shown in Table 10.

TABLE 10

| deacylated gellan gum concentration % (w/v) | polysaccharide concentration % (w/v) | xanthan gum | alginic acid Na | locust bean gum | methylcellulose | κ-carageenan | diutan gum |
|---|---|---|---|---|---|---|---|
| 0.01 | 0.1 | ○ | ○ | ○ | x | ○ | ○ |
|  | 0.2 | ○ | ○ | ○ | Δ/x | solidified | not measured |
|  | 0.3 | ○ | ○ | ○ | Δ/x | solidified | not measured |
|  | 0.4 | ○ | ○ | ○ | Δ/x | solidified | not measured |
| 0.02 | 0.1 | ○ | ○ | ○ | ○/x | ○ | ○ |
|  | 0.2 | ○ | ○ | ○ | ○ | solidified | not measured |
|  | 0.3 | ○ | ○ | ○ | ○ | solidified | not measured |
|  | 0.4 | ○ | ○ | ○ | ○ | solidified | not measured |

Experimental Example 16: Viscosity Measurement of Medium Composition Containing Polysaccharides By a method similar to that for the polysaccharide mixture of Experimental Example 15, DMEM/F-12 media containing deacylated gellan gum at a final concentration of 0.005, 0.01% (w/v) and other polysaccharide were prepared. The final concentration of polysaccharide was set to 0.1% (w/v) for xanthan gum, sodium alginate, locust bean gum, 0.2% (w/v) for methylcellulose, and 0.05% (w/v) for κ-carageenan and diutan gum. The state of each medium composition and the viscosity measured by a method similar to that in Analysis Example 1 are shown in Tables 11-16.

TABLE 11

| xanthan gum concentration % (w/v) | deacylated gellan gum concentration % (w/v) | state | viscosity (mPa · s) |
|---|---|---|---|
| 0.1 | 0.005 | liquid | 4.36 |
| 0.1 | 0.010 | liquid | 4.59 |

TABLE 12

| sodium alginate concentration % (w/v) | deacylated gellan gum concentration % (w/v) | state | viscosity (mPa · s) |
|---|---|---|---|
| 0.1 | 0.005 | liquid | 1.53 |
| 0.1 | 0.010 | liquid | 1.75 |

TABLE 13

| locust bean gum concentration % (w/v) | deacylated gellan gum concentration % (w/v) | state | viscosity (mPa · s) |
|---|---|---|---|
| 0.1 | 0.005 | liquid | 1.92 |
| 0.1 | 0.010 | liquid | 2.36 |

TABLE 14

| methylcellulose concentration % (w/v) | deacylated gellan gum concentration % (w/v) | state | viscosity (mPa · s) |
|---|---|---|---|
| 0.2 | 0.005 | liquid | 3.36 |
| 0.2 | 0.010 | liquid | 3.81 |

TABLE 15

| κ-carageenan concentration % (w/v) | deacylated gellan gum concentration % (w/v) | state | viscosity (mPa · s) |
|---|---|---|---|
| 0.05 | 0.005 | liquid | 1.04 |
| 0.05 | 0.010 | liquid | 1.28 |

TABLE 16

| diutan gum concentration % (w/v) | deacylated gellan gum concentration % (w/v) | state | viscosity (mPa · s) |
|---|---|---|---|
| 0.1 | 0.005 | liquid | 2.76 |
| 0.1 | 0.010 | liquid | 3.04 |

Experimental Example 17: Preparation of Medium Composition with Changed Divalent Metal Ion Concentration Using DMEM/F-12 (D9785, manufactured by Aldrich) free of calcium chloride, magnesium sulfate and magnesium chloride and in the same manner as in the method of Experimental Example 14, DMEM/F-12 medium composition containing 0.02% (w/v) deacylated gellan gum was prepared. DMEM/F-12 medium compositions added with calcium chloride or magnesium sulfate, and magnesium chloride such that the final concentration was set to the defined amount of DMEM/F-12 medium were prepared. In view of the defined composition of DMEM/F-12 medium, each final concentration was set to 0.116 g/L for calcium chloride, 0.049 g/L for magnesium sulfate, and 0.061 g/L for magnesium chloride.

To the prepared medium composition were added dextran beads Cytodex 1 (manufactured by GE Healthcare Life Sciences), and the dispersion state of the beads was confirmed 2 days later by visual observation. For evaluation, a suspended state is ○, partial sedimentation/dispersed state is Δ, and sedimented state is x. The results are shown in Table 17.

TABLE 17

| deacylated gellan gum concentration % (w/v) | calcium chloride | magnesium sulfate magnesium chloride | Cytodex1 dispersion |
|---|---|---|---|
| 0.02 | + | + | ○ |
| 0.02 | + | − | ○ |
| 0.02 | − | + | Δ |
| 0.02 | − | − | X |

Experimental Example 18: Preparation of Medium Composition Later Added with Divalent Metal Ion A salt solution was prepared by dissolving 0.1% (w/v) deacylated gellan gum solution, a 5-fold concentration of DMEM/F-12 medium (not containing calcium chloride, magnesium sulfate and magnesium chloride, D9785, manufactured by Aldrich), calcium chloride (1167 mg), magnesium sulfate (489 mg) and magnesium chloride (287 mg) in pure water (300 mL). An aqueous deacylated gellan gum solution and pure water were placed in a 200 mL tall beaker, and the solution was stirred at 200 rpm using an anchor type stirring blade. Solution A, which is a mixture of the medium solution and water, was added, and the mixture was directly stirred for 10 min. Then, the salt solution was added, and 7.5% aqueous sodium hydrogen carbonate solution (1.6 mL) was further added to prepare DMEM/F-12 medium compositions containing deacylated gellan gum at a final concentration of 0.02%. The mixed amount of each solution is shown in the Table. After 4 hr from the preparation, 6 medium compositions were subjected to a dispersion evaluation of polystyrene beads and Cytodexl. The results are shown in Tables 18, 19.

TABLE 18

| | 0.1% (w/v) deacylated gellan gum aqueous solution | pure water | solution A 5-fold concentration DMEM/F-12 | pure water | salt solution calcium chloride magnesium chloride magnesium sulfate |
|---|---|---|---|---|---|
| 1 | 20 mL | 10 mL | 20 mL | 50 mL | none |
| 2 | 20 mL | 10 mL | 20 mL | 47 mL | 3 mL |
| 3 | 20 mL | 10 mL | 20 mL | 40 mL | 3 mL/water 7 mL |
| 4 | 20 mL | 30 mL | 20 mL | 30 mL | none |
| 5 | 20 mL | 30 mL | 20 mL | 27 mL | 3 mL |
| 6 | 20 mL | 30 mL | 20 mL | 20 mL | 3 mL/water 7 mL |

TABLE 19

| | deacylated gellan gum concentration % (w/v) | salt solution | polystyrene bead dispersion | Cytodex1 dispersion |
|---|---|---|---|---|
| 1 | 0.02 | − | x | x |
| 2 | 0.02 | + | ○ | ○ |
| 3 | 0.02 | + | ○ | ○ |
| 4 | 0.02 | − | x | x |
| 5 | 0.02 | + | ○ | ○ |
| 6 | 0.02 | + | ○ | ○ |

Experimental Example 19: Preparation of Various Medium Compositions

A 0.1% (w/v) deacylated gellan gum solution and a medium solution having a high concentration were prepared. As a medium solution having a high concentration, MEM having a 10-fold concentration (M0268, manufactured by Aldrich), RPMI-1640 having a 10-fold concentration (R6504, manufactured by Aldrich) and DMEM having a 5-fold concentration (high-pressure sterilization corresponding medium, manufactured by Nissui) were prepared. A 0.1% (w/v) deacylated gellan gum solution, each high concentration medium, and pure water for adjusting concentration were mixed, and the mixture was heated at 80° C. for 30 min. The mixture was allowed to cool to room temperature, and 7.5% aqueous sodium hydrogen carbonate solution was added to prepare medium compositions containing deacylated gellan gum at a final concentration of 0.01, 0.02, 0.03% (w/v).

The prepared 9 medium compositions were evaluated for the suspension and dispersion state of polystyrene beads and dextran beads Cytodex1, wherein a suspended state is ○, partial sedimentation/dispersed state is Δ, and sedimented state is x. The results are shown in Tables 20, 21.

TABLE 20

MEM medium

| deacylated gellan gum concentration % (w/v) | state | polystyrene bead dispersion | Cytodex1 dispersion |
|---|---|---|---|
| 0.01 | liquid | Δ | Δ |
| 0.02 | liquid | ○ | ○ |
| 0.03 | liquid | ○ | ○ |

TABLE 21

DMEM medium

| deacylated gellan gum concentration % (w/v) | state | polystyrene bead dispersion | Cytodex1 dispersion |
|---|---|---|---|
| 0.01 | liquid | Δ | Δ |
| 0.02 | liquid | ○ | ○ |
| 0.03 | liquid | ○ | ○ |

Experimental Example 20: Particle Size Distribution Measurement of Medium Composition Containing Deacylated Gellan Gum According to Analysis Example 1, DMEM/F-12 medium composition containing 0.038% (w/v) deacylated gellan gum was prepared. The medium was prepared by stirring at 3000 rpm and 6000 rpm for 1 min by a homomixer. The particle size distribution of the medium composition was measured by Beckman Instruments Coulter, Inc. Multisizer 4 (precise particle size distribution measuring apparatus by Coulter principle) and the median size (d50) of the volume standard particle size distribution was determined. The results are shown in Table 22.

TABLE 22

| homomixer rotation number in medium preparation | d50 (μm) |
|---|---|
| 3000 rpm | 1.709 |
| 6000 rpm | 1.499 |

Experimental Example 21: Phosphorylation of Deacylated Gellan Gum

Deacylgellan gum (1 g) and pure water (40 mL) were measured in a 100 mL glass test tube, and the mixture was heated at 100° C. for 30 min to prepare a suspension. To this suspension was added aqueous phosphoric acid solution (85%, 1 g), and the mixture was heated under reflux for 5 hr. Thereafter, it was allowed to cool to room temperature while stirring for 12 hr, and the obtained white suspension was poured into 99% ethanol (500 mL). The resulting floc white solid was collected by filtration and dried to give a pale-brown solid (0.4 g) as a phosphorylated substance of deacylgellan gum. Introduction of a phosphate group was confirmed by Fourier-transform infrared spectroscopic analysis (manufactured by SHIMADZU CORPORATION, IR-Prestage 21) (1700 cm-1; P—OH, 1296 cm-1, 1265 cm-1; P=O). The pale-brown solid was decomposed by a micro wave heating digestion apparatus (ETHOS TC, manufactured by Milestone General), and the content of the phosphorus atom was measured by an inductively coupled plasma emission spectroscopic analyzer (ICP-OES) (SPS 5520, manufactured by SII NanoTechnology). The result was 3.5 wt % (n=2).

Experimental Example 22: Preparation of Medium Composition Containing Phosphorylated Deacylated Gellan Gum An optional amount of phosphorylated deacylated gellan gum (30 mg) and DMEM/F-12 medium (manufactured by Life Technologies, 1.56 g) were placed in a 200 mL Erlenmeyer flask, and pure water (100 mL) was poured therein. The mixture was sterilized at 121° C. for 20 min in an autoclave to prepare a DMEM/F-12 medium composition having a deacylated gellan gum concentration of 0.03%. To the prepared medium were added dextran beads Cytodex 1 (manufactured by GE Healthcare Life Sciences), and the dispersion state of the beads was confirmed by visual observation. A dispersed state of the beads was found at a phosphorylated deacylated gellan gum concentration of 0.03% (w/v).

Experimental Example 23: Preparation of Medium Composition Containing Deacylated Gellan Gum An aqueous deacylated gellan gum solution and a medium solution were mixed at the rates shown in the following Table to prepare a DMEM/F-12 medium composition having a deacylated gellan gum concentration of 0.02%, and the dispersion state of polystyrene beads (Size 500-600 μm, manufactured by Polysciences Inc.) was evaluated. The results are shown in Tables 23 and 24. By standing for 1 day or longer, the styrene beads were dispersed under all conditions.

TABLE 23

| deacylated gellan gum/pure water | DMEM/F12 powder medium/pure water | standing time |
|---|---|---|
| 20 mg/10 mL | 1.56 g/90 mL | 5 min |
| 20 mg/20 mL | 1.56 g/80 mL | 5 min |
| 20 mg/30 mL | 1.56 g/70 mL | 5 min |
| 20 mg/40 mL | 1.56 g/60 mL | 6 h |
| 20 mg/50 mL | 1.56 g/50 mL | 6 h |
| 20 mg/60 mL | 1.56 g/40 mL | 6 h |
| 20 mg/70 mL | 1.56 g/30 mL | 6 h |
| 20 mg/80 mL | 1.56 g/20 mL | 1 day |
| 20 mg/90 mL | 1.56 g/10 mL | 1 day |

"DMEM/F12 powder medium/pure water" was added to "deacylated gellan gum/pure water"

TABLE 24

| deacylated gellan gum/pure water | DMEM/F12 powder medium/pure water | standing time |
|---|---|---|
| 20 mg/10 mL | 1.56 g/90 mL | 5 min |
| 20 mg/20 mL | 1.56 g/80 mL | 5 min |
| 20 mg/30 mL | 1.56 g/70 mL | 1 h |
| 20 mg/40 mL | 1.56 g/60 mL | 6 h |
| 20 mg/50 mL | 1.56 g/50 mL | 6 h |
| 20 mg/60 mL | 1.56 g/40 mL | 6 h |
| 20 mg/70 mL | 1.56 g/30 mL | 1 day |
| 20 mg/80 mL | 1.56 g/20 mL | 1 day |
| 20 mg/90 mL | 1.56 g/10 mL | 1 day |

"Deacylated gellan gum/pure water" was added to "DMEM/F12 powder medium/pure water"

Experimental Example 24: Preparation of Medium Composition Using Filter

Deacylated gellan gum (KELCOGEL CG-LA, manufactured by SANSHO Co., Ltd.) was suspended in ultrapure water (Milli-Q water) to a final concentration of 0.02 or 0.04% (w/v), and dissolved by heating at 90° C. for 30 min or at 121° C. for 20 min. Furthermore, this aqueous solution (100 mL) was filtered with a polyethersulfone membrane filter having a pore size of 0.22 (manufactured by Corning Incorporated). Successively, this filtrate was mixed with a 2- to 4-fold concentration of DMEM/F-12 medium (manufactured by Sigma Aldrich), and the mixture was shaken by a mild mixer (SI-24, manufactured by TAITEC Co., Ltd.) for 1 hr to prepare medium compositions containing deacylated gellan gum at a final concentration of 0.01 or 0.015% (w/v) (e.g., 25 mL each of 0.02% (w/v) aqueous deacylated gellan gum solution and DMEM/F-12 medium having a 2-fold concentration were mixed to prepare 0.01% (w/v) deacylated gellan gum medium composition (50 mL)). By a method similar to that in Experimental Example 2, spheres of HepG2 cells were formed, and several tens of the spheres were added to the medium (1 mL) prepared above, stood at 37° C., of the suspended state of the sphere cells was visually observed after 1 hr and one night. As a result, it was confirmed that the spheres of HepG2 cells were maintained in a suspended state in all of the above-mentioned medium composition. Furthermore, two-fold volume of the medium was added, and the cell suspension was centrifuged (500G, 5 min). It was confirmed that the spheres of HepG2 cells sedimented, and the cells can be recovered in all medium compositions. The dispersed state of the sphere after one night was confirmed by visual observation and evaluated, wherein a suspended and dispersed state is ○, partial sedimentation/dispersed state is Δ, and sedimented state is x. The evaluation results are shown in Table 25.

TABLE 25

| aqueous deacylated gellan gum solution concentration (%) | temperature (° C.) during dissolution | deacylated gellan gum concentration (%) of medium composition | suspending effect of HepG2 cells |
|---|---|---|---|
| 0.02 | 90 | 0.010 | ○ |
|  |  | 0.015 | ○ |
|  | 120 | 0.010 | ○ |
|  |  | 0.015 | ○ |
| 0.04 | 90 | 0.010 | ○ |
|  |  | 0.015 | ○ |
|  | 120 | 0.010 | ○ |
|  |  | 0.015 | ○ |

Experimental Example 25: Cell Proliferation Test by Culturing Cell Line-Derived Sphere Human embryonic kidney cell line HEK293 (manufactured by DS PHARMA BIOMEDICAL CO., LTD.) was suspended in EMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 2 days in a $CO_2$ incubator (5% $CO_2$). A suspension (10 mL) of the spheres (diameter 100-200 μm) of HEK293 cells obtained here was centrifuged (200G, 5 min) to allow for sphere sedimentation, the supernatant was removed and the sphere was suspended in 1 mL. Successively, the medium (10 mL) was added to the sphere suspension (200 μL, cell number about 200000) to suspend them and the suspension was transferred to a flat bottom tube (manufactured by BM Equipment Co., Ltd.). Similarly, using a medium composition obtained by adding 0.015% (w/v) deacylated gellan gum (KELCOGEL CG-LA, manufactured by SANSHO Co., Ltd.) to the above-mentioned medium, a sphere suspension was produced and transferred to a flat bottom tube (manufactured by BM Equipment Co., Ltd.). The medium composition added with 0.015% (w/v) deacylated gellan gum was prepared by first suspending deacylated gellan gum (KELCOGEL CG-LA, manufactured by SANSHO Co., Ltd.) in ultrapure water (Milli-Q water) to 0.3% (w/v), dissolving same by stirring with heating at 90° C., sterilizing this aqueous solution at 121° C. for 20 min in an autoclave, and adding the solution at 1/20 dilution to EMEM medium containing 10% (v/v) fetal bovine serum.

After static culture of the above-mentioned sphere suspension in a $CO_2$ incubator (5% $CO_2$) at 37° C. for 5 days, a two-fold volume of the medium was added. The mixture was centrifuged (500G, 5 min) to allow for sphere sedimentation, and the supernatant was removed. Successively, the recovered sphere was washed once with PBS (10 mL), 1 mL of trypsin-EDTA (ethylenediaminetetraacetic acid) solution (manufactured by WAKO) was added, and the mixture was incubated at 37° C. for 5 min. The above-mentioned medium (9 mL) was added, and the cells were collected by centrifugation (200G, 5 min). To a part of the obtained cell suspension (2 mL) was added the same amount of a Trypan Blue staining solution (manufactured by Invitrogen Corporation), and the numbers of the viable cells and dead cells were measured by a hemocytometer (manufactured by ERMA INC.). As a control, a medium composition free of deacylated gellan gum was produced and a similar experiment was performed.

As a result, it was confirmed that, using the medium composition of the present invention, the spheres of HEK293 cells can be cultivated in a suspended state, and the cells efficiently proliferate in the medium composition. Furthermore, the medium composition of the present invention was confirmed to show a small rate of the dead cells as compared to a medium composition free of deacylated gellan gum when the cells were proliferated, and have a superior cell proliferation promoting effect. The sphere cultured in an existing medium sedimented on the bottom of the culture container.

The relative number of the HEK293 cells is shown in Table 26, wherein the number of the cells cultured in a medium free of deacylated gellan gum is 1. In addition, the relative rate of the dead cells is shown in Table 27, wherein the rate of the dead cells cultured in a medium free of deacylated gellan gum (dead cell number/viable cell number) is 1.

TABLE 26

| deacylated gellan gum | | HEK293 cells |
| --- | --- | --- |
| absent | relative cell number | 1.0 |
| present | relative cell number | 1.6 |

TABLE 27

| deacylated gellan gum | | HEK293 cells |
| --- | --- | --- |
| absent | relative dead cell rate | 1.0 |
| present | relative dead cell rate | 0.3 |

Experimental Example 26: Cell Proliferation Test by Culturing Insect Cell

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to Sf-900 (registered trade mark) III SFM medium (manufactured by Gibco). Successively, *Spodoptera frugiperda* derived Sf9 cells (manufactured by Gibco) were inoculated to the above-mentioned medium composition added with deacylated gellan gum at 100000 cells/mL, and dispensed to the wells of a 24-well flat bottom microplate (manufactured by Corning Incorporated) at 1 mL/well. The cell suspensions were cultured by being stood still in an incubator at 25° C. for 5 days. Thereafter, a part of the culture medium was recovered, the same amount of Trypan Blue staining solution (manufactured by Invitrogen Corporation) was added, and the number of viable cells was measured by a hemocytometer (manufactured by ERMA INC.). As a control, a medium composition free of deacylated gellan gum was produced and subjected to a similar experiment.

As a result, it was confirmed that, using the medium composition of the present invention, Sf9 cell can be uniformly cultivated in a suspended state, and proliferates in the medium composition. Furthermore, it was confirmed that the medium composition of the present invention is superior in the effect of promoting cell proliferation when the cells is proliferated, as compared to a medium composition free of deacylated gellan gum. The cell number of Sf9 cells after suspension static culture for 5 days is shown in Table 28.

TABLE 28

| deacylated gellan gum | Sf9 cell number (×10000) |
| --- | --- |
| absent | 33.5 |
| present | 47.4 |

Experimental Example 27: Cell Proliferation Test by Culturing CD34 Positive Cells Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v), 20 ng/mL thrombopoietin (manufactured by WAKO) and 100 ng/mL stem cell factor (SCF, manufactured by WAKO) to StemSpan SFEM medium (manufactured by StemCell Technologies). Successively, human cord blood-derived CD34 positive cells (manufactured by Lonza) were inoculated to the above-mentioned medium composition added with deacylated gellan gum to 10000 cells/mL, and dispensed to the wells of a 24-well flat bottom microplate (manufactured by Corning Incorporated) at 1 mL/well. The cell suspensions were subjected to static culture at 37° C. for 7 days in a $CO_2$ incubator (5% $CO_2$). Thereafter, a part of the culture medium was recovered, the same amount of Trypan Blue staining solution (manufactured by Invitrogen Corporation) was added, and the number of viable cells was measured by a hemocytometer (manufactured by ERMA INC.). A 3-fold volume of the medium was added to the culture medium and the mixture was centrifuged (500G, 5 min) to allow for sedimentation of all cells. As a control, a medium composition free of deacylated gellan gum was produced and subjected to a similar experiment.

As a result, it was confirmed that, using the medium composition of the present invention, CD34 positive cells can be uniformly cultivated in a suspended state, and proliferates in the medium composition. Furthermore, the medium composition of the present invention was confirmed to show a cell proliferation promoting effect of the level equal to or more than that of the existing media without deacylated gellan gum. In addition, it was confirmed that centrifugation results in sedimentation of the cells and the cells can be recovered. The relative number of the cells proliferated from the CD34 positive cells after suspension static culture for 7 days, when the number of the cells cultured in a medium free of deacylated gellan gum is 1, is shown in Table 29.

TABLE 29

| deacylated gellan gum | relative cell number |
|---|---|
| absent | 1.0 |
| present | 1.2 |

Experimental Example 28: Sphere Formation Test

Figure 14:
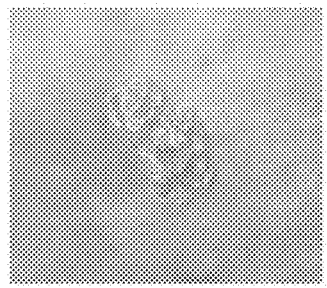
FIG. 14 is a Figure showing that spheres of HepG2 cells could be formed in the medium composition of the present invention.
Figure 15:
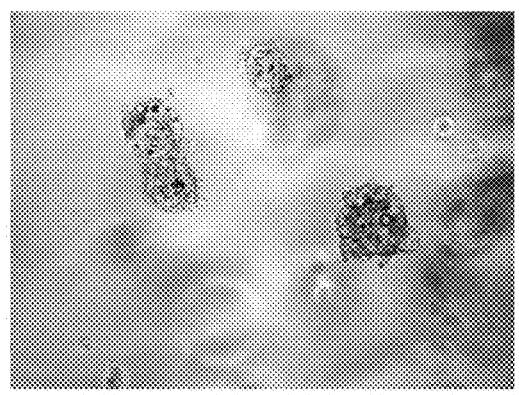
FIG. 15 is a Figure showing the suspended state of laminin-coated GEM attached with HepG2 cells, when it was cultured in the medium composition of the present invention.

In the same manner as in Experimental Example 2, a composition of DMEM medium (manufactured by WAKO) containing 0.015% deacylated gellan gum (KELCOGEL CG-LA, manufactured by SANSHO Co., Ltd.) and 10% (v/v) fetal bovine serum was prepared. Successively, HepG2 cells were added to a cell concentration of 15000 cells/mL, and dispensed by 1 mL to a 24-well plate (manufactured by Corning Incorporated). This plate was suspension-cultured by being stood still at 37° C. for 7 days, and formation of sphere was confirmed with a microscope. Furthermore, the sphere cell forms sediment by a centrifugation treatment (400G, 5 min), and washed once with PBS (5 mL). A 100 μL trypsin-EDTA (ethylenediaminetetraacetic acid) solution (manufactured by WAKO) was added, and the mixture was incubated at 37° C. for 5 min. Here, to the obtained cell suspension (100 μL) was added DMEM medium (100 μL) containing 10% (v/v) fetal bovine serum, to a subset of the cell suspension was added Trypan Blue staining solution (manufactured by Invitrogen Corporation) at same amount, and the number of viable cells was measured by a hemocytometer (manufactured by ERMA INC.). As a result, it was confirmed that HepG2 cells formed a sphere in the medium composition of the present invention and increased to 80800 cells/mL. The sphere of HepG2 cells formed in the medium composition of the present invention is shown in FIG. 14.

Experimental Example 29: Cell Suspension Test Using Cell Line-Derived Sphere

Diutan gum (KELKO-CRETE DG, manufactured by SANSHO Co., Ltd.) was suspended in ultrapure water (Milli-Q water) to a concentration of 0.3% (w/v), and dissolved by stirring with heating at 90° C. Using this aqueous solution, DMEM/F-12 medium compositions having a final diutan gum concentration of 0.1% (w/v) were prepared. In addition, an aqueous solution containing 0.5% (w/v) native-type gellan gum (KELCO gel HT, manufactured by San-Ei Gen F.F.I., Inc.) was prepared by heating at 90° C. Using the aqueous solution, DMEM/F-12 medium (manufactured by Sigma Ltd.) compositions containing 0.05 or 0.1% (w/v) native-type gellan gum was prepared.

In the same manner as in Experimental Example 2, spheres of HeLa cells were produced, and several tens of spheres were added to each medium (1 mL) prepared above, the mixture was stood still at 37° C. for 1 hr, and the suspended state of the sphere cells was visually observed. As a result, it was confirmed that the spheres of HeLa cells maintained the suspended state in any of the above-mentioned medium compositions. Furthermore, it was confirmed that centrifugation (200G, 5 min) of the cell suspension containing 0.1% (w/v) diutan gum result in sedimentation and recovery of the spheres of HeLa cells.

Experimental Example 30: Cell Suspension Test Using Magnetic Beads Having Cell Adhesion Ability—1

A suspension of GEM (registered trade mark, Global Eukaryotic Microcarrier, manufactured by GL Sciences Inc.) coated with laminin or fibronectin was dispensed by 500 μL to a 1.5 mL volume micro test tube (manufactured by Eppendorf), GEM was accumulated from the above-mentioned GEM suspension by using a magnet stand (TA4899N12, manufactured by TAMAGAWA SEIKI CO., LTD.) and the solvent was removed. Furthermore, GEM was washed twice with DMEM medium (manufactured by WAKO, 500 μL) containing 10% (v/v) fetal bovine serum, and suspended in the same medium (500 μL). This suspension was dispensed to a Sumilon cell tight plate 24F (manufactured by SUMITOMO BAKELITE), which is a cell low adhesion plate, at 50 μL per 1 well. Successively, HepG2 cells prepared separately were added at 250000 cells/mL, and the final volume was adjusted with the same medium to 500 μL/well. This cell suspension was manually stirred, and the plate was stood overnight in a $CO_2$ incubator (5% $CO_2$). After confirmation of cell adhesion on GEM with a microscope, the cell suspension was transferred to a 1.5 mL micro test tube (manufactured by Eppendorf), cell-attached GEM was accumulated the above-mentioned magnet stand and the supernatant was removed.

By a method similar to that in Experimental Example 2, a DMEM medium (manufactured by WAKO) composition containing 0.015% of deacylated gellan gum (KELCOGEL CG-LA, manufactured by SANSHO Co., Ltd.) and 10% (v/v) fetal bovine serum was prepared. This medium composition or the above medium free of deacylated gellan gum was each added by 1 mL to the HepG2 cell-attached GEM (laminin or fibronectin-coated) prepared above, suspended, and transferred to Sumilon cell tight plate 24F. Successively, this plate was stood for 6 days in a $CO_2$ incubator (5% $CO_2$), and the cell culture medium was transferred to a 1.5 mL micro test tube (manufactured by Eppendorf), the cell-attached GEM was accumulated while gently pipetting on the above-mentioned magnet stand, and the supernatant was removed. GEM was washed once with PBS (1 mL), 200 μL of trypsin-EDTA (ethylenediaminetetraacetic acid) solution (manufactured by WAKO) was added, and the mixture was incubated at 37° C. for 10 min. To 200 μL of the cell suspension obtained here was added 800 μL of DMEM medium containing 10% (v/v) fetal bovine serum, the same amount of Trypan Blue staining solution (manufactured by Invitrogen Corporation) was added to a part of the cell suspension, and the number of viable cells was measured by a hemocytometer (manufactured by ERMA INC.).

As a result, it was confirmed that, using the medium composition of the present invention, GEM adhered with HepG2 cells can be cultivated in a suspended state, and efficiently proliferates in the medium composition. Furthermore, it was confirmed that the medium composition of the present invention shows a cell proliferation promoting effect superior to that of the existing media free of deacylated gellan gum. In addition, it was confirmed that, using magnetic force, HepG2 cell-attached GEM can be collected from the medium composition of the present invention, and further, HepG2 cells can be recovered from this GEM.

The cell number of HepG2 cells when cultured for 6 days on GEM in a deacylated gellan gum-containing or -free medium is shown in Table 30. In addition, the suspended state of HepG2 cell-attached laminin-coated GEM when cultured in the medium composition of the present invention is shown in FIG. 14.

TABLE 30

| | HepG2 cell number (×10000/mL) | |
|---|---|---|
| deacylated gellan gum | laminin coated GEM | fibronectin coated GEM |
| absent | 50.0 | 54.7 |
| present | 112.3 | 94.0 |

Experimental Example 31: Cell Suspension Test Using Magnetic Beads Having Cell Adhesion Ability—2

In the same manner as in Experimental Example 30, fibronectin-coated GEM (registered trade mark, Global Eukaryotic Microcarrier, manufactured by GL Sciences Inc.) was suspended in MF-Medium (registered trade mark) mesenchymal stem cell proliferation medium (manufactured by TOYOBO CO., LTD.). This suspension was dispensed to a Sumilon cell tight plate 24F (manufactured by SUMITOMO BAKELITE), which is a cell low adhesion plate, at 50 μL per 1 well. Successively, separately prepared human bone marrow-derived mesenchymal stem cell (manufactured by Cell Applications) was added at 250000 cells/mL and, in the same manner as in Experimental Example 30, this plate was stood overnight in a $CO_2$ incubator (5% $CO_2$) to prepare GEM adhered with mesenchymal stem cells.

By a method similar to that in Experimental Example 2, an MF-Medium (registered trade mark) mesenchymal stem cell proliferation medium (manufactured by TOYOBO CO., LTD.) composition containing 0.015% of deacylated gellan gum (KELCOGEL CG-LA, manufactured by SANSHO Co., Ltd.) was prepared. This medium composition or the above medium free of deacylated gellan gum was each added by 1 mL to the mesenchymal stem cell-attached GEM (fibronectin-coated) prepared above, suspended, and transferred to Sumilon cell tight plate 24F. Successively, this plate was stood for 4 days in a $CO_2$ incubator (5% $CO_2$), and the cell culture medium was transferred to a 1.5 mL micro test tube (manufactured by Eppendorf), the cell-attached GEM was accumulated while gently pipetting on the above-mentioned magnet stand, and the supernatant was removed. GEM was washed once with PBS (1 mL), 200 μL of trypsin-EDTA (ethylenediaminetetraacetic acid) solution (manufactured by WAKO) was added, and the mixture was incubated at 37° C. for 10 min. To 200 μL of the cell suspension obtained here was added 800 μL of DMEM medium containing 10% (v/v) fetal bovine serum, the same amount of Trypan Blue staining solution (manufactured by Invitrogen Corporation) was added to a part of the cell suspension, and the number of viable cells was measured by a hemocytometer (manufactured by ERMA INC.).

As a result, it was confirmed that, using the medium composition of the present invention, GEM adhered with mesenchymal stem cells can be cultivated in a suspended state, and efficiently proliferates in the medium composition. Furthermore, it was confirmed that the medium composition of the present invention shows a cell proliferation promoting effect superior to that of the existing media without deacylated gellan gum. In addition, it was confirmed that, using magnetic force, mesenchymal stem cell-attached GEM can be collected from the medium composition of the present invention, and further the mesenchymal stem cells can be recovered from this GEM.

The cell number of mesenchymal stem cells when cultured for 4 days on GEM in a deacylated gellan gum-containing or -free medium is shown in Table 31.

TABLE 31

| deacylated gellan gum | mesenchymal stem cell number (×10000/mL) |
|---|---|
| absent | 11.3 |
| present | 20.9 |

Experimental Example 32: Cell Suspension Test Using Alginic Acid Bead

The following test was performed according to the method of an alginic acid three-dimensional culture kit manufactured by PG Research. Separately prepared HepG2 cells were added to a sodium alginate solution (manufactured by PG research, 2.5 mL) at 400000 cells/mL, and human recombinant laminin 511 (manufactured by Veritas Ltd.) was further added at 5 μg/mL to prepare a cell suspension. The cell suspension was recovered with a 5 mL syringe (manufactured by TERUMO CORPORATION) having a gavage needle, and a 22G injection needle (manufactured by TERUMO CORPORATION) was set to this syringe. Successively, the cell suspension was added by 10 drops to each well of a 24 well flat bottom microplate (manufactured by PG research) added with 2 mL each of an aqueous calcium chloride solution (PG research manufactured by). The mixture was stood for 10 min at room temperature, formation of alginic acid bead was confirmed, the calcium chloride solution was removed, PBS (2 mL) was added, and the mixture was stood at room temperature for 15 min. Furthermore, PBS was removed, DMEM medium (manufactured by WAKO, 2 mL) containing 10% (v/v) fetal bovine serum was added and the mixture was stood at room temperature for 15 min. The medium was removed, DMEM medium (manufactured by WAKO) composition containing 0.03% deacylated gellan gum (KELCOGEL CG-LA, manufactured by SANSHO Co., Ltd.) and 10% (v/v) fetal bovine serum, which was prepared by a method similar to that in Experimental Example 2, or the above medium free of deacylated gellan gum was added by 1 mL to each well, and the mixture was subjected to static culture for 8 days in a $CO_2$ incubator (5% $CO_2$). The medium was exchanged on day 4 of culture.

The cultured alginic acid beads were transferred to a 1.5 mL micro test tube (manufactured by Eppendorf) using a 1 mL tip, a sodium citrate solution (1 mL, manufactured by PG research) was added to each tube, and the mixture was stirred at room temperature for 15 min to dissolve the alginic acid beads. Successively, cells were sedimented by centrifugation at 300G for 3 min and the supernatant was removed. To the cells was added 200 μL of trypsin-EDTA (ethylenediaminetetraacetic acid) solution (manufactured by WAKO), and the mixture was incubated at 37° C. for 5 min. To the obtained cell suspension (200 μL) was added 800 μL of DMEM medium containing 10% (v/v) fetal bovine serum, and to a part of the cell suspension was added the same amount of Trypan Blue staining solution (manufactured by Invitrogen Corporation), and the number of the viable cells was measured by a hemocytometer (manufactured by ERMA INC.).

As a result, it was confirmed that, using the medium composition of the present invention, alginic acid bead-embedded HepG2 cells can be cultivated in a suspended state, and efficiently proliferates in the medium composition. Furthermore, it was confirmed that the medium composition of the present invention shows a cell proliferation promoting effect superior to that of the existing media without deacylated gellan gum.

Figure 16:
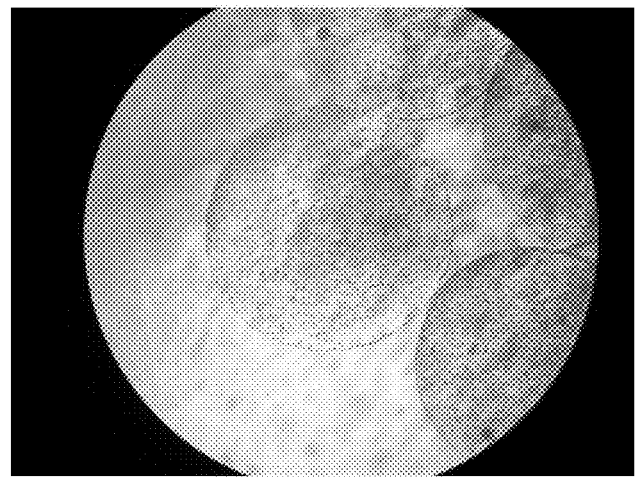
FIG. 16 is a Figure showing the suspended state of HepG2 cells embedded in alginic acid beads, when they were cultured in the medium composition of the present invention.

The cell number of HepG2 cells when cultured in alginic acid beads in a deacylated gellan gum-containing or -free medium for 8 days is shown in Table 32. In addition, the suspended state when the HepG2 cell-embedded alginic acid beads were cultured in the medium composition of the present invention is shown in FIG. 16.

TABLE 32

| deacylated gellan gum | HepG2 cell number (×10000/mL) |
|---|---|
| absent | 34.9 |
| present | 51.8 |

Experimental Example 33: Cell Suspension Test Using Collagen Gel Capsule

A: tissue culture collagen Cell matrix (registered trade mark) Type I-A (cell matrix, manufactured by Nitta Gelatin Inc.), B: 10-fold concentration of DMEM/F-12 medium (manufactured by Aldrich), C: reconstitution buffer (obtained by adding sodium hydrogen carbonate (2.2 g), HEPES (4-(2-hydroxyethyl)-1-piperazineethanesulfonic acid)) (4.77 g) to 0.05N sodium hydroxide solution (100 mL) and subjecting the mixture to filtration sterilization) were mixed at A:B:C=8:1:1 while cooling in ice. Furthermore, human recombinant laminin 511 (manufactured by Veritas Ltd.) was added at 5 μg/mL to prepare a collagen mixed solution (500 μL). To the mixed solution was added separately-prepared HepG2 cells at 200000 cell/mL, and the total amount was recovered using a 1.5 mL syringe (manufactured by TERUMO CORPORATION) with a 25G injection needle (manufactured by TERUMO CORPORATION). Successively, the cell suspension was added dropwise by one drop to a flat bottom tube (manufactured by BM Equipment Co., Ltd.) containing DMEM medium (manufactured by WAKO) (10 mL) containing 10% (v/v) fetal bovine serum and incubated in advance at 37° C. using the above-mentioned syringe. The mixture was incubated in a water bath at 37° C. for 10 min and formation of an indeterminate collagen gel capsule with a diameter of about 2 mm was confirmed, deacylated gellan gum (KELCOGEL CG-LA, manufactured by SANSHO Co., Ltd.) was added at a final concentration of 0.04% by a method similar to that in Experimental Example 2, and the above-mentioned capsule was suspended by gently stirring. Successively, the tube was subjected to static culture in a $CO_2$ incubator (5% $CO_2$) for 5 days.

PBS (25 mL) was added to a culture medium containing a collagen gel capsule, and the collagen gel capsule was sedimented by centrifugation at 400G for 5 min and the supernatant was removed. Again, PBS (25 mL) was added, the mixture was centrifuged, and the supernatant was removed to make the amount of the rest 5 mL. To this solution was added 1% (W/V) collagenase L (manufactured by Nitta Gelatin Inc., 20 μL), and the mixture was shaken at 37° C. for 2 hr. After confirming dissolution of the collagen gel, PBS (10 mL) was added, and the cells were sedimented by centrifugation at 400G for 5 min and the supernatant was removed. To the cells was added 1 mL of trypsin-EDTA (ethylenediaminetetraacetic acid) solution (manufactured by WAKO), and the mixture was incubated at 37° C. for 5 min. To the obtained cell suspension was added 4 mM of DMEM medium containing 10% (v/v) fetal bovine serum, and the cells were sedimented by centrifugation at 400G for 5 min and the supernatant was removed. The obtained cells were suspended in 2 mL of the same medium above, and to a part thereof was added the same amount of Trypan Blue staining solution (manufactured by Invitrogen Corporation), and the number of the viable cells was measured by a hemocytometer (manufactured by ERMA INC.).

As a result, it was confirmed that, using the medium composition of the present invention, collagen gel capsule embedded with HepG2 cells can be cultivated in a suspended state, and the cells efficiently proliferate in the medium composition. Furthermore, the medium composition of the present invention was confirmed to show a cell proliferation promoting effect superior to that of the existing media without deacylated gellan gum.

Figure 17:
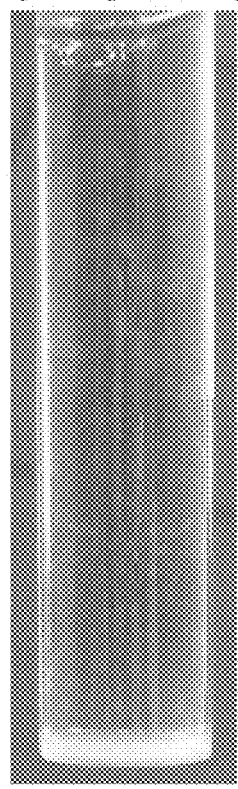
FIG. 17 is a Figure showing the suspended state of HepG2 cells embedded in a collagen gel capsule, when they were cultured in the medium composition of the present invention.

The cell number of HepG2 cells when cultured in collagen gel capsule in a deacylated gellan gum-containing or -free medium for 5 days is shown in Table 33. In addition, the suspended state when the HepG2 cell-embedded collagen gel capsule was cultured in the medium composition of the present invention is shown in FIG. 17.

TABLE 33

| deacylated gellan gum | HepG2 cell number (×10000/mL) |
|---|---|
| absent | 62.4 |
| present | 106.0 |

Experimental Example 34: Sphere Recovery Test Using Filter

A DMEM medium (manufactured by WAKO) composition containing 0.015% deacylated gellan gum (KELCOGEL CG-LA, manufactured by SANSHO Co., Ltd.) and 10% (v/v) fetal bovine serum was prepared by a method similar to that in Experimental Example 2. In addition, as a control, the same medium free of deacylated gellan gum was prepared. HepG2 cell spheres were formed by a method similar to that in Experimental Example 2, and added to the medium (1 mL) prepared above by 86000 cells, the mixture was stood at 37° C. for 1 hr, and the sphere cell suspension was visually observed. Furthermore, the cell suspension was added onto Cell Strainers (manufactured by Becton, Dickinson and Company) having a mesh size of 40 μm to trap the spheres on the filter. Successively, PBS (10 mL) was flowed from the backside of the filter to recover the spheres in a 15 mL tube, the spheres were sedimented by centrifugation at 300G for 5 min. The supernatant was removed, 500 μL of trypsin-EDTA (ethylenediaminetetraacetic acid) solution (manufactured by WAKO) was added to the spheres, and the mixture was incubated at 37° C. for 5 min. To the obtained cell suspension was added a DMEM medium (1 mL) containing 10% (v/v) fetal bovine serum, to a part thereof was added the same amount of Trypan Blue staining solution (manufactured by Invitrogen Corporation), and the number of viable cells was measured by a hemocytometer (manufactured by ERMA INC.). As a result, the sphere of HepG2 cells was confirmed to maintain a suspended state in the above-mentioned medium composition. Furthermore, it was confirmed that the cells of HepG2 cell sphere can be recovered at a recovery rate equivalent to that of a medium free of deacylated gellan gum by a filter treatment of a sphere suspension containing 0.015% deacylated gellan gum. The relative number recovered from the medium containing deacylated gellan gum is shown in Table 34, wherein the number of the HepG2 cells recovered with a filter and using a medium free of deacylated gellan gum is 1.

TABLE 34

| deacylated gellan gum | relative HepG2 cell number |
|---|---|
| absent | 1.0 |
| present | 1.1 |

Experimental Example 35: Cell Suspension Test of Sphere Using Combination Agent of Various Polysaccharides A DMEM/F-12 medium composition containing a combination of xanthan gum (KELTROL CG, manufactured by SANSHO Co., Ltd.), sodium alginate (Duck alginic acid NSPM, manufactured by FOOD CHEMIFA Co., Ltd.), locust bean gum (GENUGUM RL-200-J, manufactured by SANSHO Co., Ltd.), methylcellulose (cP400, manufactured by WAKO), κ-carageenan (GENUGEL WR-80-J, manufactured by SANSHO Co., Ltd.), pectin (GENU pectin LM-102AS, manufactured by SANSHO Co., Ltd.) or diutan gum (KELCO CRETE DG-F, manufactured by SANSHO Co., Ltd.), and deacylated gellan gum (KELCOGEL CG-LA, manufactured by SANSHO Co., Ltd.) was prepared by a method similar to that in Experimental Example 15. In the same manner as in Experimental Example 2, spheres of HepG2 cells were produced, and several tens of spheres were added to each medium (1 mL) prepared above, the mixture was stood still at 37° C. for 1 hr or one night, and the suspended state of the sphere cells was visually observed. As a result, it was confirmed that the spheres of HepG2 cells maintained the suspended state in any of the above-mentioned medium compositions. Furthermore, it was confirmed in all medium compositions that addition of a 2-fold amount of the medium and centrifugation (500G, 5 min) of the cell suspension result in sedimentation and recovery of the spheres of HepG2 cells. The dispersion state of the sphere after one night was confirmed by visual observation, wherein a suspended and dispersed state is ○, partial sedimentation/dispersed state is Δ, and sedimented state is x. The evaluation results are shown in Table 35 and Table 36. In the Table, - shows not performed.

TABLE 35

| deacylated gellan gum concentration (%) | saccharides addition concentration (%) | methylcellulose | diutan gum |
|---|---|---|---|
| 0.005 | 0.05 | — | Δ |
|  | 0.2 | Δ | — |

TABLE 36

| deacylated gellan gum concentration (%) | saccharides addition concentration (%) | xanthan gum | sodium alginate | locust bean gum | methyl-cellulose | κ-carageenan | pectin | diutan gum |
|---|---|---|---|---|---|---|---|---|
| 0.01 | 0.05 | — | — | — | — | ○ | — | ○ |
|  | 0.1 | ○ | ○ | ○ | — | — | Δ | — |
|  | 0.2 | — | — | — | ○ | — | — | — |

Comparison of Dispersibility of Beads and Cells—1

The dispersion state of dextran bead Cytodex (registered trade mark) 1 (manufactured by GE Healthcare Life Sciences) and HeLa cell sphere was compared between deacyl-gellan gum containing medium prepared above (Comparative Example) and a methylcellulose-containing medium. The results are shown in Table. Since the dispersion states of Cytodex1 and HeLa cell sphere correlate well, Cytodex1 can be used as a cell sphere model.

TABLE 37

| deacylgellan gum concentration % (w/v) | Cytodex1 suspension/ sedimentation | HeLa cell suspension/ sedimentation |
|---|---|---|
| 0.01 | suspension/partial sedimentation | suspension |
| 0.02 | suspension | suspension |
| 0.03 | suspension | suspension |
| 0.05 | suspension | suspension |

TABLE 38

| Methylcellulose % (w/v) | Cytodex1 suspension/ sedimentation | HeLa cell suspension/ sedimentation |
|---|---|---|
| 0.1 | sedimentation | sedimentation |
| 0.3 | sedimentation | sedimentation |
| 0.6 | sedimentation | sedimentation |
| 1.0 | sedimentation | sedimentation |

Comparison of Dispersibility of Beads and Cells—2

The dispersion state of polystyrene bead (Size 500-600 µm, manufactured by Polysciences Inc.) and HepG2 cell sphere was compared between the polysaccharide prepared in Experimental Example 15 and deacylgellan gum-containing medium. A suspended and dispersed state is ○, partial sedimentation/dispersed state is Δ, and sedimented state is x in the evaluation. The results are shown in Table. Since the dispersion states of polystyrene bead and HepG2 cell sphere correlate well, polystyrene bead can be used as a cell sphere model.

TABLE 39

|  |  | xanthan gum | | alginic acid Na | | locust bean gum | | diutan gum | |
| --- | --- | --- | --- | --- | --- | --- | --- | --- | --- |
|  | polysaccharide concentration | PS bead | HepG2 mass | PS bead | HepG2 mass | PS bead | HepG2 mass | PS bead | HepG2 mass |
| deacylated gellan gum concentration 0.01% (w/v) | 0.05% |  |  |  |  |  |  | ○ | ○ |
|  | 0.1% | ○ | ○ | ○ | ○ | ○ | ○ | ○ |  |
|  | 0.2% | ○ | ○ | ○ |  |  |  |  |  |

Experimental Example 36: Floating Culture Test of Rice-Derived Plant Callus

Fifty seeds of a fully ripe seed of rice Nipponbare selected with a salt solution (purchased from Koto agricultural cooperatives) were transferred to a 50 mL polystyrene tube (manufactured by BD Falcon), washed with sterilized water (50 mL), and stirred in 70% ethanol water (30 mL) for 1 min. Ethanol water was removed, Kitchen Haiter (manufactured by Kao Corporation, 30 mL) was added, and the mixture was stirred for 1 hr. Kitchen Haiter was removed, and washed 4 times with sterilized water (50 mL). The sterilized seeds were cultured on Murashige Skoog basal medium (M9274, manufactured by Sigma Aldrich) containing 2 µg/mL 2,4-dichlorophenoxyacetic acid (manufactured by Sigma Aldrich) and agar at 1.5 mL/well (24 well flat bottom microplate (manufactured by Corning Incorporated)). They were cultured under the conditions of 30° C., 16 hr dark place/8 hr dark place for 3 weeks, and cream-colored calluses (1-2 mm) grown on the seed blastocyst were harvested.

Figure 18:
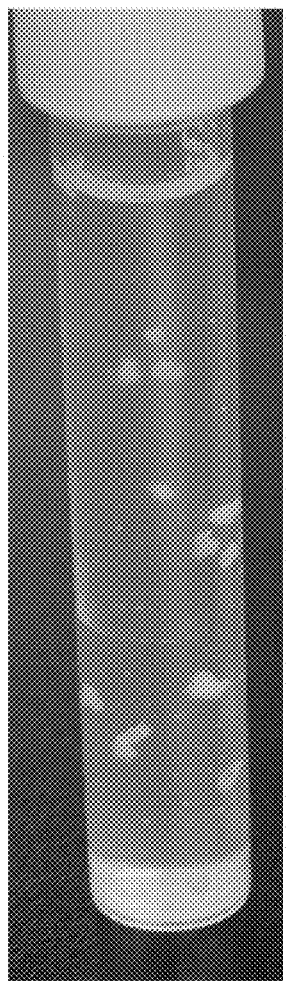
FIG. 18 is a Figure showing the suspended state of rice-derived callus when cultured in the medium composition of the present invention.

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.03% (w/v) to Murashige Skoog basal medium (M9274, manufactured by Sigma Aldrich) containing 2 µg/mL 2,4-dichlorophenoxyacetic acid (manufactured by Sigma Aldrich). 15 calluses prepared above were added to this medium composition in a 10 mL/flat bottom tube (manufactured by BM Equipment Co., Ltd.), and cultured with shaking at 25° C. for 7 days. As a result, it was confirmed that, using the medium composition of the present invention, rice-derived callus could be cultivated in a suspended state, and the calluses were maintained in the medium composition. The suspended state is shown in FIG. 18 when the rice-derived callus was cultured in the medium composition of the present invention.

Experimental Example 37: Cell Proliferation Test by Dispersing HeLa Cells

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) or 0.030% (w/v) to DMEM medium containing 10% (v/v) fetal bovine serum (manufactured by WAKO). Successively, human cervical cancer cell line HeLa (manufactured by DS PHARMA BIOMEDICAL CO., LTD.) was inoculated to the above-mentioned medium composition added with deacylated gellan gum at 50000 cells/mL, and dispensed to the wells of a 96-well flat bottom ultra low adhesion surface microplate (manufactured by Corning Incorporated, #3474) to 200 µL/well. As a negative control, HeLa cells were suspended in the above-mentioned medium free of deacylated gellan gum and the suspension was dispensed. Successively, this plate was cultured by being stood still in a $CO_2$ incubator (37° C., 5% $CO_2$) for 8 days. After culturing for 3 and 8 days, to the culture medium was added a WST-8 solution (manufactured by DOJINDO Laboratories, 20 µL), and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone. The culture medium containing the cells after 8 days of culture was stirred with a pipette and the obtained stirred solution (20 µL) was mixed with Trypan Blue stain 0.4% (manufactured by Invitrogen, 20 µL) and the cell density was measured under a microscope.

Figure 19:
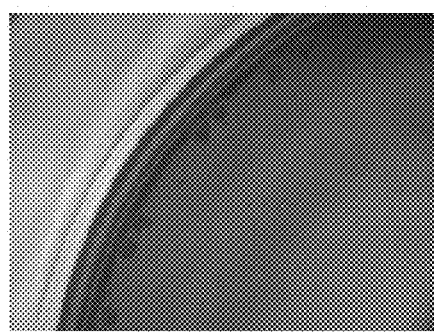
FIG. 19 is a Figure showing that, when spheres of HeLa cells were cultured in the medium composition of the present invention, the spheres were uniformly dispersed and could be cultured in a suspended state.
Figure 19:
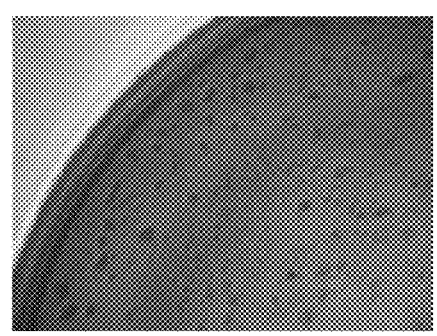

As a result, it was confirmed that, using the medium composition of the present invention, HeLa cells can be cultivated in a uniformly dispersed state without forming a cell aggregate having an excessive size, and efficiently proliferates in the medium composition. The results of microscopic observation of an aggregate of HeLa cells after culture for 8 days are shown in FIG. 19. In addition, the absorbance at 450 nm (corresponding to the number of HeLa cells) after static culture for 3, 8 days is shown in Table 40. The cell density of HeLa cells after culturing for 8 days is shown in Table 41.

TABLE 40

|  | culture day number | 3 | 8 |
| --- | --- | --- | --- |
| cell number | negative control | 0.119 | 0.191 |
|  | deacylgellan gum 0.015% | 0.426 | 0.329 |
|  | deacylgellan gum 0.030% | 0.547 | 0.423 |

TABLE 41

| experiment group | cell density ($10^4$ cells/mL) |
| --- | --- |
| negative control | 3.7 |
| deacylgellan gum 0.015% | 8.9 |
| deacylgellan gum 0.030% | 11.2 |

Experimental Example 38: Cell Proliferation Test by Dispersing A549 Cell and HCT116 Cell Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO) or McCoy's 5a medium (manufactured by DS PHARMA BIOMEDICAL CO., LTD.). Successively, human lung cancer cell line A549 (manufactured by DS PHARMA BIOMEDICAL CO., LTD.) or human colorectal cancer cell line HCT116 (manufactured by DS PHARMA BIOMEDICAL CO., LTD.) was inoculated to the above-mentioned medium composition added with deacylated gellan gum at 50000 cells/mL, and dispensed to the wells of a 96-well flat bottom ultra low adhesion surface microplate (manufactured by Corning Incorporated, #3474) at 200 μL/well. As a negative control, A549 cells and HCT116 cells were suspended in the above-mentioned medium free of deacylated gellan gum and the suspension was dispensed. Successively, this plate was cultured by being stood still in a $CO_2$ incubator (37° C., 5% $CO_2$) for 7 days. After culturing for 3, 5 and 7 days, to the culture medium was added a WST-8 solution (manufactured by DOJINDO Laboratories, 20 μL), and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone.

Figure 20:
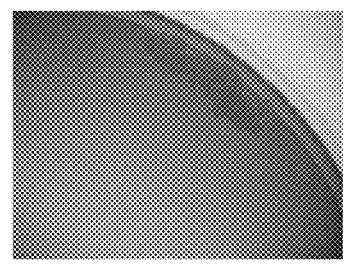
FIG. 20 is a Figure showing that, when spheres of A549 cells and HCT116 cells were cultured in the medium composition of the present invention, the spheres were uniformly dispersed and could be cultured in a suspended state.
Figure 20:
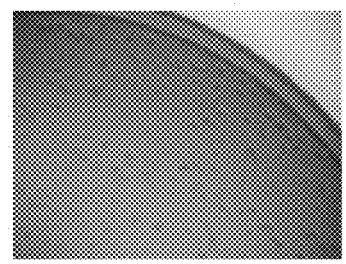
Figure 20:
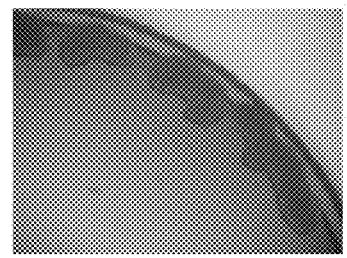
Figure 20:
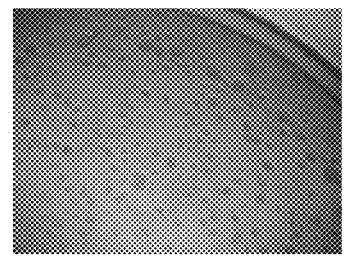

As a result, it was confirmed that, using the medium composition of the present invention, A549 cells and HCT116 cells can be cultivated in a uniformly dispersed state without forming a cell aggregate having an excessive size, and efficiently proliferate in the medium composition. The results of microscopic observation of an aggregate of A549 cells and HCT116 cells after culture for 5 days are shown in FIG. 20. In addition, after static culture for 3, 5, 7 days, the absorbance at 450 nm (corresponding to the number of A549 cells) is shown in Table 42 and the absorbance at 450 nm (corresponding to the number of HCT116 cells) is shown in Table 43.

TABLE 42

| | culture day number | 3 | 5 | 7 |
| --- | --- | --- | --- | --- |
| cell | negative control | 0.152 | 0.139 | 0.213 |
| number | deacylgellan gum | 0.435 | 1.406 | 2.041 |

TABLE 43

| | culture day number | 3 | 5 | 7 |
| --- | --- | --- | --- | --- |
| cell | negative control | 0.177 | 0.114 | 0.115 |
| number | deacylgellan gum | 1.444 | 1.959 | 2.191 |

Experimental Example 39: Cell Proliferation Test Using Low Adhesion Surface Plate with U Bottom Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO). Successively, human cervical cancer cell line HeLa (manufactured by DS PHARMA BIOMEDICAL CO., LTD.) was inoculated to the above-mentioned medium composition added with deacylated gellan gum at 50000 cells/mL, and dispensed to the wells of a 96-well U bottom low adhesion surface microplate (manufactured by SUMITOMO BAKELITE, #MS-9096U) at 200 μL/well. As a negative control, HeLa cells were suspended in the above-mentioned medium free of deacylated gellan gum and the suspension was dispensed. Successively, this plate was cultured by being stood still in a $CO_2$ incubator (37° C., 5% $CO_2$) for 7 days. To the culture medium after culturing for 2, 5 and 7 days was added a WST-8 solution (manufactured by DOJINDO Laboratories, 20 μL), and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone.

As a result, efficient proliferation also in other low adhesion plate by using the medium composition of the present invention was confirmed. The absorbance at 450 nm (corresponding to the number of HeLa cells) after static culture for 2, 5, 7 days is shown in Table 44.

TABLE 44

| | culture day number | 2 | 5 | 7 |
| --- | --- | --- | --- | --- |
| cell | negative control | 0.042 | 0.048 | 0.019 |
| number | deacylgellan gum | 0.357 | 0.488 | 0.451 |

Experimental Example 40: Cell Proliferation Test by Using Low Adhesion Surface Plate Manufactured by Other Company Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at final concentrations of 0.005% and 0.030% (w/v) to DMEM medium containing 10% (v/v) fetal bovine serum (manufactured by WAKO). Successively, human cervical cancer cell line HeLa (manufactured by DS PHARMA BIOMEDICAL CO., LTD.) was inoculated to the above-mentioned medium composition added with deacylated gellan gum at 50000 cells/mL, and dispensed to the wells of a 96-well flat bottom low adhesion surface microplate (manufactured by IWAKI, #Ez-BindShut) at 200 μL/well. As a negative control, HeLa cells were suspended in the above-mentioned medium free of deacylated gellan gum and the suspension was dispensed. Successively, this plate was cultured by being stood still in a $CO_2$ incubator (37° C., 5% $CO_2$) for 7 days. To the culture medium after culturing for 3 days was added a WST-8 solution (manufactured by DOJINDO Laboratories, 20 μL), and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone.

As a result, efficient proliferation also in other low adhesion plate by using the medium composition of the present invention was confirmed. The absorbance at 450 nm (corresponding to the number of HeLa cells) after static culture for 3 days is shown in Table 45.

TABLE 45

| | culture day number | 3 |
|---|---|---|
| cell number | negative control | 0.064 |
| | deacylgellan gum 0.005% | 0.140 |
| | deacylgellan gum 0.030% | 0.257 |

Experimental Example 41: Cell Proliferation Comparison Test with Happy Cell ASM Medium Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO). Happy Cell ASM medium (manufactured by biocroi) was adjusted with DMEM medium (manufactured by WAKO) in advance to a given concentration (mixed at 1:1). Successively, human cervical cancer cell line HeLa (manufactured by DS PHARMA BIOMEDICAL CO., LTD.) or human lung cancer cell line A549 (manufactured by DS PHARMA BIOMEDICAL CO., LTD.) was inoculated to the above-mentioned medium composition added with deacylated gellan gum or Happy Cell ASM medium composition at 50000 cells/mL, and dispensed to the wells of a 96-well flat bottom ultra low adhesion surface microplate (manufactured by Corning Incorporated, #3474) at 200 μL/well. As a negative control, HeLa cells and A549 cells were suspended in the above-mentioned medium free of deacylated gellan gum and the suspension was dispensed. Successively, the plate was cultured by being stood still in a $CO_2$ incubator (37° C., 5% $CO_2$) for 5 days. To the culture medium after culturing for 3 and 5 days was added a WST-8 solution (manufactured by DOJINDO Laboratories, 20 μL), and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone.

As a result, it was confirmed that, using the medium composition of the present invention, the cell efficiently proliferated in the medium composition as compared to Happy Cell ASM. The absorbance at 450 nm (corresponding to the number of HeLa cells) after static culture for 3, 5 days is shown in Table 46 and the absorbance at 450 nm (corresponding to the number of A549 cells) is shown in Table 47.

TABLE 46

| | culture day number | 3 | 5 |
|---|---|---|---|
| cell number | negative control | 0.111 | 0.091 |
| | deacylgellan gum | 0.288 | 0.325 |
| | Happy Cell ASM | 0.074 | 0.063 |

TABLE 47

| | culture day number | 3 | 5 |
|---|---|---|---|
| cell number | negative control | 0.244 | 0.262 |
| | deacylgellan gum | 0.696 | 2.177 |
| | Happy Cell ASM | 0.286 | 0.546 |

Experimental Example 42: Cell Proliferation Test Using Other Polysaccharides

Diutan gum (KELCO CRETE DG-F, manufactured by SANSHO Co., Ltd.) was suspended in ultrapure water (Milli-Q water) to 1.5% (w/v), and dissolved by stirring with heating at 90° C. This aqueous solution was sterilized at 121° C. for 20 min in an autoclave. Using this solution, a medium composition was prepared by adding diutan gum at final concentrations of 0.2% and 0.3% (w/v) to DMEM medium (manufactured by NISSUI PHARMACEUTICAL CO., LTD.) containing 10% (v/v) fetal bovine serum. Successively, human lung cancer cell line A549 (manufactured by DS PHARMA BIOMEDICAL CO., LTD.) was inoculated to the above-mentioned medium composition added with diutan gum at 50000 cells/mL, and dispensed to the wells of a 96-well flat bottom ultra low adhesion surface microplate (manufactured by Corning Incorporated, #3474) at 200 μL/well. As a negative control, A549 cells were suspended in the above-mentioned medium free of diutan gum and the suspension was dispensed. Successively, this plate was cultured by being stood still in a $CO_2$ incubator (37° C., 5% $CO_2$) for 3 days. To the culture medium after culturing for 3 days was added a WST-8 solution (manufactured by DOJINDO Laboratories, 20 μL), and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone.

As a result, efficient proliferation in the medium composition of the present invention containing other polysaccharides was confirmed. The absorbance at 450 nm (corresponding to the number of A549 cells) after static culture for 3 days is shown in Table 48.

TABLE 48

| | culture day number | 3 |
|---|---|---|
| cell number | negative control | 0.696 |
| | diutan gum 0.1% | 1.781 |
| | diutan gum 0.030% | 2.367 |

Experimental Example 43: Cell Proliferation Test Using Various Anticancer Drugs

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.030% (w/v) and various anticancer drugs at final concentrations of 0.001, 0.01, 0.1, 1 μM to DMEM medium containing 10% (v/v) fetal bovine serum (manufactured by WAKO). The anticancer drug used was Adriamycin (manufactured by WAKO), Paclitaxel (manufactured by WAKO) or Mitomycin C (manufactured by WAKO). Successively, human cervical cancer cell line HeLa (manufactured by DS PHARMA BIOMEDICAL CO., LTD.) was inoculated to the above-mentioned medium composition added with deacylated gellan gum at 50000 cells/mL, and dispensed to the wells of a 96-well flat bottom ultra low adhesion surface microplate (manufactured by Corning Incorporated, #3474) at 200 μL/well.

As without addition, HeLa cells were suspended in the above-mentioned medium containing only deacylated gellan gum at a final concentration of 0.030% (w/v) and the suspension was dispensed. Successively, this plate was cultured by being stood still in a $CO_2$ incubator (37° C., 5% $CO_2$) for 7 days. After culturing for 3, 5, 7 days, to the culture medium was added a WST-8 solution (manufactured by DOJINDO Laboratories, 20 μL), and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone. The culture medium containing the cells after 5 days of culture was stirred with a pipette and the obtained stirred solution (20 μL) was mixed with Trypan Blue stain 0.4% (manufactured by Invitrogen, 20 μL) and the cell density was measured under a microscope.

As a result, it was confirmed that anticancer drugs can be efficiently evaluated by the cell proliferation test method using the medium composition of the present invention. In addition, the absorbance at 450 nm (corresponding to the number of HeLa cells) after static culture for 3, 5, 7 days is shown in Table 49. The cell density of HeLa cells 5 days later is shown in Table 50.

TABLE 49

| | culture day number | 3 | 5 | 7 |
|---|---|---|---|---|
| cell number | without addition | 0.200 | 0.254 | 0.242 |
| | Adriamycin 0.001 μM | 0.237 | 0.246 | 0.184 |
| | Adriamycin 0.01 μM | 0.230 | 0.098 | 0.068 |
| | Adriamycin 0.1 μM | 0.037 | 0.005 | <0 |
| | Adriamycin 1 μM | <0 | <0 | <0 |
| | Paclitaxel 0.001 μM | 0.276 | 0.223 | 0.222 |
| | Paclitaxel 0.01 μM | 0.019 | <0 | <0 |
| | Paclitaxel 0.1 μM | <0 | <0 | <0 |
| | Paclitaxel 1 μM | <0 | <0 | <0 |
| | Mitomycin C 0.01 μM | 0.089 | 0.016 | <0 |
| | Mitomycin C 0.1 μM | 0.032 | <0 | <0 |
| | Mitomycin C 1 μM | <0 | <0 | <0 |

TABLE 50

| experiment group | cell density ($10^4$ cells/mL) |
|---|---|
| without addition | 4.8 |
| Adriamycin 0.001 μM | 5.1 |
| Adriamycin 0.01 μM | 2.6 |
| Adriamycin 0.1 μM | 1.7 |
| Adriamycin 1 μM | 0.6 |
| Paclitaxel 0.001 μM | 5.3 |
| Paclitaxel 0.01 μM | 1.6 |
| Paclitaxel 0.1 μM | 0.9 |
| Paclitaxel 1 μM | 0.2 |
| Mitomycin C 0.01 μM | 1.0 |
| Mitomycin C 0.1 μM | 0.4 |
| Mitomycin C 1 μM | 0.1 |

Experimental Example 44: Maintenance and Function Test of Human Primary Hepatocytes Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% or 0.030% (w/v) to HBM medium (manufactured by Lonza Japan) added with additives (HCM single Quots (registered trade mark), BSA-Fatty acid free, EGF, Ascorbic acid, Transferrin, Insulin, GA-1000, Hydrocortisone 21 hemisuccinate; Lonza Japan). Successively, the frozen human primary hepatocytes (manufactured by Xenotech) were inoculated to the above-mentioned medium composition added with deacylated gellan gum at 250000 cells/mL, and dispensed to the wells of a 96-well U bottom ultra low adhesion surface microplate (manufactured by SUMITOMO BAKELITE, PrimeSurface, MS-9096U) at 200 μL/well. As a negative control, human primary hepatocytes were suspended in the above-mentioned medium free of deacylated gellan gum and the suspension was dispensed. Successively, this plate was cultured by being stood still in a $CO_2$ incubator (37° C., 5% $CO_2$) for 3 days.

1. Measurement of Number of Viable Cells

To the culture medium after culturing for 4 hr, 8 hr, 1 day was added a WST-8 solution (manufactured by DOJINDO Laboratories, 20 μL), and the mixture was incubated at 37° C. for 100 min. The absorbance at 450 nm was measured by an absorbance spectrometer (manufactured by Molecular Devices, SPECTRA MAX 190) to measure the number of viable cells.

2. Analysis of Secretion Amount of Albumin

After culturing for 3 days, the culture medium containing hepatocytes was recovered, and the culture supernatant was recovered by centrifugation (400 g, 3 min). The concentration of human albumin in the medium was measured using an Albumin ELISA Quantitation kit (manufactured by Bethyl Laboratories).

3. mRNA Expression Analysis by Real-Time PCR Method

The culture medium containing hepatocytes after culturing for 8 hr was recovered, and the cells were recovered by centrifugation (400 g, 3 min). The total RNA was extracted from the cells using RNeasy Mini kit (manufactured by QIAGEN). Using the total RNA and PrimeScript (registered trade mark) RT Master Mix (manufactured by Takara Bio Inc.), a reverse transcription reaction was performed using GeneAmp PCR System 9700 (manufactured by Applied Biosystems) to synthesize cDNA. As each cDNA sample used for PCR reaction was obtained by dispensing and diluting 1/10 with sterilized water. In addition, as a sample to be used for calibration curve, cDNA dispensed and mixed was used, and set within the quantification range of 1/3 to 1/243 dilution at 3-fold common ratio. The PCR reaction was performed using each cDNA sample, calibration sample, Premix Ex Taq (registered trade mark) (manufactured by Takara Bio Inc.) and various Taqman probes (manufactured by Applied Biosystems), and 7500 Real-time PCR System (manufactured by Applied Biosystems). The specificity was calculated using mRNA of GAPDH as an endogenous control, expression of each mRNA was corrected with the value of GAPDH (Glyceraldehyde 3-phosphate dehydrogenase), and the negative control as 100%.

Each probe (manufactured by Applied Biosystems) used is shown below.
GAPDH: H599999905
Albumin: HS99999922
Cyp3A4: H500604506
Cyp2C9: H502383631
PXR (Pregnane X receptor): H501114267
ApoA1 (Apolipoprotein A1): H500163641

Figure 21:
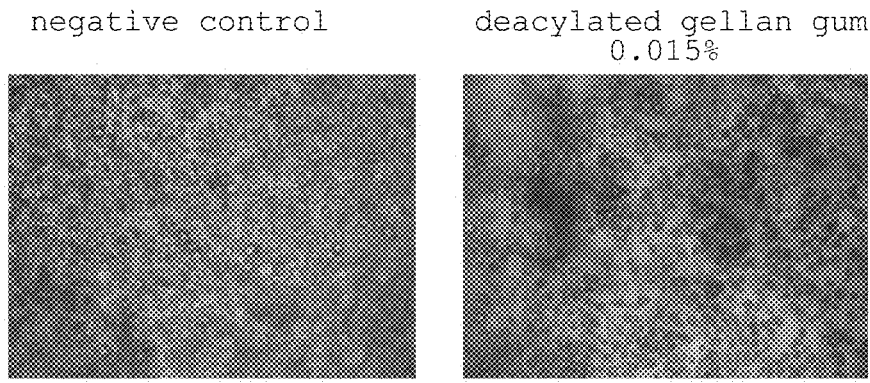
FIG. 21 is a Figure showing that, when human primary hepatocytes were cultured in the medium composition of the present invention, spheres were formed and could be cultured.

As a result, the medium composition of the present invention was confirmed to have an effect of maintaining human primary hepatocytes in a dispersed state and suppressing a decrease in the viable cell number by protection. Also, it was confirmed that the medium composition shows a higher albumin producing ability and a higher mRNA group expressing ability relating to the pharmacokinetics than the negative control. The absorbance at 450 nm (corresponding to the number of human primary hepatocytes) after static culture for 4 hr, 8 hr, 1 day is shown in Table 51. The albumin value of the culture supernatant after static culture for 3 days is shown in Table 52. In addition, each mRNA expression value based on the negative control after static culture for 8 hr as 100% is shown in Table 53. The cell state when human primary hepatocytes were cultured for 4 hr is shown in FIG. 21.

TABLE 51

| | culture day number | 4 hr | 8 hr | 1 day |
|---|---|---|---|---|
| cell number | negative control | 0.763 | 0.470 | 0.267 |
| | deacylgellan gum 0.015% | 1.223 | 0.779 | 0.376 |
| | deacylgellan gum 0.030% | 0.918 | 0.739 | 0.352 |

TABLE 52

| experiment group | Albumin (ng/mL) |
|---|---|
| negative control | 452 |
| deacylgellan gum 0.015% | 614 |
| deacylgellan gum 0.030% | 685 |

TABLE 53

| | negative control | deacylgellan gum 0.015% | deacylgellan gum 0.030% |
|---|---|---|---|
| Albumin | 100 | 124 | 135 |
| Cyp3A4 | 100 | 101 | 113 |
| Cyp2C9 | 100 | 106 | 125 |
| PXR | 100 | 117 | 202 |
| ApoA1 | 100 | 95 | 153 |

Experimental Example 45: Maintenance and Function Test of Cynomolgus Monkey Primary Hepatocytes Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% or 0.030% (w/v) to HBM medium (manufactured by Lonza Japan) added with additives (HCM single Quots (registered trade mark), BSA-Fatty acid free, EGF, Ascorbic acid, Transferrin, Insulin, GA-1000, Hydrocortisone 21 hemisuccinate; Lonza Japan). Successively, the frozen Cynomolgus monkey primary hepatocytes (manufactured by Ina Research) were inoculated to the above-mentioned medium composition added with deacylated gellan gum at 250000 cells/mL, and dispensed to the wells of a 96-well U bottom ultra low adhesion surface microplate (manufactured by SUMITOMO BAKELITE, PrimeSurface, MS-9096U) at 200 μL/well. As a negative control, Cynomolgus monkey primary hepatocytes were suspended in the above-mentioned medium free of deacylated gellan gum and the suspension was dispensed. Successively, this plate was cultured by being stood still in a $CO_2$ incubator (37° C., 5% $CO_2$) for 3 days.

1. Measurement of Number of Viable Cells

To culture media after culturing for 4 hr, 8 hr, 1 day and 3 days was added a WST-8 solution (manufactured by DOJINDO Laboratories, 20 μL), and the mixtures were incubated at 37° C. for 100 min. The absorbance at 450 nm was measured by an absorbance spectrometer (manufactured by Molecular Devices, SPECTRA MAX 190) to measure the number of viable cells.

2. Analysis of Secretion Amount of Albumin

After culturing for 3 days, the culture medium containing hepatocytes was recovered, and the culture supernatant was recovered by centrifugation (400 g, 3 min). The concentration of human albumin in the medium was measured using an Albumin ELISA Quantitation kit (manufactured by Bethyl Laboratories).

3. Expression Analysis of mRNA by Real-Time PCR

The culture media containing hepatocytes after culturing for 1, 2, 3 days were recovered, and the cells were recovered by centrifugation (400 g, 3 min). Total RNA was extracted from the cells using RNeasy Mini kit (manufactured by QIAGEN). Using the total RNA and PrimeScript (registered trade mark) RT Master Mix (manufactured by Takara Bio Inc.), a reverse transcription reaction was performed using GeneAmp PCR System 9700 (manufactured by Applied Biosystems) to synthesize cDNA. As each cDNA sample used for PCR reaction was obtained by dispensing and diluting 1/10 with sterilized water. In addition, as a sample to be used for calibration curve, cDNA dispensed and mixed was used, and set within the quantification range of 1/3 to 1/243 dilution at 3-fold common ratio. The PCR reaction was performed using each cDNA sample, calibration sample, Premix Ex Taq (registered trade mark) (manufactured by Takara Bio Inc.) and various Taqman probes (manufactured by Applied Biosystems), and 7500 Real-time PCR System (manufactured by Applied Biosystems). The specificity was calculated using mRNA of GAPDH as an endogenous control, expression of each mRNA was amended with the value of GAPDH.

Each probe (manufactured by Applied Biosystems) used is shown below.

GAPDH: Rh02621745
Albumin: Rh02789672
ApoA1 (Apolipoprotein A1): Rh02794272

Figure 22:
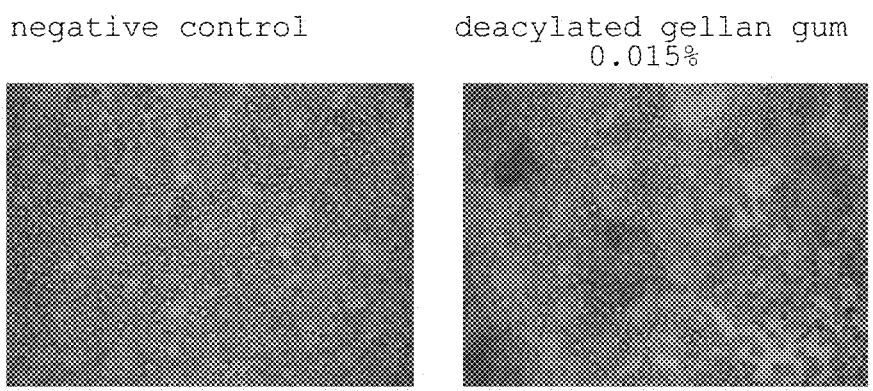
FIG. 22 is a Figure showing that, when Cynomolgus monkey primary hepatocytes were cultured in the medium composition of the present invention, spheres were formed and could be cultured.

As a result, the medium composition of the present invention was confirmed to provide a suppressive effect on a decrease in the viable cell number by protecting Cynomolgus monkey primary hepatocytes. Also, it was confirmed that the hepatocytes cultured in the medium composition shows a higher albumin producing ability and a higher mRNA group expressing ability of Albumin and ApoA1 than the negative control. The absorbance at 450 nm (corresponding to the number of Cynomolgus monkey primary hepatocytes) after static culture for 4 hr, 8 hr, 1 day, 3 days is shown in Table 54. The albumin value of the culture supernatant after static culture for 3 days is shown in Table 55. In addition, the mRNA expression value of Albumin after static culture for 2, 3 days based on the negative control as 100% is shown in Table 56, and the mRNA expression value of ApoA1 is shown in Table 57. The cell state when Cynomolgus monkey primary hepatocytes were cultured for 4 hr is shown in FIG. 22.

TABLE 54

| | culture day number | 4 hr | 8 hr | 1 day | 3 day |
|---|---|---|---|---|---|
| cell number | negative control | 0.442 | 0.328 | 0.267 | 0.240 |
| | deacylgellan gum 0.015% | 0.708 | 0.563 | 0.360 | 0.266 |
| | deacylgellan gum 0.030% | 0.662 | 0.542 | 0.381 | 0.251 |

TABLE 55

| experiment group | Albumin (ng/mL) |
|---|---|
| negative control | 420 |
| deacyl gellan gum 0.015% | 485 |
| deacyl gellan gum 0.030% | 499 |

TABLE 56

| Albumin | negative control | deacylgellan gum 0.015% | deacylgellan gum 0.030% |
|---|---|---|---|
| day 2 | 100 | 124 | 111 |
| day 3 | 100 | 132 | 153 |

TABLE 57

| ApoA1 | negative control | deacylgellan gum 0.015% | deacylgellan gum 0.030% |
|---|---|---|---|
| day 2 | 100 | 139 | 221 |
| day 3 | 100 | 118 | 105 |

Experimental Example 46: Maintenance and Function Test of Hepatocytes in Collagen-Coated Microplate Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% or 0.030% (w/v) to HBM medium (manufactured by Lonza Japan) added with additives (HCM single Quots (registered trade mark), BSA-Fatty acid free, EGF, Ascorbic acid, Transferrin, Insulin, GA-1000, Hydrocortisone 21 hemisuccinate; Lonza Japan). Successively, the frozen Cynomolgus monkey primary hepatocytes (manufactured by Ina Research) were inoculated to the above-mentioned medium composition added with deacylated gellan gum at 100000 cells/mL, and dispensed to the wells of a 96-well collagen coated microplate (manufactured by IWAKI, 4860-010) at 200 μL/well. As a negative control, Cynomolgus monkey primary hepatocytes were suspended in the above-mentioned medium free of deacylated gellan gum and the suspension was dispensed. Successively, this plate was cultured by being stood still in a $CO_2$ incubator (37° C., 5% $CO_2$) for 3 days.

1. Measurement of Number of Viable Cells

To the culture medium after culturing for 1 day was added a WST-8 solution (manufactured by DOJINDO Laboratories, 20 μL), and the mixture was incubated at 37° C. for 100 min. The absorbance at 450 nm was measured by an absorbance spectrometer (manufactured by Molecular Devices, SPECTRA MAX 190) to measure the number of viable cells.

2. Analysis of Amount of Albumin to be Secreted

After culturing for 3 days, the culture medium containing hepatocytes was recovered, and a culture supernatant was recovered by centrifugation (400 g, 3 min). The concentration of human albumin in the medium was measured using an Albumin ELISA Quantitation kit (manufactured by Bethyl Laboratories).

As a result, it was confirmed that, using the medium composition of the present invention, protection of the primary hepatocytes in the medium composition suppresses a decrease in the viable cell number even when a collagen-coated plate is used. Also, it was confirmed that the medium composition shows higher albumin production ability than the negative control. The absorbance at 450 nm (corresponding to the number of Cynomolgus monkey primary hepatocytes) after static culture for 1 day is shown in Table 58. In addition, the albumin value of the culture supernatant after static culture for 3 days is shown in Table 59.

TABLE 58

| | culture day number | 1 day |
|---|---|---|
| cell number | negative control | 0.038 |
| | deacylgellan gum 0.015% | 0.067 |
| | deacylgellan gum 0.030% | 0.087 |

TABLE 59

| experiment group | Albumin (ng/mL) |
|---|---|
| negative control | 97 |
| deacylgellan gum 0.015% | 161 |
| deacylgellan gum 0.030% | 157 |

Experimental Example 47: Comparison Test with Happy Cell ASM Medium

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by mixing HBM medium (manufactured by Lonza Japan) added with additives (HCM single Quots (registered trade mark), BSA-Fatty acid free, EGF, Ascorbic acid, Transferrin, Insulin, GA-1000, Hydrocortisone 21 hemisuccinate; Lonza Japan) to DMEM medium (manufactured by WAKO) at 1:1 and adding deacylated gellan gum at a final concentration of 0.015% (w/v). The Happy Cell ASM medium (manufactured by biocroi) was prepared with DMEM medium in advance to a given concentration (mixed at 1:1). Successively, the frozen human primary hepatocytes (manufactured by Xenotech) were inoculated to the above-mentioned medium composition added with deacylated gellan gum or Happy Cell ASM medium composition at 250000 cells/mL, and dispensed to the wells of a 96-well U bottom ultra low adhesion surface microplate (manufactured by SUMITOMO BAKELITE) at 200 μL/well. As a negative control, human primary hepatocytes were suspended in the above-mentioned medium free of deacylated gellan gum and the suspension was dispensed. Successively, this plate was cultured by being stood still in a $CO_2$ incubator (37° C., 5% $CO_2$) for 6 days.

1. Measurement of Number of Viable Cells

To the culture media after culturing for 2 hr, 4 hr, 8 hr, 1 day, 4 days and 6 days was added a WST-8 solution (manufactured by DOJINDO Laboratories, 20 μL), and the mixtures were incubated at 37° C. for 100 min. The absorbance at 450 nm was measured by an absorbance spectrometer (manufactured by Molecular Devices, SPECTRA MAX 190) to measure the number of viable cells.

As a result, it was confirmed that the medium composition of the present invention is superior in the effect of suppressing a decrease in the viable cell number by protection of the primary hepatocytes, as compared to Happy Cell ASM. The absorbance at 450 nm (corresponding to the number of human primary hepatocytes) after static culture for 2 hr, 4 hr, 8 hr, 1 day, 4 days, 6 days is shown in Table 60.

TABLE 60

| | | culture day number | | | | |
|---|---|---|---|---|---|---|
| | | 2 hr | 4 hr | 1 day | 4 days | 6 days |
| cell number | negative control | 1.162 | 0.544 | 0.396 | 0.336 | 0.241 |
| | deacylgellan gum 0.015% | 2.057 | 1.060 | 0.478 | 0.390 | 0.314 |
| | Happy Cell ASM | 1.184 | 0.564 | 0.368 | 0.229 | 0.223 |

Experimental Example 48: Toxicity Test of Compound to Hepatocytes

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. On the other hand, HepG2 cells was mixed with DMEM medium (manufactured by WAKO) at 100000 cells/mL, and the cell suspension was dispensed to the wells of a 96-well flat bottom ultra low adhesion surface microplate (manufactured by Corning Incorporated, #3474) at 100 μL/well. To the above-mentioned aqueous deacylated gellan gum solution was added Troglitazone (manufactured by WAKO, #71750) at each concentration, and this solution (10 μL) was added to the above-mentioned cell suspension (100 μL). By the above-mentioned treatments, a cell suspension having a DMSO concentration of 0.18% (v/v), a Troglitazone concentration of 20.0, 40.0, 60.0, 100 (μmol/L), and a deacylated gellan gum concentration of 0.015% (w/v) was prepared. Successively, this plate was cultured by being stood still in a $CO_2$ incubator (37° C., 5% $CO_2$) for 1 day.

1. Measurement of Number of Viable Cells

The culture medium (50 μL) after culturing for 1 day was dispensed to a 96-well titer plate (manufactured by Corning Incorporated), to this culture medium was added a Cell Titer-Glo (registered trade mark) reagent (manufactured by Promega, 50 μL), and the mixture was incubated at room temperature for 10 min. The luminescence intensity was measured by a multiplate reader (manufactured by Molecular Devices, FlexStation3) to measure the number of viable cells.

2. Lactic Acid Dehydrogenase (LDH) Activity Measurement

To the culture medium (100 μL) after culturing for 1 day was added DMEM medium (manufactured by WAKO, 100 μL), and the plate was centrifuged by 440G for 15 min. The supernatant (100 μL) was dispensed to a 96-well titer plate (manufactured by Corning Incorporated), a reaction mixture (100 μL) in a cytotoxicity detection kit (manufactured by Roche Applied Science) was added, and the mixture was stood under shading at room temperature for 30 min. Successively, according to the protocol of the above-mentioned kit, the absorbance at 490 nm (reference; 600 nm) was measured by an absorbance spectrometer (manufactured by Molecular Devices, SPECTRA MAX 190), whereby the rate of the disordered cell, that is, cell disorder rate (%), was measured.

As a result, it was confirmed that, using the medium composition of the present invention, Troglitazone has cytotoxicity of hepatocytes. The relative cell number and cell disorder rate (%) are shown in Table 61 when no addition condition after culturing for 1 day is 1.

TABLE 61

| culture day number | Troglitazone (μM) | | | | |
|---|---|---|---|---|---|
| | 0 | 20 | 40 | 60 | 100 |
| negative control relative cell number | 1.00 | 0.68 | 0.50 | 0.48 | 0.39 |
| cell disorder rate (%) | 0 | 2.68 | 14.7 | 22.5 | 60.7 |

Experimental Example 49: Cell Proliferation Test Using A549 Cell by ATP Quantification Method Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.005% (w/v), 0.015% (w/v) or 0.030% (w/v) to DMEM medium containing 10% (v/v) fetal bovine serum (manufactured by WAKO). Successively, human lung cancer cell line A549 (manufactured by DS PHARMA BIOMEDICAL CO., LTD.) was inoculated to the above-mentioned medium composition added with deacylated gellan gum at 100000 cells/mL, and dispensed to the wells of a 96-well flat bottom ultra low adhesion surface microplate (manufactured by Corning Incorporated, #3474) at 100 μL/well. As a negative control, A549 cells were suspended in the above-mentioned medium free of deacylated gellan gum and the suspension was dispensed. Successively, this plate was cultured by being stood still in a $CO_2$ incubator (37° C., 5% $CO_2$) for 5 days. To the culture medium after culturing for 1, 3 and 5 days was added a ATP reagent (100 μL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone. For WST-8 measurement, a WST-8 solution (manufactured by DOJINDO Laboratories, 10 μL) was added to the cells after culturing for 3 days, and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone.

As a result, it was also confirmed by the ATP measurement method that A549 cell efficiently proliferates when the medium composition of the present invention is used. The RLU value (ATP measurement, luminescence intensity) after static culture for 1, 3 and 5 days is shown in Table 62. The absorbance at 450 nm (WST-8) and RLU value (ATP measurement, luminescence intensity) after culturing for 3 days is shown in Table 63.

TABLE 62

| culture day number | | 1 | 3 | 5 |
|---|---|---|---|---|
| cell number | negative control | 7931 | 11183 | 16169 |
| | deacylgellan gum 0.005% | 7931 | 17623 | 29535 |
| | deacylgellan gum 0.015% | 8567 | 21021 | 39506 |
| | deacylgellan gum 0.030% | 7688 | 20492 | 39020 |

TABLE 63

| experiment group | WST-8 | ATP |
|---|---|---|
| negative control | 0.617 | 11183 |
| deacylgellan gum 0.005% | 0.906 | 17623 |
| deacylgellan gum 0.015% | 1.149 | 21021 |
| deacylgellan gum 0.030% | 1.239 | 20492 |

Experimental Example 50: Comparison with Single Layer Culture Method in Cell Proliferation Test Using Anticancer Drug Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO), and a medium composition free of deacylated gellan gum was prepared. Successively, human cervical cancer cell line HeLa (manufactured by DS PHARMA BIOMEDICAL CO., LTD.) was inoculated to the above-mentioned medium composition added with deacylated gellan gum at 37000 cells/mL, and dispensed to the wells of a 96-well flat bottom ultra low adhesion surface microplate (manufactured by Corning Incorporated, #3474) at 135 μL/well. In the single layer culture method, human cervical cancer cell line HeLa was inoculated to the above-mentioned medium composition free of deacylated gellan gum at 37000 cells/mL, and dispensed to the wells of a 96-well flat bottom microplate (manufactured by Corning Incorporated, #3585) at 135 μL/well. Each plate was cultured by being stood still in a $CO_2$ incubator (37° C., 5% $CO_2$). On culture day 1, medium compositions containing a 10-fold concentration of various anticancer drugs to make the final concentration 0.001 to 1 μM, and a final concentration 0.015% (w/v) of deacylated gellan gum (deacylated gellan gum addition group), and a medium composition containing a 10-fold concentration of various anticancer drugs alone (single layer culture group) were each added by 15 μL, and the cells were successively cultured for 3 days. The anticancer drug used was Adriamycin (manufactured by WAKO), Paclitaxel (manufactured by WAKO) or Mitomycin C (manufactured by WAKO). To the culture medium on day 4 was added an ATP reagent (150 μL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone. For WST-8 measurement, a WST-8 solution (manufactured by DOJINDO Laboratories, 15 μL) was added, the mixture was incubated at 37° C. for 100 min, the absorbance at 450 nm was measured by an absorbance spectrometer (manufactured by Molecular Devices, SPECTRA MAX 190), and the number of viable cells was measured by subtracting the absorbance of the medium alone.

As a result, it was found that the cell proliferation test method using the medium composition of the present invention strongly showed the efficacy of Mitomycin C as compared to the single layer culture method. The % Control value of the RLU value (ATP measurement, luminescence intensity) on day 4 of the static culture is shown in Table 64. The % Control value of the absorbance at 450 nm (WST-8 measurement) on day 4 of the static culture is shown in Table 65.

TABLE 64

| culture conditions | | single layer culture group | deacylated gellan gum addition group |
|---|---|---|---|
| % Control | DMSO | 100 | 100 |
| | Adriamycin 0.001 μM | 97 | 96 |
| | Adriamycin 0.01 μM | 97 | 81 |
| | Adriamycin 0.1 μM | 65 | 41 |
| | Adriamycin 1 μM | 5 | 15 |

TABLE 64-continued

| culture conditions | single layer culture group | deacylated gellan gum addition group |
|---|---|---|
| Paclitaxel 0.001 μM | 95 | 107 |
| Paclitaxel 0.003 μM | 36 | 34 |
| Paclitaxel 0.01 μM | 10 | 18 |
| Paclitaxel 0.03 μM | 4 | 17 |
| Mitomycin C 0.005 μM | 99 | 83 |
| Mitomycin C 0.05 μM | 89 | 48 |
| Mitomycin C 0.5 μM | 86 | 29 |

TABLE 65

| | culture conditions | single layer culture group | deacylated gellan gum addition group |
|---|---|---|---|
| % Control | DMSO | 100 | 100 |
| | Adriamycin 0.001 μM | 109 | 105 |
| | Adriamycin 0.01 μM | 107 | 86 |
| | Adriamycin 0.1 μM | 74 | 36 |
| | Adriamycin 1 μM | 6 | 4 |
| | Paclitaxel 0.001 μM | 99 | 125 |
| | Paclitaxel 0.003 μM | 32 | 33 |
| | Paclitaxel 0.01 μM | 10 | 5 |
| | Paclitaxel 0.03 μM | 5 | 3 |
| | Mitomycin C 0.005 μM | 101 | 94 |
| | Mitomycin C 0.05 μM | 83 | 37 |
| | Mitomycin C 0.5 μM | 71 | 12 |

Experimental Example 51: Comparison with Single Layer Culture Method in Cell Proliferation Test Using Agent for Inducing Apoptosis Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO), and a medium composition free of deacylated gellan gum was prepared. Successively, human cervical cancer cell line HeLa (manufactured by DS PHARMA BIOMEDICAL CO., LTD.) was inoculated to the above-mentioned medium composition added with deacylated gellan gum at 37000 cells/mL, and dispensed to the wells of a 96-well flat bottom ultra low adhesion surface microplate (manufactured by Corning Incorporated, #3474) at 135 μL/well. In the single layer culture method, human cervical cancer cell line HeLa was inoculated to the above-mentioned medium composition free of deacylated gellan gum at 37000 cells/mL, and dispensed to the wells of a 96-well flat bottom microplate (manufactured by Corning Incorporated, #3585) at 135 μL/well. Each plate was cultured by being stood still in a $CO_2$ incubator (37° C., 5% $CO_2$). On culture day 1, medium compositions containing a 10-fold concentration of various agents for inducing apoptosis to make the final concentration 0.2 to 10 μM, and a final concentration 0.015% (w/v) of deacylated gellan gum (deacylated gellan gum addition group), and a medium composition containing a 10-fold concentration of various agents for inducing apoptosis (single layer culture group) alone were each added by 15 μL, and the cells were successively cultured for 3 days. The agent for inducing apoptosis used was Apoptosis Inducer set (manufactured by Merck Millipore, APT800: Actinomycin D, Camptothecin, Cycloheximide, Dexamethasone, Etoposide). To the culture medium on day 4 was added an ATP reagent (150 μL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone. For WST-8 measurement, a WST-8 solution (manufactured by DOJINDO Laboratories, 15 μL) was added, the mixture was incubated at 37° C. for 100 min, the absorbance at 450 nm was measured by an absorbance spectrometer (manufactured by Molecular Devices, SPECTRA MAX 190), and the number of viable cells was measured by subtracting the absorbance of the medium alone.

As a result, it was found that the cell proliferation test method using the medium composition of the present invention strongly showed the efficacy of Camptothecin and Etoposide as compared to the single layer culture method. The % Control value of the RLU value (ATP measurement, luminescence intensity) on day 4 of the static culture is shown in Table 66. The % Control value of the absorbance at 450 nm (WST-8 measurement) on day 4 of the static culture is shown in Table 67.

TABLE 66

| | culture conditions | single layer culture group | deacylated gellan gum addition group |
|---|---|---|---|
| % Control | DMSO | 100 | 100 |
| | Adriamycin 1 μM | 3 | 5 |
| | Actinomycin D 1 μM | 2 | 4 |
| | Actinomycin D 10 μM | 2 | 6 |
| | Camptothecin 0.2 μM | 63 | 27 |
| | Camptothecin 2 μM | 44 | 11 |
| | Cycloheximide 10 μM | 29 | 9 |
| | Cycloheximide 100 μM | 9 | 4 |
| | Dexamethasone 1 μM | 117 | 232 |
| | Dexamethasone 10 μM | 116 | 241 |
| | Etoposide 1 μM | 64 | 35 |
| | Etoposide 10 μM | 65 | 24 |

TABLE 67

| culture conditions | | single layer culture group | deacylated gellan gum addition group |
|---|---|---|---|
| % Control | DMSO | 100 | 100 |
| | Adriamycin 1 μM | 3 | 3 |
| | Actinomycin D 1 μM | 2 | 3 |
| | Actinomycin D 10 μM | 4 | 12 |
| | Camptothecin 0.2 μM | 68 | 24 |
| | Camptothecin 2 μM | 28 | 7 |
| | Cycloheximide 10 μM | 21 | 4 |
| | Cycloheximide 100 μM | 7 | 1 |
| | Dexamethasone 1 μM | 89 | 184 |
| | Dexamethasone 10 μM | 92 | 173 |
| | Etoposide 1 μM | 68 | 39 |
| | Etoposide 10 μM | 63 | 23 |

Experimental Example 52: Comparison with Single Layer Culture Method in HeLa Cell Proliferation Test Using Trametinib and MK-2206

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO), and a medium composition free of deacylated gellan gum was prepared. Successively, human cervical cancer cell line HeLa (manufactured by DS PHARMA BIOMEDICAL CO., LTD.) was inoculated to the above-mentioned medium composition added with deacylated gellan gum at 37000 cells/mL, and dispensed to the wells of a 96-well flat bottom ultra low adhesion surface microplate (manufactured by Corning Incorporated, #3474) at 135 μL/well. In the single layer culture method, human cervical cancer cell line HeLa was inoculated to the above-mentioned medium composition free of deacylated gellan gum at 7400 cells/mL, and dispensed to the wells of a 96-well flat bottom microplate (manufactured by Corning Incorporated, #3585) at 135 μL/well. Each plate was cultured by being stood still in a $CO_2$ incubator (37° C., 5% $CO_2$). On culture day 1, medium compositions containing a 10-fold concentration of various anticancer drugs to make the final concentration 0.001 to 30 μM, and a final concentration 0.015% (w/v) of deacylated gellan gum (deacylated gellan gum addition group), and medium compositions containing only a 10-fold concentration of various anticancer drugs (single layer culture group) were each added by 15 μL, and the cells were successively cultured for 5 days. The anticancer drugs used were Trametinib (manufactured by Santa Cruz, MEK inhibitor) and MK-2206 (manufactured by Santa Cruz, Akt inhibitor). To the culture medium on day 6 was added an ATP reagent (150 μL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, it was found that the cell proliferation test method using the medium composition of the present invention strongly showed the efficacy of MK-2206 and Trametinib as compared to the single layer culture method. The % Control value of the RLU value (ATP measurement, luminescence intensity) on day 4 of the static culture is shown in Table 68.

TABLE 68

| culture conditions | | single layer culture group | deacylated gellan gum addition group |
|---|---|---|---|
| % Control | DMSO | 100 | 100 |
| | Paclitaxel 0.001 μM | 89 | 104 |
| | Paclitaxel 0.003 μM | 15 | 46 |
| | Paclitaxel 0.01 μM | 2 | 5 |
| | Trametinib 0.001 μM | 102 | 73 |
| | Trametinib 0.01 μM | 93 | 12 |
| | Trametinib 0.1 μM | 20 | 1 |
| | Trametinib 1 μM | 3 | 1 |
| | MK-2206 0.03 μM | 93 | 57 |
| | MK-2206 0.3 μM | 84 | 21 |
| | MK-2206 3 μM | 69 | 21 |
| | MK-2206 30 μM | 0 | 0 |

Experimental Example 53: Comparison with Single Layer Culture Method in A549 Cell Proliferation Test Using Trametinib and MK-2206

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO), and a medium composition free of deacylated gellan gum was prepared. Successively, human lung cancer cell line A549 (manufactured by DS PHARMA BIOMEDICAL CO., LTD.) was inoculated to the above-mentioned medium composition added with deacylated gellan gum at 14800 cells/mL, and dispensed to the wells of a 96-well flat bottom ultra low adhesion surface microplate (manufactured by Corning Incorporated, #3474) at 135 μL/well. In the single layer culture method, human lung cancer cell line A549 was inoculated to the above-mentioned medium composition free of deacylated gellan gum at 14800 cells/mL, and dispensed to the wells of a 96-well flat bottom microplate (manufactured by Corning Incorporated, #3585) at 135 μL/well. Each plate was cultured by being stood still in a $CO_2$ incubator (37° C., 5% $CO_2$). On culture day 1, medium compositions containing a 10-fold concentration of various anticancer drugs to make the final concentration 0.001 to 30 μM, and a final concentration 0.015% (w/v) of deacylated gellan gum (deacylated gellan gum addition group), and medium compositions containing only a 10-fold concentration of various anticancer drugs (single layer culture group) were each added by 15 µL, and the cells were successively cultured for 5 days. The anticancer drugs used were Trametinib (manufactured by Santa Cruz, MEK inhibitor) and MK-2206 (manufactured by Santa Cruz, Akt inhibitor). To the culture medium on day 6 was added an ATP reagent (150 µL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, it was found that the cell proliferation test method using the medium composition of the present invention strongly showed the efficacy of MK-2206 as compared to the single layer culture method. The % Control value of the RLU value (ATP measurement, luminescence intensity) on day 4 of the static culture is shown in Table 69.

TABLE 69

| culture conditions | | single layer culture group | deacylated gellan gum addition group |
|---|---|---|---|
| % Control | DMSO | 100 | 100 |
| | Paclitaxel 0.001 µM | 81 | 93 |
| | Paclitaxel 0.003 µM | 31 | 52 |
| | Paclitaxel 0.01 µM | 16 | 32 |
| | Trametinib 0.001 µM | 71 | 72 |
| | Trametinib 0.01 µM | 37 | 35 |
| | Trametinib 0.1 µM | 5 | 2 |
| | Trametinib 1 µM | 1 | 0 |
| | MK-2206 0.03 µM | 93 | 84 |
| | MK-2206 0.3 µM | 79 | 45 |
| | MK-2206 3 µM | 53 | 21 |
| | MK-2206 30 µM | 0 | 0 |

Experimental Example 54: Comparison with Single Layer Culture Method in Proliferation Action of HeLa Cell Stimulated with Human HB-EGF Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO), and a medium composition free of deacylated gellan gum was prepared. Successively, human cervical cancer cell line HeLa (manufactured by DS PHARMA BIOMEDICAL CO., LTD.) was inoculated to the above-mentioned medium composition added with deacylated gellan gum at 37000 cells/mL, and dispensed to the wells of a 96-well flat bottom ultra low adhesion surface microplate (manufactured by Corning Incorporated, #3474) at 135 µL/well. In the single layer culture method, human cervical cancer cell line HeLa was inoculated to the above-mentioned medium composition free of deacylated gellan gum at 37000 cells/mL, and dispensed to the wells of a 96-well flat bottom microplate (manufactured by Corning Incorporated, #3585) at 135 µL/well. Each plate was cultured by being stood still in a $CO_2$ incubator (37° C., 5% $CO_2$). On culture day 1, a medium composition containing a 10-fold concentration of human HB-EGF (heparin binding EGF-like growth factor, manufactured by PEPROTECH) to make the final concentration of 10, 30 and 100 ng/ml, and a final concentration 0.015% (w/v) of deacylated gellan gum (deacylated gellan gum addition group), and a medium composition containing only a 10-fold concentration of human HB-EGF (single layer culture group) were each added by 15 µL, and the cells were successively cultured for 7 days. To the culture medium on days 6 and 8 was added an ATP reagent (150 µL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, it was found that the HeLa cell proliferation test method using the medium composition of the present invention strongly showed the cell proliferation promoting effect of human HB-EGF as compared to the single layer culture method. The % Control value of the RLU value (ATP measurement, luminescence intensity) on day 6 of the static culture is shown in Table 70. The % Control value of the RLU value (ATP measurement, luminescence intensity) on day 8 of the static culture is shown in Table 71.

TABLE 70

| culture conditions day 6 | | single layer culture group | deacylated gellan gum addition group |
|---|---|---|---|
| % Control | negative control | 100 | 100 |
| | human HB-EGF 10 ng/ml | 102 | 109 |
| | human HB-EGF 30 ng/ml | 99 | 109 |
| | human HB-EGF 100 ng/ml | 105 | 133 |

TABLE 71

| culture conditions day 8 | | single layer culture group | deacylated gellan gum addition group |
|---|---|---|---|
| % Control | negative control | 100 | 100 |
| | human HB-EGF 10 ng/ml | 100 | 107 |
| | human HB-EGF 30 ng/ml | 99 | 115 |
| | human HB-EGF 100 ng/ml | 88 | 161 |

Experimental Example 55: Comparison with Single Layer Culture Method in Proliferation Action of A549 Cells Stimulated with Human HB-EGF Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO), and a medium composition free of deacylated gellan gum was prepared. Successively, human lung cancer cell line A549 (manufactured by DS PHARMA BIOMEDICAL CO., LTD.) was inoculated to the above-mentioned medium composition added with deacylated gellan gum to 14800 cells/mL, and dispensed to the wells of a 96-well flat bottom ultra low adhesion surface microplate (manufactured by Corning Incorporated, #3474) at 135 μL/well. In the single layer culture method, human lung cancer cell line A549 was inoculated to the above-mentioned medium composition free of deacylated gellan gum at 14800 cells/mL, and dispensed to the wells of a 96-well flat bottom microplate (manufactured by Corning Incorporated, #3585) at 135 μL/well. Each plate was cultured by being stood still in a $CO_2$ incubator (37° C., 5% $CO_2$). On culture day 1, a medium composition containing a 10-fold concentration of human HB-EGF (manufactured by PEPROTECH) to make the final concentration from 10, 30 and 100 ng/ml, and a final concentration 0.015% (w/v) of deacylated gellan gum (deacylated gellan gum addition group), and a medium composition containing only a 10-fold concentration of human HB-EGF (single layer culture group) were each added by 15 μL, and the cells were successively cultured for 7 days. To the culture medium on days 6 and 8 was added an ATP reagent (150 μL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, it was found that the A549 cell proliferation test method using the medium composition of the present invention strongly showed the cell proliferation promoting effect of human HB-EGF as compared to the single layer culture method. The % Control value of the RLU value (ATP measurement, luminescence intensity) on day 6 of the static culture is shown in Table 72. The % Control value of the RLU value (ATP measurement, luminescence intensity) on day 8 of the static culture is shown in Table 73.

TABLE 72

| culture conditions day 6 | | single layer culture group | deacylated gellan gum addition group |
|---|---|---|---|
| % Control | negative control | 100 | 100 |
| | human HB-EGF 10 ng/ml | 92 | 99 |
| | human HB-EGF 30 ng/ml | 95 | 115 |
| | human HB-EGF 100 ng/ml | 96 | 140 |

TABLE 73

| culture conditions day 8 | | single layer culture group | deacylated gellan gum addition group |
|---|---|---|---|
| % Control | negative control | 100 | 100 |
| | human HB-EGF 10 ng/ml | 97 | 103 |
| | human HB-EGF 30 ng/ml | 99 | 108 |
| | human HB-EGF 100 ng/ml | 100 | 128 |

Experimental Example 56: Comparison with Single Layer Culture Method in Proliferation Action of A431 Cells Stimulated with Human HB-EGF Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to EMEM medium (manufactured by DS PHARMA BIOMEDICAL CO., LTD.) containing 10% (v/v) fetal bovine serum, and a medium composition free of deacylated gellan gum was prepared. Successively, human squamous carcinoma cell line A431 (manufactured by DS PHARMA BIOMEDICAL CO., LTD.) was inoculated to the above-mentioned medium composition added with deacylated gellan gum at 37000 cells/mL, and dispensed to the wells of a 96-well flat bottom ultra low adhesion surface microplate (manufactured by Corning Incorporated, #3474) at 135 μL/well. In the single layer culture method, human squamous cell carcinoma cell line A431 was inoculated to the above-mentioned medium composition free of deacylated gellan gum at 37000 cells/mL, and dispensed to the wells of a 96-well flat bottom microplate (manufactured by Corning Incorporated, #3585) at 135 μL/well. Each plate was cultured by being stood still in a $CO_2$ incubator (37° C., 5% $CO_2$). On culture day 1, a medium composition containing a 10-fold concentration of human HB-EGF (manufactured by PEPROTECH) to make the final concentration from 10, 30 and 100 ng/ml, and a final concentration 0.015% (w/v) of deacylated gellan gum (deacylated gellan gum addition group), and a medium composition containing only a 10-fold concentration of human HB-EGF (single layer culture group) were each added by 15 μL, and the cells were successively cultured for 7 days. To the culture medium on days 6 and 8 was added an ATP reagent (150 μL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, it was found that the A431 cell proliferation test method using the medium composition of the present invention strongly showed the cell proliferation promoting effect of human HB-EGF as compared to the single layer culture method. The % Control value of the RLU value (ATP measurement, luminescence intensity) on day 6 of the static culture is shown in Table 74. The % Control value of the RLU value (ATP measurement, luminescence intensity) on day 8 of the static culture is shown in Table 75.

TABLE 74

| culture conditions day 6 | | single layer culture group | deacylated gellan gum addition group |
|---|---|---|---|
| % Control | negative control | 100 | 100 |
| | human HB-EGF 10 ng/ml | 96 | 241 |
| | human HB-EGF 30 ng/ml | 95 | 557 |
| | human HB-EGF 100 ng/ml | 83 | 1018 |

TABLE 75

| culture conditions day 8 | | single layer culture group | deacylated gellan gum addition group |
|---|---|---|---|
| % Control | negative control | 100 | 100 |
| | human HB-EGF 10 ng/ml | 105 | 370 |
| | human HB-EGF 30 ng/ml | 100 | 772 |
| | human HB-EGF 100 ng/ml | 89 | 1886 |

Experimental Example 57: Comparison with Single Layer Culture Method in Proliferation Action of SKOV3 Cells Stimulated with Human HB-EGF Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to McCoy's 5a medium (manufactured by DS PHARMA BIOMEDICAL CO., LTD.) containing 15% (v/v) fetal bovine serum, and a medium composition free of deacylated gellan gum was prepared. Successively, human ovarian cancer cell line SKOV3 (manufactured by DS PHARMA BIOMEDICAL CO., LTD.) was inoculated to the above-mentioned medium composition added with deacylated gellan gum at 37000 cells/mL, and dispensed to the wells of a 96-well flat bottom ultra low adhesion surface microplate (manufactured by Corning Incorporated, #3474) at 135 µL/well. In the single layer culture method, human ovarian cancer cell line SKOV3 was inoculated to the above-mentioned medium composition free of deacylated gellan gum at 37000 cells/mL, and dispensed to the wells of a 96-well flat bottom microplate (manufactured by Corning Incorporated, #3585) at 135 µL/well. Each plate was cultured by being stood still in a $CO_2$ incubator (37° C., 5% $CO_2$). On culture day 1, a medium composition containing a 10-fold concentration of human HB-EGF (manufactured by PEPROTECH) to make the final concentration from 10, 30 and 100 ng/ml, and a final concentration 0.015% (w/v) of deacylated gellan gum (deacylated gellan gum addition group), and a medium composition containing only a 10-fold concentration of human HB-EGF (single layer culture group) were each added by 15 µL, and the cells were successively cultured for 8 days. To the culture medium on days 6 and 9 was added an ATP reagent (150 µL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, it was found that the SKOV3 cell proliferation test method using the medium composition of the present invention strongly showed the cell proliferation promoting effect of human HB-EGF as compared to the single layer culture method. The % Control value of the RLU value (ATP measurement, luminescence intensity) on day 6 of the static culture is shown in Table 76. The % Control value of the RLU value (ATP measurement, luminescence intensity) on day 9 of the static culture is shown in Table 77.

TABLE 76

| culture conditions day 6 | | single layer culture group | deacylated gellan gum addition group |
|---|---|---|---|
| % Control | negative control | 100 | 100 |
| | human HB-EGF 10 ng/ml | 103 | 138 |
| | human HB-EGF 30 ng/ml | 103 | 191 |
| | human HB-EGF 100 ng/ml | 121 | 282 |

TABLE 77

| culture conditions day 9 | | single layer culture group | deacylated gellan gum addition group |
|---|---|---|---|
| % Control | negative control | 100 | 100 |
| | human HB-EGF 10 ng/ml | 100 | 136 |
| | human HB-EGF 30 ng/ml | 101 | 176 |
| | human HB-EGF 100 ng/ml | 108 | 343 |

Experimental Example 58: Comparison with Single Layer Culture Method in VEGF mRNA Expression in HeLa Cells Stimulated with Human HB-EGF Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO), and a medium composition free of deacylated gellan gum was prepared. Successively, human cervical cancer cell line HeLa (manufactured by DS PHARMA BIOMEDICAL CO., LTD.) was inoculated to the above-mentioned medium composition added with deacylated gellan gum at 37000 cells/mL, and dispensed to the wells of a 96-well flat bottom ultra low adhesion surface microplate (manufactured by Corning Incorporated, #3474) at 135 µL/well. In the single layer culture method, human cervical cancer cell line HeLa was inoculated to the above-mentioned medium composition free of deacylated gellan gum at 37000 cells/mL, and dispensed to the wells of a 96-well flat bottom microplate (manufactured by Corning Incorporated, #3585) at 135 µL/well. Each plate was cultured by being stood still in a $CO_2$ incubator (37° C., 5% $CO_2$). On culture day 1, a medium composition containing a 10-fold concentration of human HB-EGF (manufactured by PEPROTECH) to make the final concentration from 10, 30 and 100 ng/ml, and a final concentration 0.015% (w/v) of deacylated gellan gum (deacylated gellan gum addition group), and a medium composition containing only a 10-fold concentration of human HB-EGF (single layer culture group) were each added by 15 µL, and the cells were successively cultured for 6 days. The culture medium containing cancer cells on day 7 was recovered, and the cells were recovered by centrifugation (400 g, 3 min). Total RNA was extracted from the cells by using RNeasy Mini kit (manufactured by QIAGEN). Using total RNA and PrimeScript (registered trade mark) RT Master Mix (manufactured by Takara Bio Inc.), a reverse transcription reaction was performed using GeneAmp PCR System 9700 (manufactured by Applied Biosystems), and cDNA was synthesized. Each cDNA sample used in PCR reaction was dispensed and diluted with sterilization water to 1/10. In addition, the sample used for the calibration curve was cDNA dispensed and mixed, and adjusted within the quantification range of 1/3 to 1/243 dilution at a 3-fold common ratio. The PCR reaction was performed using each cDNA sample, a calibration sample, Premix Ex Taq (registered trade mark) (manufactured by Takara Bio Inc.) and various Taqman probes (manufactured by Applied Biosystems), and 7500 Real-time PCR System (manufactured by Applied Biosystems). Specificity was calculated using mRNA of GAPDH (Glyceraldehyde 3-phosphate dehydrogenase) as an endogenous control, amending the expression of VEGF (Vascular endothelial growth factor) mRNA with the value of GAPDH, and using a negative control as 100%. Each probe (manufactured by Applied Biosystems) used is shown below.

GAPDH: H599999905
VEGF: H500173626

As a result, it was found that the HeLa cells cultured using the medium composition of the present invention strongly showed mRNA expression promoting effect of VEGF by human HB-EGF as compared to the single layer culture method. In addition, the VEGF mRNA expression value when the negative control on day 7 of the static culture is 100% is shown in Table 78.

TABLE 78

| | culture conditions day 7 | single layer culture group | deacylated gellan gum addition group |
|---|---|---|---|
| % Control | negative control | 100 | 100 |
| | human HB-EGF 10 ng/ml | 82 | 121 |
| | human HB-EGF 30 ng/ml | 88 | 148 |
| | human HB-EGF 100 ng/ml | 89 | 195 |

Experimental Example 59: Effect of Gefinitib on Cell Proliferation of A549 Cell Stimulated with Human HB-EGF Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to DMEM medium containing 10% (v/v) fetal bovine serum (manufactured by WAKO), and a medium composition free of deacylated gellan gum was prepared. Successively, human lung cancer cell line A549 (manufactured by DS PHARMA BIOMEDICAL CO., LTD.) was inoculated to the above-mentioned medium composition added with deacylated gellan gum at 14800 cells/mL, and dispensed to the wells of a 96-well flat bottom ultra low adhesion surface microplate (manufactured by Corning Incorporated, #3474) at 135 µL/well. Each plate was cultured by being stood still in a $CO_2$ incubator (37° C., 5% $CO_2$). On culture day 1, to make the final concentration 0.1 to 30 µm for each anticancer drug and the final concentration 0 ng/ml or 100 ng/ml for human HB-EGF, a medium composition containing a 10-fold concentration of each anticancer drug, human HB-EGF (manufactured by PEPROTECH) and a final concentration 0.015% (w/v) of deacylated gellan gum (deacylated gellan gum addition group) was each added by 15 µL, and the cells were successively cultured for 5 days. The anticancer drug used was Gefitinib (manufactured by Santa Cruz, EGF receptor inhibitor). To the culture medium on day 6 was added an ATP reagent (150 µL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, according to the A549 cell proliferation test method using the medium composition of the present invention and human HB-EGF, the culture conditions added with HB-EGF showed a stronger suppressive effect of Gefitinib. The % Control value of the RLU value (ATP measurement, luminescence intensity) on day 6 of the static culture is shown in Table 79.

TABLE 79

| | culture conditions day 6 | HB-EGF no addition | HB-EGF 100 ng/ml |
|---|---|---|---|
| % Control | DMSO | 100 | 100 |
| | Gefitinib 0.1 µM | 89 | 91 |
| | Gefitinib 0.3 µM | 84 | 74 |
| | Gefitinib 1 µM | 77 | 59 |
| | Gefitinib 3 µM | 69 | 53 |

Experimental Example 60: Effect of Gefinitib, Erlotinib on Growth Proliferated Action of A431 Cells Stimulated with Human HB-EGF Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to EMEM medium (manufactured by DS PHARMA BIOMEDICAL CO., LTD.) containing 10% (v/v) fetal bovine serum, and a medium composition free of deacylated gellan gum was prepared. Successively, human squamous carcinoma cell line A431 (manufactured by DS PHARMA BIOMEDICAL CO., LTD.) was inoculated to the above-mentioned medium composition added with deacylated gellan gum at 37000 cells/mL, and dispensed to the wells of a 96-well flat bottom ultra low adhesion surface microplate (manufactured by Corning Incorporated, #3474) at 135 μL/well. Each plate was cultured by being stood still in a $CO_2$ incubator (37° C., 5% $CO_2$). On culture day 1, to make the final concentration 0.1 to 30 μm for each anticancer drug and the final concentration of 0 ng/ml or 100 ng/ml for human HB-EGF, a medium composition containing a 10-fold concentration of each anticancer drug, human HB-EGF (manufactured by PEPROTECH) and a final concentration 0.015% (w/v) of deacylated gellan gum (deacylated gellan gum addition group) was each added by 15 μL, and the cells were successively cultured for 7 days. The anticancer drugs used were Gefitinib (manufactured by Santa Cruz, EGF receptor inhibitor) and Erlotinib (manufactured by Santa Cruz, EGF receptor inhibitor). To the culture medium on days 4, 6 and 8 was added an ATP reagent (150 μL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, by the culture method combining the medium composition of the present invention and human HB-EGF, A431 cell proliferation under low adhesion culture conditions was observed. Furthermore, by the A431 cell proliferation test method combining the medium composition of the present invention and human HB-EGF, suppressive effects of Gefitinib and Erlotinib on an HB-EGF-induced cell proliferation could be evaluated. For the human HB-EGF growth promoting action, the RLU value (ATP measurement, luminescence intensity) on day 4, day 6, day 8 of the static culture is shown in Table 80. Furthermore, for an action of each anticancer drug on a human HB-EGF proliferation promoting action, the % Control value of the RLU value (ATP measurement, luminescence intensity) on day 4, day 8 is shown in Table 81.

TABLE 80

| | culture conditions | HB-EGF no addition | HB-EGF 100 ng/ml |
|---|---|---|---|
| cell number | day 4 | 2532 | 15303 |
| | day 6 | 1332 | 23273 |
| | day 8 | 613 | 38854 |

TABLE 81

| | culture conditions | day 4 | day 8 |
|---|---|---|---|
| % Control | DMSO | 100 | 100 |
| | Gefitinib 0.1 μM | 83 | 68 |
| | Gefitinib 0.3 μM | 82 | 45 |
| | Gefitinib 1 μM | 10 | 2 |
| | Gefitinib 3 μM | 3 | 0 |
| | Elrotinib 0.1 μM | 88 | 56 |
| | Elrotinib 0.3 μM | 89 | 27 |
| | Elrotinib 1 μM | 21 | 4 |
| | Elrotinib 3 μM | 4 | 0 |

Experimental Example 61: Cell Proliferation Test by Dispersing MCF-7 Cells

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.005% (w/v) or 0.015% (w/v) to EMEM medium (manufactured by DS PHARMA BIOMEDICAL CO., LTD.) containing 10% (v/v) fetal bovine serum. Successively, human breast cancer cell line MCF-7 (manufactured by DS PHARMA BIOMEDICAL CO., LTD.) was inoculated to the above-mentioned medium composition added with deacylated gellan gum at 50000 cells/mL, and dispensed to the wells of a 96-well flat bottom ultra low adhesion surface microplate (manufactured by Corning Incorporated, #3474) at 100 μL/well. As a negative control, MCF-7 cells were suspended in the above-mentioned medium free of deacylated gellan gum and the suspension was dispensed. Successively, this plate was cultured by being stood still in a $CO_2$ incubator (37° C., 5% $CO_2$) for 5 days. To the culture medium after culturing for 2 and 5 days was added an ATP reagent (100 μL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone. For WST-8 measurement, a WST-8 solution (manufactured by DOJINDO Laboratories, 10 μL) was added to the cells after culturing for 2 and 5 days, the mixture was incubated at 37° C. for 100 min, the absorbance at 450 nm was measured by an absorbance spectrometer (manufactured by Molecular Devices, SPECTRA MAX 190), and the number of viable cells was measured by subtracting the absorbance of the medium alone.

Figure 23:
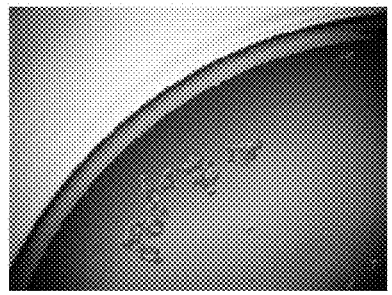
FIG. 23 is a Figure showing MCF-7 cell aggregates after culturing MCF-7 cells for 5 days in the medium composition of the present invention.
Figure 23:

As a result, it was confirmed that, using the medium composition of the present invention, MCF-7 cells efficiently proliferates according to the ATP measurement method and WST-8 measurement method. The RLU value (ATP measurement, luminescence intensity) after static culture for 2, 5 days is shown in Table 82. The absorbance at 450 nm (WST-8) after static culture for 2, 5 days is shown in Table 83. The results of microscopic observation of an aggregate of MCF-7 cells after culture for 5 days are shown in FIG. 23.

TABLE 82

| | culture day number | 2 | 5 |
|---|---|---|---|
| cell number | negative control | 5765 | 9556 |
| | deacylgellan gum 0.005% | 6242 | 15103 |
| | deacylgellan gum 0.015% | 6024 | 18314 |

TABLE 83

| | culture day number | 2 | 5 |
|---|---|---|---|
| cell number | negative control | 0.070 | 0.095 |
| | deacylgellan gum 0.005% | 0.075 | 0.117 |
| | deacylgellan gum 0.015% | 0.065 | 0.173 |

Experimental Example 62: Cell Proliferation Test when A375 Cell and MNNG/HOS Cells were Dispersed Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.005% (w/v) or 0.015% (w/v) to DMEM medium containing 10% (v/v) fetal bovine serum (manufactured by WAKO) or EMEM medium (manufactured by DS PHARMA BIOMEDICAL CO., LTD.). Successively, each human melanoma cell line A375 (manufactured by ATCC) and human osteosarcoma cancer cell line MNNG/HOS (manufactured by ATCC) was inoculated to the above-mentioned medium composition added with deacylated gellan gum at 50000 cells/mL, and dispensed to the wells of a 96-well flat bottom ultra low adhesion surface microplate (manufactured by Corning Incorporated, #3474) at 100 µL/well. As a negative control, A375 cells and MNNG/HOS cells were suspended in the above-mentioned medium free of deacylated gellan gum and the suspension was dispensed. Successively, this plate was cultured by being stood still in a $CO_2$ incubator (37° C., 5% $CO_2$) for 4 days. To the culture medium after culturing for 4 days was added an ATP reagent (100 µL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone. After culturing for 4 days, to the culture medium was added a WST-8 solution (manufactured by DOJINDO Laboratories, 10 µL), the mixture was incubated at 37° C. for 100 min, the absorbance at 450 nm was measured by an absorbance spectrometer (manufactured by Molecular Devices, SPECTRA MAX 190), and the number of viable cells was measured by subtracting the absorbance of the medium alone.

Figure 24:
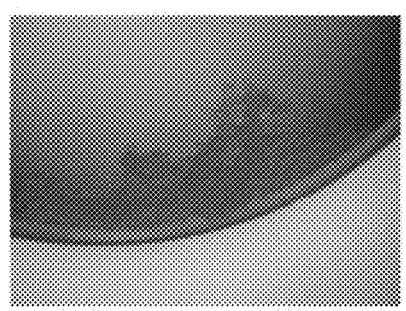
FIG. 24 is a Figure showing aggregates after culturing A375 cells and MNNG/HOS cells for 4 days in the medium composition of the present invention.
Figure 24:
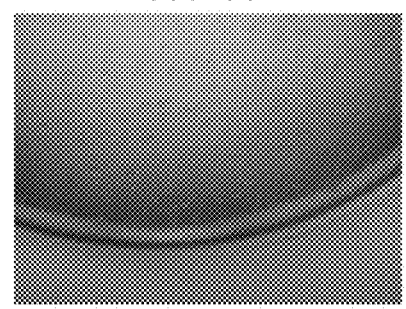
Figure 24:
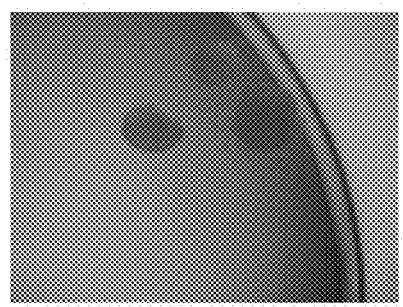
Figure 24:
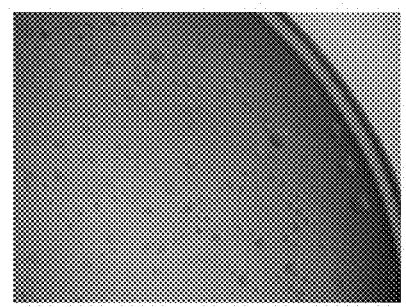

As a result, it was confirmed that, using the medium composition of the present invention, A375 cells and MNNG/HOS cells can be cultivated in a uniformly dispersed state without forming a cell aggregate having an excessive size, and efficiently proliferates in the medium composition. The results of microscopic observation of aggregates of A375 cells and MNNG/HOS cells after culture for 4 days are shown in FIG. 24. In addition, in A375 cells, the absorbance at 450 nm (WST-8) and RLU value (ATP measurement, luminescence intensity) after static culture for 4 days are shown in Table 84. In MNNG/HOS cells, the absorbance at 450 nm (WST-8) and RLU value (ATP measurement, luminescence intensity) after static culture for 4 days are shown in Table 85.

TABLE 84

| experiment group | WST-8 | ATP |
| --- | --- | --- |
| negative control | 0.738 | 55193 |
| deacylgellan gum 0.005% | 2.088 | 98739 |
| deacylgellan gum 0.015% | 3.336 | 115365 |

TABLE 85

| experiment group | WST-8 | ATP |
| --- | --- | --- |
| negative control | 0.294 | 41529 |
| deacylgellan gum 0.005% | 0.843 | 66913 |
| deacylgellan gum 0.015% | 2.197 | 102199 |

Experimental Example 63: Cell Proliferation Test by Dispersing MIAPaCa-2 Cells

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.005% (w/v) or 0.015% (w/v) to DMEM medium containing 10% (v/v) fetal bovine serum (manufactured by WAKO). Successively, human pancreatic carcinoma cell line MIAPaCa-2 (manufactured by ATCC) was inoculated to the above-mentioned medium composition added with deacylated gellan gum at 50000 cells/mL, and dispensed to the wells of a 96-well flat bottom ultra low adhesion surface microplate (manufactured by Corning Incorporated, #3474) at 100 µL/well. As a negative control, MIAPaCa-2 cells were suspended in the above-mentioned medium free of deacylated gellan gum and the suspension was dispensed. Successively, this plate was cultured by being stood still in a $CO_2$ incubator (37° C., 5% $CO_2$) for 6 days. To the culture medium after culturing for 6 days was added an ATP reagent (100 µL) (CellTiter-Glo (registered trade mark) Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone. After culturing for 6 days, to the culture medium was added a WST-8 solution (manufactured by DOJINDO Laboratories, 10 µL), the mixture was incubated at 37° C. for 100 min, the absorbance at 450 nm was measured by an absorbance spectrometer (manufactured by Molecular Devices, SPECTRA MAX 190), and the number of viable cells was measured by subtracting the absorbance of the medium alone.

Figure 25:
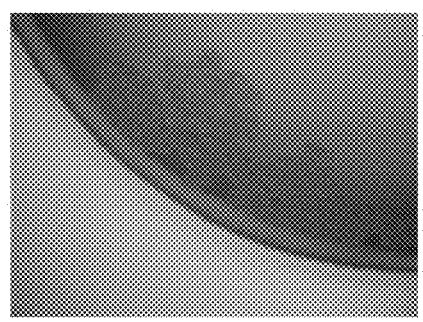
FIG. 25 is a Figure showing aggregates after culturing MIAPaCa-2 cells for 6 days in the medium composition of the present invention.
Figure 25:
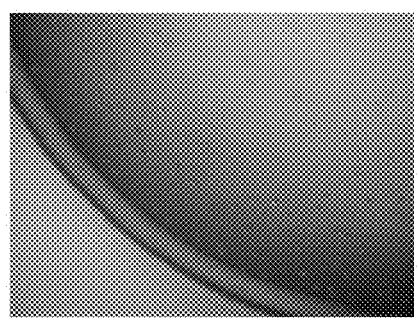

As a result, it was confirmed that, using the medium composition of the present invention, MIAPaCa-2 cells can be cultivated in a uniformly dispersed state without forming a cell aggregate having an excessive size, and efficiently proliferates in the medium composition. The results of microscopic observation of aggregate of MIAPaCa-2 cells after culture for 6 days are shown in FIG. 25. In addition, the absorbance at 450 nm (WST-8) and RLU value (ATP measurement, luminescence intensity) of MIAPaCa-2 cells after static culture for 4 days are shown in Table 86.

TABLE 86

| experiment group | WST-8 | ATP |
| --- | --- | --- |
| negative control | 2.030 | 52674 |
| deacylgellan gum 0.005% | 3.102 | 86650 |
| deacylgellan gum 0.015% | 3.621 | 85412 |

Experimental Example 64: Concentration and Dilution of Deacylated Gellan Gum-Containing Medium DMEM medium (manufactured by WAKO) containing 0.015% (w/v) deacylated gellan gum (KELCOGEL CG-LA, manufactured by SANSHO Co., Ltd.) prepared in the same manner as in Experimental Example 2 was dispensed in a 15 mL centrifugation tube (manufactured by VIOLAMO) by 10 mL, and the deacylated gellan gum was sedimented by centrifugation (700G, 5 min) in swing rotor LC-200 (manufactured by TOMY SEIKO Co., Ltd.). The supernatant (8 mL) was removed by an aspirator, whereby the medium containing deacylated gellan gum was concentrated. Furthermore, DMEM medium (manufactured by WAKO) free of deacylated gellan gum was added to this concentrated medium, and mixed by pipetting to give a medium having an optional concentration rate.

On the other hand, human liver cancer cell HepG2 (manufactured by DS PHARMA BIOMEDICAL CO., LTD.) was suspended in DMEM medium containing 10% (v/v) fetal bovine serum (manufactured by WAKO) at 500000 cells/mL, this suspension (10 mL) was inoculated to EZ SPHERE (manufactured by ASAHI GLASS CO., LTD.), and the cells were cultured in a 37° C., $CO_2$ incubator (5% $CO_2$) for 7 days. Here, a suspension (10 mL) of the obtained sphere (diameter 100-200 μm) was centrifuged (200G, 5 min) to allow for sedimentation, and the supernatant was removed to prepare a sphere suspension (1.0 mL). To the medium prepared to the above-mentioned optional concentration was added this sphere suspension by 100 μL, the spheres were dispersed by pipetting and incubated at 37° C., and the dispersed state of the spheres was visually observed 1 hr later. The results are shown in Table 87.

As shown in Table 87, deacylated gellan gum can be concentrated and diluted to an optional concentration, after preparing as a medium composition. The medium composition concentrated and diluted in this manner was confirmed to have a suspending effect of the spheres.

TABLE 87

| | concentration rate (fold) of deacylated gellan gum | | | | | |
|---|---|---|---|---|---|---|
| | 0.33 | 0.66 | 1.00 | 1.67 | 2.50 | 5.00 |
| state (sedimented or suspended) of sphere | sedimented | suspended | suspended | suspended | suspended | suspended |

Experimental Example 65: Production of Deacylgellan Gum-Containing DMEM/Ham's F12 Medium Deacylated gellan gum (KELCOGEL CG-LA, manufactured by SANSHO Co., Ltd., 120 mg) was suspended in pure water (72 mL), and dissolved by stirring with heating at 90° C. Thereto was added pure water to prepare a 0.017% (w/v) solution (720 mL) of deacylgellan gum, and the solution was sterilized using a sterilization filter (pore size 0.22 μm). On the other hand, pure water corresponding to 1/10 of the amount recommended for preparation of a medium was added to a medium containing a mixed powder medium of equal amounts of DMEM/Ham's F12 (Life Technologies Corporation), and sodium hydrogen carbonate to prepare a 80 mL aqueous solution at a 10-fold concentration, and the solution was sterilized using a sterilization filter (pore size 0.22 μm). This was mixed with stirring at 25° C. under sterilization conditions to prepare the object medium (800 mL) having a deacylgellan gum concentration of 0.015% (w/v).

INDUSTRIAL APPLICABILITY

The medium composition of the present invention shows a superior effect of suspending cells and/or tissues, and is extremely useful for large-scale cultivation of cells and/or tissues derived from animals and plants while maintaining the function thereof. In addition, the cells and/or tissues cultured by the method of the present invention are extremely useful for efficacy and toxicity evaluation of chemical substances, pharmaceutical products and the like, large-scale production of useful substances such as enzymes, cell growth factors, antibodies and the like, and in the field of regenerative medicine for supplementing organ, tissue and cell that were lost by disease and deficiency, and the like.

The invention claimed is:

1. A medium composition comprising
   (i) a culture medium,
   (ii) deacylated gellan gum or a salt thereof,
   (iii) methylcellulose or a salt thereof,
   (iv) a recombinant fibroblast growth factor-2, and
   (v) a calcium ion.

2. The medium composition according to claim 1, wherein the composition has a viscosity of not more than 8 mPa·s at 37° C.

3. The medium composition according to claim 2, wherein the composition comprises deacylated gellan gum.

4. The medium composition according to claim 2, wherein the composition comprises a salt of deacylated gellan gum.

5. The medium composition according to claim 2, wherein the composition comprises methylcellulose.

6. The medium composition according to claim 2, wherein the composition comprises a salt of methylcellulose.

7. The medium composition according to claim 2, wherein the deacylated gellan gum or salt thereof and the methylcellulose or a salt thereof are present at a concentration which allows cells or a tissue to be cultured in suspension standing culture.

8. The medium composition according to claim 1, wherein the composition comprises deacylated gellan gum.

9. The medium composition according to claim 1, wherein the composition comprises a salt of deacylated gellan gum.

10. The medium composition according to claim 1, wherein the composition comprises methylcellulose.

11. The medium composition according to claim 1, wherein the composition comprises a salt of methylcellulose.

12. The medium composition according to claim 1, wherein the deacylated gellan gum or salt thereof and the methylcellulose or a salt thereof are present at a concentration which allows cells or a tissue to be cultured in suspension standing culture.

* * * * *